United States Patent
Benard et al.

(10) Patent No.: US 10,882,871 B2
(45) Date of Patent: Jan. 5, 2021

(54) 18/19F-LABELLED COMPOUNDS WHICH TARGET THE PROSTATE SPECIFIC MEMBRANE ANTIGEN

(71) Applicants: BRITISH COLUMBIA CANCER AGENCY BRANCH, Vancouver (CA); THE UNIVERSITY OF BRITISH COLUMBIA, Vancouver (CA)

(72) Inventors: Francois Benard, Vancouver (CA); Kuo-shyan Lin, Surrey (CA); David Perrin, Vancouver (CA); Zhibo Liu, Beijing (CN); Hsiou-ting Kuo, Vancouver (CA); Jinhe Pan, Richmond (CA); Aron Roxin, Norman, OK (US); Mathieu Lepage, Vancouver (CA)

(73) Assignees: British Columbia Cancer Agency Branch; The University of British Columbia

( * ) Notice: Subject to any disclaimer, the term of this patent is extended or adjusted under 35 U.S.C. 154(b) by 0 days.

(21) Appl. No.: 16/068,992

(22) PCT Filed: Jan. 10, 2017

(86) PCT No.: PCT/CA2017/050026
§ 371 (c)(1),
(2) Date: Jul. 10, 2018

(87) PCT Pub. No.: WO2017/117687
PCT Pub. Date: Jul. 13, 2017

(65) Prior Publication Data
US 2019/0010171 A1  Jan. 10, 2019

Related U.S. Application Data

(60) Provisional application No. 62/276,906, filed on Jan. 10, 2016.

(51) Int. Cl.

| | |
|---|---|
| *A61K 51/00* | (2006.01) |
| *A61M 36/14* | (2006.01) |
| *C07F 5/02* | (2006.01) |
| *A61K 51/04* | (2006.01) |
| *C07F 5/00* | (2006.01) |
| *A61P 35/00* | (2006.01) |
| *C07B 59/00* | (2006.01) |

(52) U.S. Cl.
CPC .......... *C07F 5/027* (2013.01); *A61K 51/0402* (2013.01); *A61K 51/0453* (2013.01); *A61K 51/0455* (2013.01); *A61K 51/0497* (2013.01); *A61P 35/00* (2018.01); *C07B 59/004* (2013.01); *C07F 5/003* (2013.01); *C07B 2200/05* (2013.01)

(58) Field of Classification Search
None
See application file for complete search history.

(56) References Cited

FOREIGN PATENT DOCUMENTS

| WO | WO 2008/058192 | 5/2008 |
|---|---|---|
| WO | WO 2009/002529 | 12/2008 |
| WO | WO 2010/014933 | 2/2010 |
| WO | WO 2013/028664 | 2/2013 |
| WO | WO 2013/028791 | 2/2013 |
| WO | WO 2015/073678 | 5/2015 |
| WO | WO 2015/100498 | 7/2015 |
| WO | WO 2015/135082 | 9/2015 |

OTHER PUBLICATIONS

Banerjee et al. "68Ga-Labeled Inhibitors of Prostate-Specific Membrane Antigen (PSMA) for Imaging Prostate Cancer," Journal of Medicinal Chemistry, 2010, vol. 53, pp. 5333-5341.
Banerjee et al. "64Cu-Labeled Inhibitors of Prostate-Specific Membrane Antigen for PET Imaging of Prostate Cancer," Journal of Medicinal Chemistry, 2014, vol. 57, pp. 2657-2669.
Berge et al. "Pharmaceutical Salts," Journal of Pharmaceutical Sciences, Jan. 1977, vol. 66, No. 1, pp. 1-19.
Bouvet et al. "Automated synthesis of [18F]DCFPyL via direct radiofluorination and validation in preclinical prostate cancer models," EJNMMI Research, 2016, vol. 6, Article 40, 15 pages.
Chen et al. "2-(3-{1-Carboxy-5-[(6-[18F]Fluoro-Pyridine-3-Carbonyl)-Amino]-Pentyl}-Ureido)-Pentanedioic Acid, [18F]DCFPyL, a PSMA-Based PET Imaging Agent for Prostate Cancer," Clinical Cancer Research, Dec. 2011, vol. 17, No. 24, pp. 7645-7653.
Eder et al. "68Ga-Complex Lipophilicity and the Targeting Property of a Urea-Based PSMA Inhibitor for PET Imaging," Bioconjugate Chemistry, 2012, vol. 23, pp. 68-697.

(Continued)

*Primary Examiner* — Michael G. Hartley
*Assistant Examiner* — Melissa J Perreira
(74) *Attorney, Agent, or Firm* — Sheridan Ross P.C.

(57) ABSTRACT

This disclosure relates to novel compounds comprising a zwitterionic trifluoroborate prosthetic group which target prostate-specific membrane antigen (PSMA), e.g. in prostate cancer. The compounds have Formula I, wherein each R1 is an anionic group, L is a linker and R2B-F3 is —N(R³)₂CH₂BF₃, a pyridinium group substituted with BF₃ or methyl BF₃, or an azole group substituted with methyl BF3. Methods and uses of imaging and treating PSMA-expressing cancers are also disclosed.

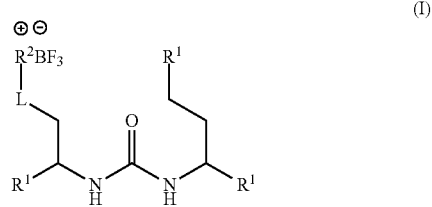

20 Claims, 10 Drawing Sheets

(56) References Cited

OTHER PUBLICATIONS

Horiuchi et al. "Discovery of novel thieno[2,3-d]pyrimidin-4-yl hydrazone-based inhibitors of Cyclin D1-CDK4: Synthesis, biological evaluation and structure-activity relationships. Part 2" Bioorganic & Medicinal Chemistry, 2009, vol. 17, pp. 7850-7860.

Huggins et al. "Studies on Prostatic Cancer II. The Effects of Castration on Advanced Carcinoma of the Prostate Gland," Archives of Surgery, 1941, vol. 43, No. 2, pp. 209-223.

Kularatne et al. "Prostate-Specific Membrane Antigen Targeted Imaging and Therapy of Prostate Cancer Using a PSMA Inhibitor as a Homing Ligand," Molecular Pharmaceutics, 2009, vol. 6, No. 3, pp. 780-789.

Liu et al. "An Organotrifluoroborate for Broadly Applicable One-Step 18F-Labeling," Anewandte Chemie International Edition, Sep. 2014, vol. 53, No. 44, pp. 11876-11880.

Liu et al. "Preclinical Evaluation of a High-Affinity 18F-Trifluoroborate Octreotate Derivative for Somatostatin Receptor Imaging," Journal of Nuclear Medicine, 2014, vol. 55, pp. 1499-1505.

Maresca et al. "A Series of Halogenated Heterodimeric Inhibitors of Prostate Specific Membrane Antigen (PSMA) as Radiolabeled Probes for Targeting Prostate Cancer," Journal of Medicinal Chemistry, 2009, vol. 52, No. 2, pp. 347-357.

Mukherjee et al. "Mechanistic Studies on the Substrate-Tolerant Lanthipeptide Synthetase ProcM," Journal of the American Chemical Society, 2014, vol. 136, pp. 10450-10459.

Pyka et al. "68Ga-PSMA-HBED-CC PET for Differential Diagnosis of Suggestive Lung Lesions in Patients with Prostate Cancer," Journal of Nuclear Medicine, 2016, vol. 57, pp. 367-371.

Rowe et al. "Imaging of metastatic clear cell renal cell carcinoma with PSMA-targeted 18F-DCFPyL PET/CT," Annals of Nuclear Medicine, Dec. 2015, vol. 29, No. 10, pp. 877-882.

Sathekge et al. "68Ga-PSMA imaging of metastatic breast cancer," European Journal of Nuclear Medicine and Molecular Imaging, Aug. 2015, vol. 42, No. 9, pp. 1482-1483.

Schottelius et al. "[111In]PSMA-I&T: expanding the spectrum of PSMA-I&T applications towards SPECT and radioguided surgery," EJNMMI Research, 2015, vol. 5, Article 68, 5 pages.

Verburg et al. "First evidence of PSMA expression in differentiated thyroid cancer using [68Ga]PSMA_HBED-CC PET/CT," European Journal of Nuclear Medicine and Molecular Imaging, 2015, vol. 42, pp. 1622-1623.

Zhou et al. "A Fluorogenic Probe for the Copper(I)-Catalyzed Azide-Alkyne Ligation Reaction: Modulation of the Fluorescence Emission via $3(n,-\pi^*)-(-\pi,-\pi^*)$ Inversion," Journal of the American Chemical Society, Jul. 2004, vol. 126, No. 29, pp. 8862-8863.

Extended Search Report for European Patent Application No. 17735797.7, dated Aug. 13, 2019, 8 pages.

International Search Report and Written Opinion prepared by the Canadian Intellectual Property Office dated Mar. 31, 2017, for International Application No. PCT/CA2017/050026.

Kopka et al. "Glu-Ureido-Based Inhibitors of Prostate-Specific Membrane Antigen: Lessons Learned During the Development of a Novel Class of Low-Molecular-Weight Theranostic Radiotracers," The Journal of Nuclear Medicine, Sep. 2017, vol. 58, No. 9 (Supple), pp. 17S-26S.

Liu et al. "From Minutes to Years: Predicting Organotrifluoroborate Solvolysis Rates," Chemistry—A European Journal, Mar. 2015, vol. 21, No. 10, pp. 3924-3928.

18/19F-LABELLED COMPOUNDS WHICH TARGET THE PROSTATE SPECIFIC MEMBRANE ANTIGEN

CROSS REFERENCE TO RELATED APPLICATIONS

This application is a national stage application under 35 U.S.C. 371 and claims the benefit of PCT Application No. PCT/CA2017/050026 having an international filing date of 10 Jan. 2017, which designated the United States, which PCT application claimed the benefit of U.S. Provisional Application No. 62/276,906 filed 10 Jan. 2016, the disclosures of each of which are incorporated herein by reference.

FIELD OF INVENTION

The present invention relates to novel fluorine-labeled compounds as well as uses/methods for these compounds, including but not limited to uses/methods for cancer imaging and therapies.

BACKGROUND OF THE INVENTION

Prostate cancer is the second leading cause of cancer-related deaths in men in the United States. According to the National Cancer Institute, it is estimated that approximately 238,590 men will have been diagnosed with prostate cancer and 29,720 men succumbing to the disease in 2013. Prostate cancer is a multi-factorial disease with age, diet, race, lifestyle, and genetics having been identified as contributors of tumorigenesis. With advancements in screening, early detection and treatment options, prognosis for prostate cancer patients have seen marked improvement. This is especially true for patients with low-grade prostate cancers where active surveillance may be sufficient. However, there are patients who present with aggressive or metastatic prostate cancer upon initial diagnosis. In such cases, treatment for metastatic prostate cancer may entail a combination of surgery, radiotherapy, chemotherapy, and hormone therapy. In 1941, Huggins and Hodges showed that androgen ablation via orchiectomy or exogenous estrogen administration can lead to the regression of primary and metastatic tumors (Huggins et al., 1941, Arch Surg 43: 209-223). Since then, androgen-deprivation therapy (ADT) has become an integral component of the standard of care for advanced prostate cancer. Patients tend to respond favourably to ADT, but treatment response is transient with relapse being inevitable. Although castration level of androgens is maintained, the disease remains androgen receptor (AR) dependent and progresses to a more lethal phenotype: castration-resistant prostate cancer (CRPC). Today, treatment for CRPC remains a significant clinical challenge. Therefore, early diagnosis of recurrent prostate cancer and the ability to select patients who can benefit from emerging treatment options are the keys to reduce prostate cancer mortality rate.

Positron emission tomography (PET), a highly sensitive and quantifiable molecular imaging modality, uses positron-emitter tagged radiotracers to characterize/assess/measure biological processes. In combination with CT (PET/CT) or MR (PET/MR) to increase anatomic resolution or soft tissue contrast respectively, PET has become an indispensible non-invasive imaging modality in oncology for cancer patient management. 2-[$^{18}$F]fluorodeoxyglucose ($^{18}$F-FDG) is widely used for diagnosis, staging and monitoring treatment response of cancer. However, $^{18}$F-FDG is not recommended for prostate cancer imaging due to slow glucose metabolism in prostate tumors. Other PET tracers targeting different metabolic pathways have been developed including: $^{11}$C-choline, $^{18}$F-fluorocholine, and $^{18}$F-fluoroethylcholine for phospholipid synthesis; $^{11}$C-methionine and anti-1-amino-3-[$^{18}$F]flurocyclobutyl-1-carboxylic acid ($^{18}$F-FACBC) for protein synthesis; and $^{11}$C-acetate and $^{18}$F-fluoroacetate for fatty acid synthesis. Despite the potential applications of these tracers for early diagnosis of prostate cancer, they are unable to guide treatment options.

Prostate specific membrane antigen (PSMA) is a membrane protein that expresses at a low level in normal tissues (except kidneys) but is highly up-regulated in advanced prostate cancer especially CRPC. Several radiolabeled PSMA-targeting tracers including $^{18}$F-DCFBC, $^{18}$F-DCFPYL, $^{68}$Ga-PSMA-HBED-CC, $^{68}$Ga-PSMA-617, $^{68}$Ga-PSMA I & T (FIG. 1) have been developed and successfully applied in the clinic for identifying PSMA-expressing prostate cancer and metastases. Most importantly in clinical trials, PSMA-617 radiolabeled with Lu-177, a therapeutic radionuclide, has shown efficacy (>50% positive response) in treating PSMA-expressing prostate cancer patients. This further emphasizes the need for a sensitive and readily accessible imaging agent which could be used in the clinic to identify PSMA-expressing prostate cancer patients to receive effective PSMA-targeted therapies (such as $^{177}$Lu-PSMA-617).

Although several radiolabeled PSMA-targeting tracers have been successfully used in the clinic, these tracers are not ideal for routine and widespread application. Due to the limited size (up to 50 mCi) of commercially available $^{68}$Ge-$^{68}$Ga generators, $^{68}$Ga-labeled PSMA-targeting tracers are generally prepared in only 1 to 2 clinical doses. In addition, due to the short physical half-life (68 min) of $^{68}$Ga, the use of $^{68}$Ga-labeled tracers is limited to medical centers that can afford the $^{68}$Ge-$^{68}$Ga generator and have radiochemistry staff/facility for preparation/QC of the tracers. On the other hand, $^{18}$F has a longer physical half-life (109.7 min) and can be produced easily on a large scale (several Ci) via a medical cyclotron. Therefore, $^{18}$F-labeled tracers (such as $^{18}$F-FDG) are ideal for production at a centralized radiopharmacy, and then being distributed to remote hospitals for imaging. However, the production of $^{18}$F-DCFBC and $^{18}$F-DCFPYL requires multiple reaction steps, and leads to low radiochemical yields. Besides, such multiple-step preparation remains a challenge for their production using a commercially available GMP-compliant synthesis module.

There is thus an unmet need in the field for improved $^{18}$F-labelled PET tracers for the non-invasive imaging of prostate cancer or other cancers or diseases that express PSMA. There is also a need for PSMA-targeting compounds (radiolabelled or otherwise) that are useful for treatment of patients with disease (e.g. cancer) that express PSMA (e.g. prostate cancer).

No admission is necessarily intended, nor should it be construed, that any of the preceding information constitutes prior art against the present invention.

SUMMARY OF THE INVENTION

Various embodiments of the present invention relate to a compound, the compound having Formula I or being a salt or solvate of Formula I

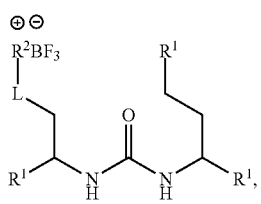
(I)

wherein: each $R^1$ is independently $CO_2H$, $PO_3H_2$, $SO_2H$, $SO_3H$, $SO_4H$ or $OPO_3H_2$; $R^2BF_3$ is: $-N(R^3)_2CH_2BF_3$ wherein each $R^3$ is independently: H, methyl, $X_2$-$X_{15}$ akyl, $X_2$-$X_{15}$ heteroalkyl, $X_3$-$X_{15}$ aryl or $X_3$-$X_{15}$ heteroaryl; wherein the $X_2$-$X_{15}$ akyl or the $X_2$-$X_{15}$ heteroalkyl is one or more of: branched or linear; acyclic, cyclic or multi-cyclic; saturated or unsaturated; and optionally substituted with one or more of halide, amide, oxo, hydroxyl, thiol, phosphate and sulfate; wherein the $X_3$-$X_{15}$ aryl or the $X_3$-$X_{15}$ heteroaryl is one or more of: cyclic or multi-cyclic; aromatic or nonaromatic; and optionally substituted with one or more of halide, amide, oxo, hydroxyl, thiol, phosphate and sulfate; wherein each X is independently C, N, O, P, S or Se; and wherein the N in the $-N(R^3)_2CH_2BF_3$ is linked to the $X_2$-$X_{15}$ akyl, the $X_2$-$X_{15}$ heteroalkyl, the $X_3$-$X_{15}$ aryl or the $X_3$-$X_{15}$ heteroaryl through at least two C atoms in the $X_2$-$X_{15}$ akyl, the $X_2$-$X_{15}$ heteroalkyl, the $X_3$-$X_{15}$ aryl or the $X_3$-$X_{15}$ heteroaryl; or $R^2BF_3$ forms a pyridinium group that is C-substituted with $-B^-F_3$ or N— substituted with $-CH_2B^-F_3$, and which is optionally substituted with one or more halogens, methyl groups, aryl groups, branched or linear alkyl groups, hydroxyls, esters, thiols, thioethers, amines, ketones, carboxaldehyde, carboxylates, carboxamides, nitriles, monohalomethyl groups, dihalomethyl groups and trihalomethyl groups; or $R^2BF_3$ forms:

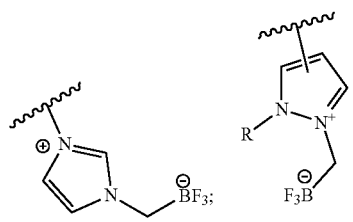

in which R is alkyl or aryl;

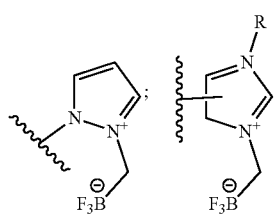

in which R is alkyl or aryl;

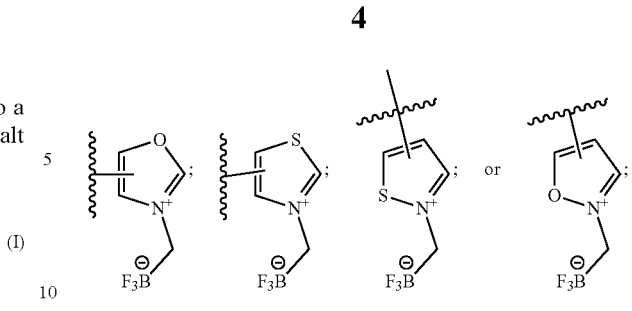

wherein the azole ring is optionally further substituted with one or more halogens, alkyls, ketones, carboxaldehyde, carboxylates, carboxamides, nitriles, monohalomethyl groups, dihalomethyl groups and trihalomethyl groups; and L is ether, ester, thioether, disulfide, thioester, amide, carbamate, ureido, phosphodiester, polyethylene glycol (PEG), peptide, polypeptide or $R^4R^5R^6$ in which $R^4$, $R^5$ and $R^6$ together form $X_1$-$X_{100}$ alkyl, $X_1$-$X_{100}$ heteroalkyl, $X_3$-$X_{100}$ aryl or $X_3$-$X_{100}$ heteroaryl, wherein the $X_1$-$X_{100}$ alkyl or the $X_1$-$X_{100}$ heteroalkyl of $R^4R^5R^6$ is one or more of: branched or linear; acyclic, cyclic or multi-cyclic; saturated or unsaturated; and optionally substituted with one or more of halide, amide, oxo, hydroxyl, thiol, phosphate and sulfate; wherein the $X_3$-$X_{15}$ aryl or the $X_3$-$X_{15}$ heteroaryl is one or more of: cyclic or multi-cyclic; aromatic or nonaromatic; and optionally substituted with one or more of halide, amide, oxo, hydroxyl, thiol, phosphate and sulfate; and wherein each X is independently C, N, O, P, S or Se.

The compound may have Formula II or a salt or solvate thereof

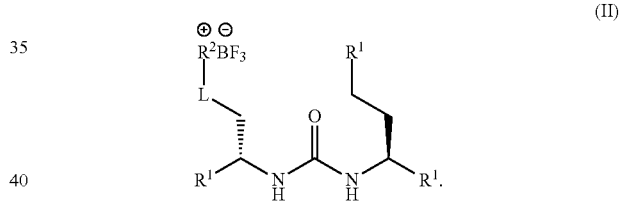
(II)

$R^1$ may be $CO_2H$.
$R^2BF_3$ may form

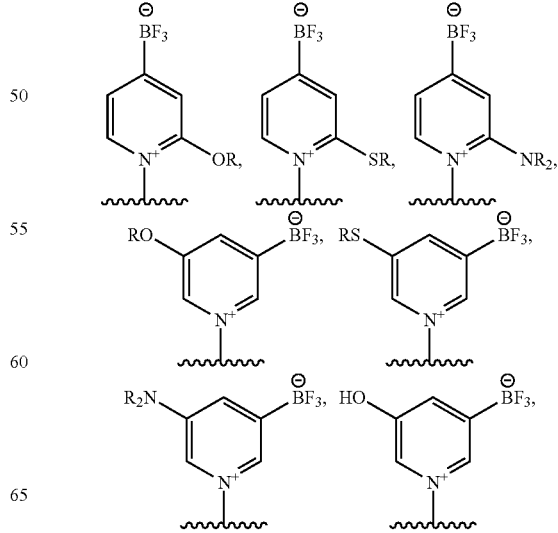

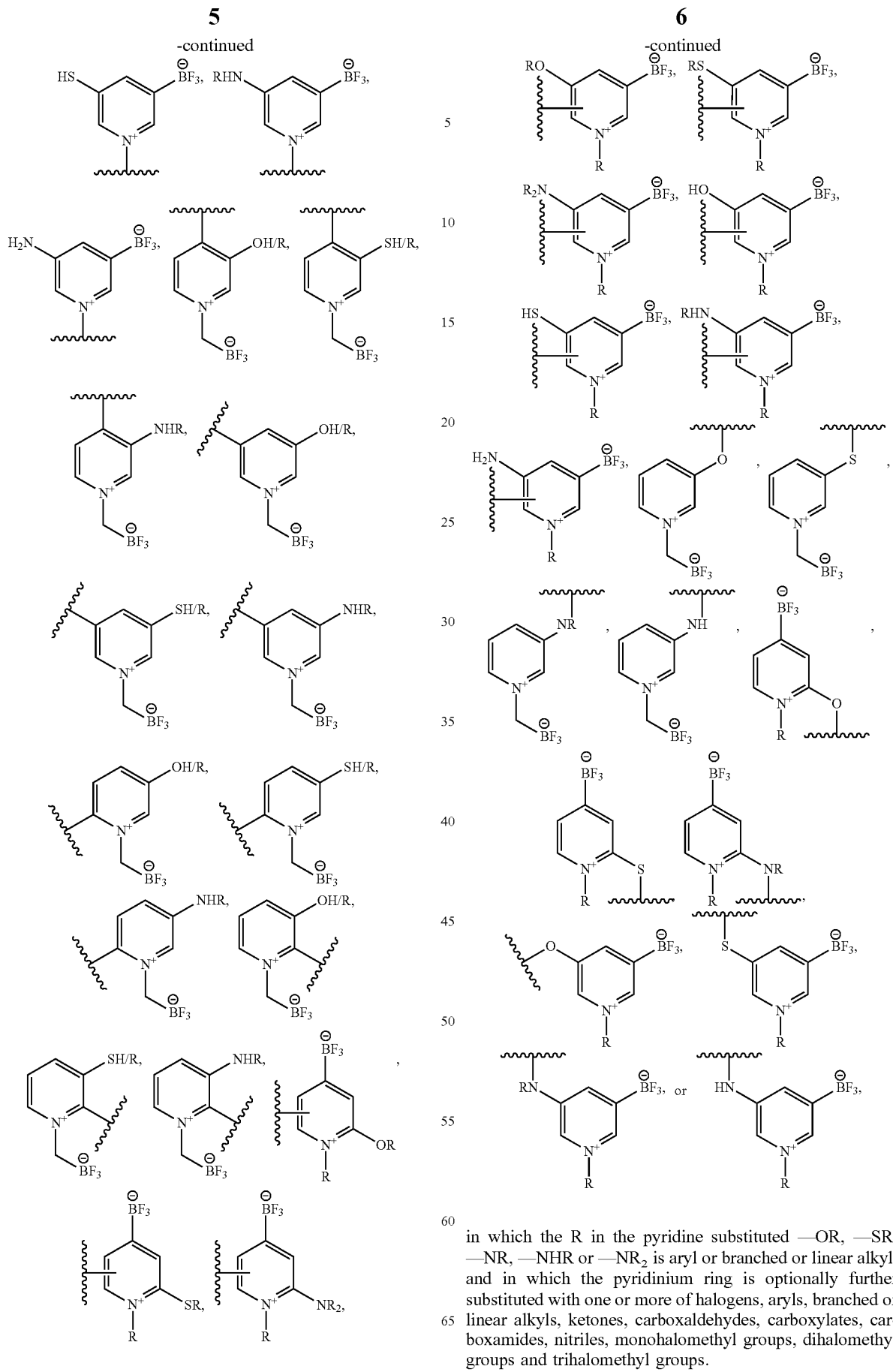

in which the R in the pyridine substituted —OR, —SR, —NR, —NHR or —NR$_2$ is aryl or branched or linear alkyl, and in which the pyridinium ring is optionally further substituted with one or more of halogens, aryls, branched or linear alkyls, ketones, carboxaldehydes, carboxylates, carboxamides, nitriles, monohalomethyl groups, dihalomethyl groups and trihalomethyl groups.

R²BF₃ may form
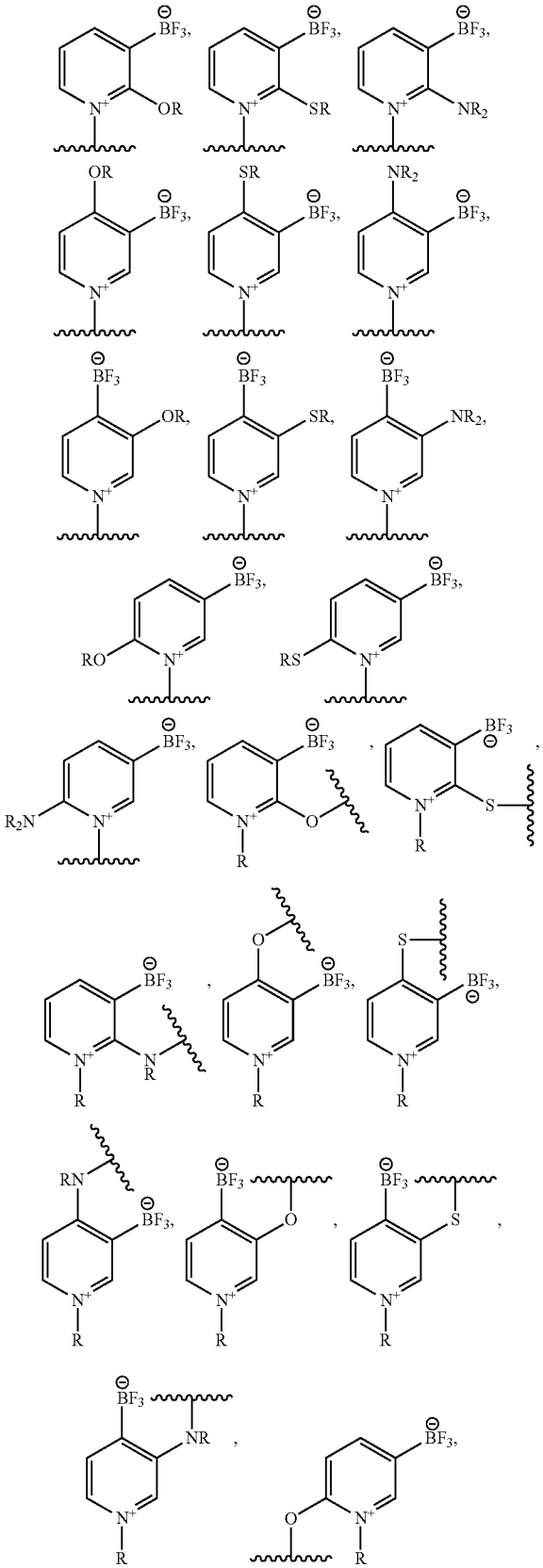
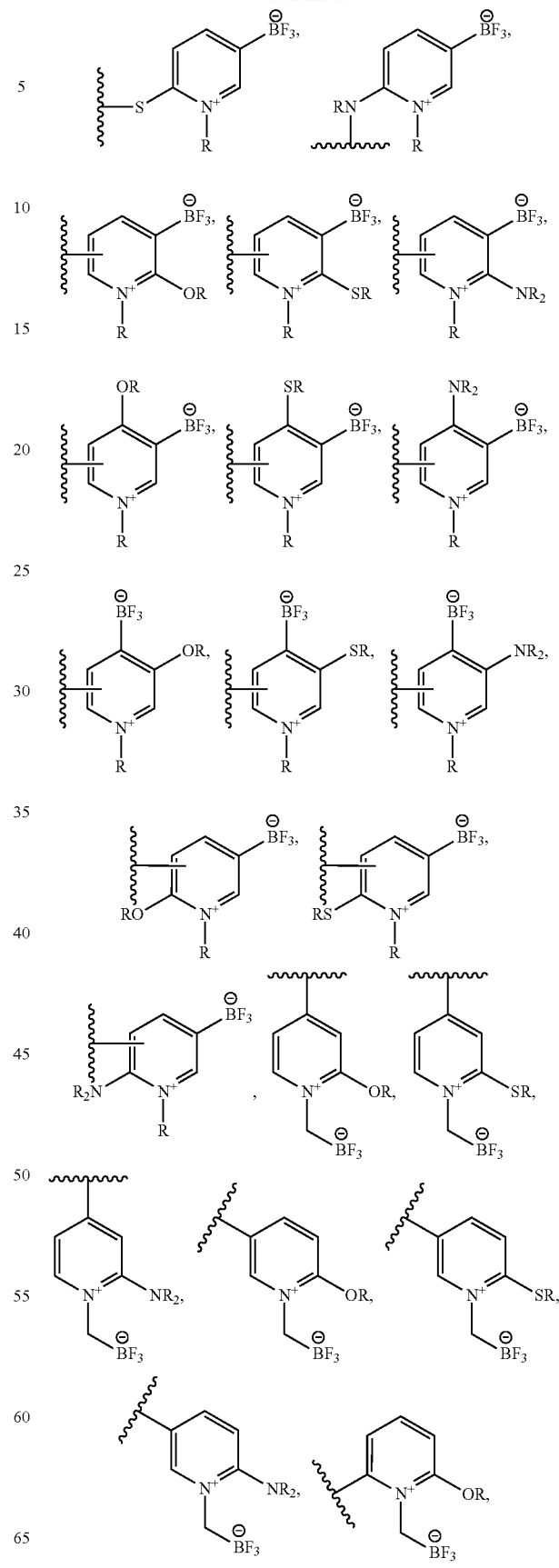

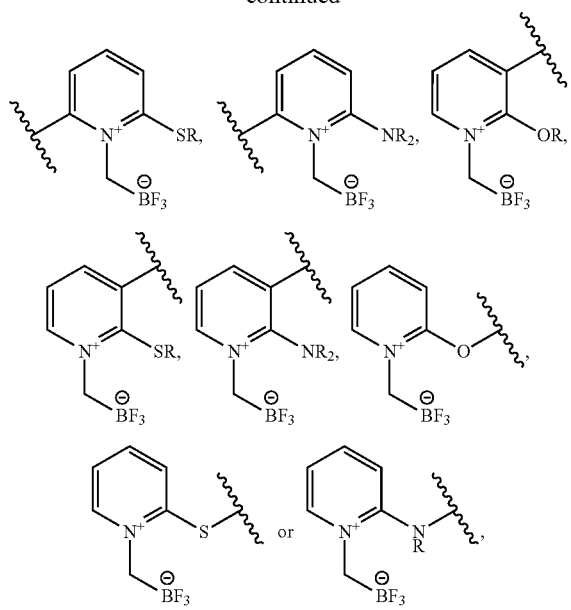

in which the R in the pyridine substituted —OR, —SR, —NR— or —NR$_2$ is aryl or branched or linear alkyl, and in which the pyridinium ring is optionally further substituted with one or more of halogens, aryls, branched or linear alkyls, ketones, carboxaldehydes, carboxylates, carboxamides, nitriles, monohalomethyl groups, dihalomethyl groups and trihalomethyl groups.

R$^2$BF$_3$ may be

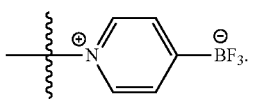

R$^4$ may be absent, —CH$_2$—, —CH$_2$CH$_2$— or —CH$_2$CH$_2$CH$_2$.

R$^5$ may be —S—, —NHC(O)—, —C(O)—, —C(O)O— or —OC(O)—.

R$^6$ may be (phenyl)CH$_2$R$^7$. R$^6$ may be (pyridyl)CH$_2$R$^7$. R$^6$ may be

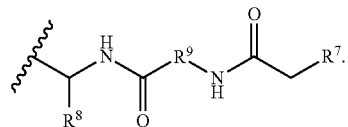

R$^6$ may be

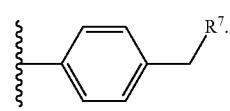

R$^6$ may be

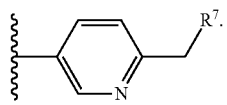

R$^6$ may be

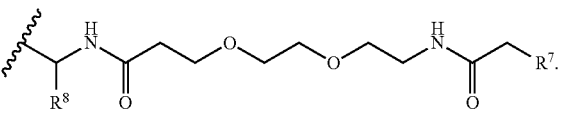

R$^6$ may be

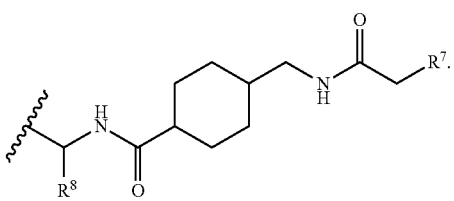

R$^7$ may be absent or may be

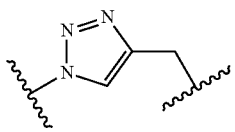

R$^8$ may be an aliphatic or aromatic hydrophobic side chain of a natural or artificial amino acid. R8 may be:

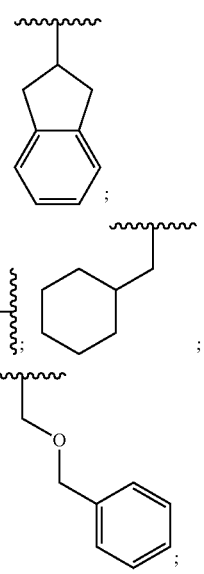

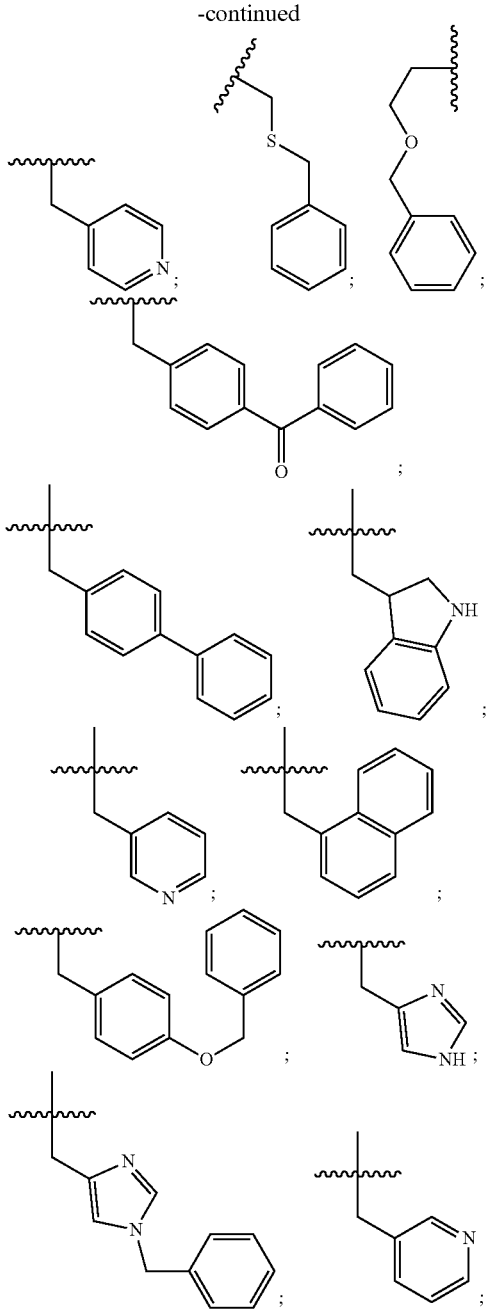

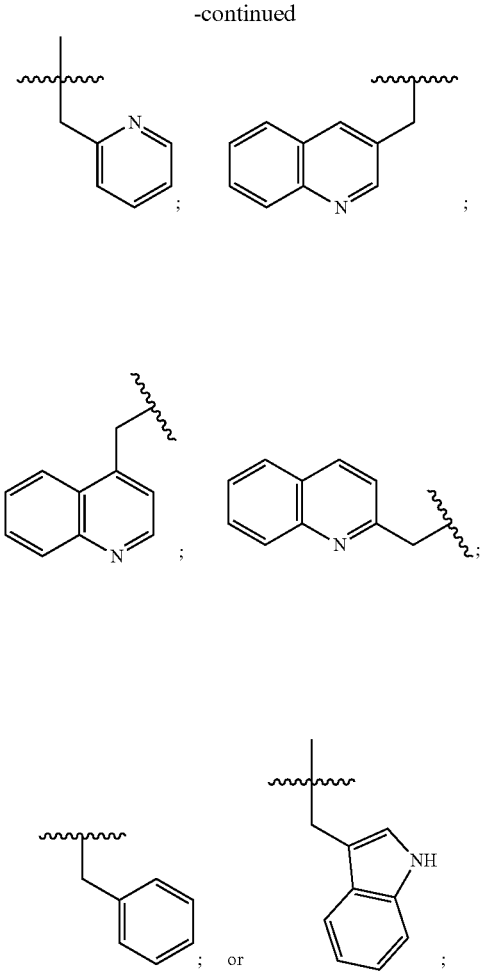

which is unsubstituted or substituted with one or more of halogen, nitro, carboxy, carboxamide, hydroxyl, $C_1$-$C_4$ alkyl, $C_1$-$C_4$ alkoxy, thiol, thioether or cyano groups at any or multiple positions on the ring.

$R^9$ may be an $X_1$-$X_{30}$ alkyl or $X_1$-$X_{30}$ heteroalkyl that is one or more of: branched or linear; acyclic, cyclic or multi-cyclic; saturated or unsaturated; and optionally substituted with one or more of halide, amide, oxo, hydroxyl, thiol, phosphate and sulfate; wherein each X is independently C, N, O, P, S or Se.

The compound may be:

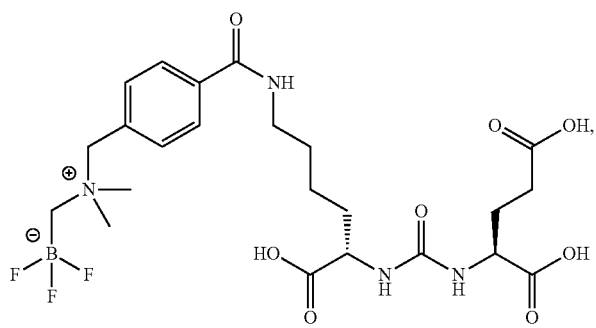

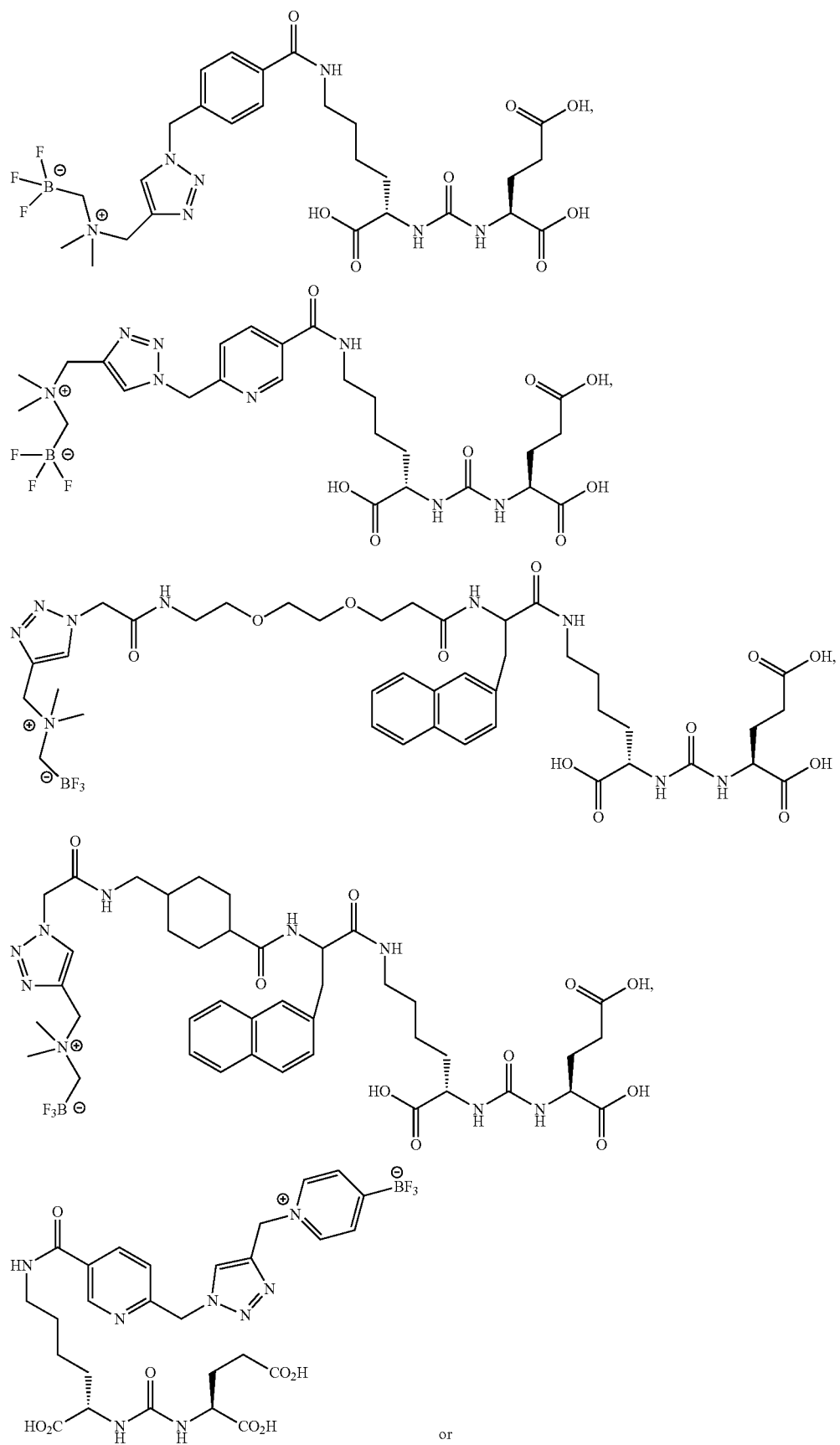

-continued

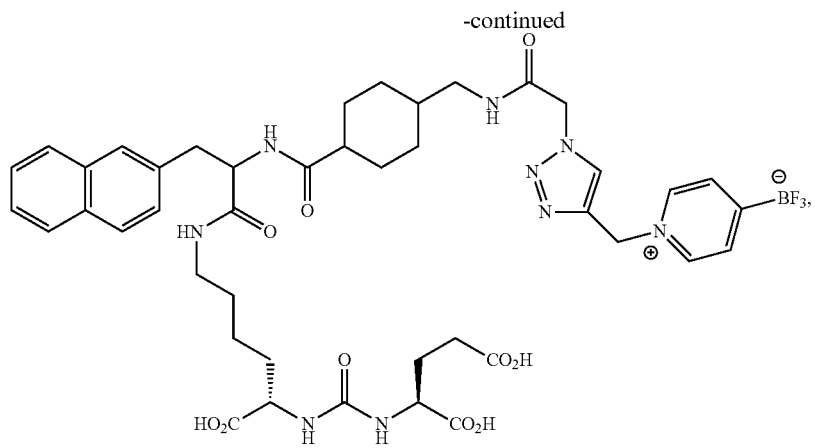

or a salt or solvate thereof.

In certain embodiments, at least one fluorine in the —BF$_3$ moiety of the compound is $^{18}$F.

Various embodiments of the present invention relate to a pharmaceutical composition comprising the compound as defined herein and a pharmaceutically acceptable excipient. In certain embodiments, an $^{18}$F-labeled compound (or composition comprising the $^{18}$F-labeled compound) may be used as a radiolabeled tracer for imaging prostate specific membrane antigen (PSMA)-expressing cancer in a subject. Certain compounds defined herein may be used for treating prostate specific membrane antigen (PSMA)-expressing cancer in a subject.

Various embodiments of the present invention relate to a method of imaging prostate specific membrane antigen (PSMA)-expressing cancer in a subject, the method comprising: administering to the subject a composition comprising a $^{18}$F-labeled compound as defined herein and a pharmaceutically acceptable excipient; and imaging tissue of the subject using positron emission tomography (PET).

Various embodiments of the present invention relate to a method of treating prostate specific membrane antigen (PSMA)-expressing cancer in a subject, the method comprising: administering to the subject a composition comprising the compound as defined herein and a pharmaceutically acceptable excipient.

The cancer may be prostate cancer, renal cancer, breast cancer, thyroid cancer, gastric cancer, colorectal cancer, bladder cancer, pancreatic cancer, lung cancer, liver cancer, brain tumor, melanoma, neuroendocrine tumor, ovarian cancer or sarcoma.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 2.

FIG. 3.

DETAILED DESCRIPTION

Figure 1:
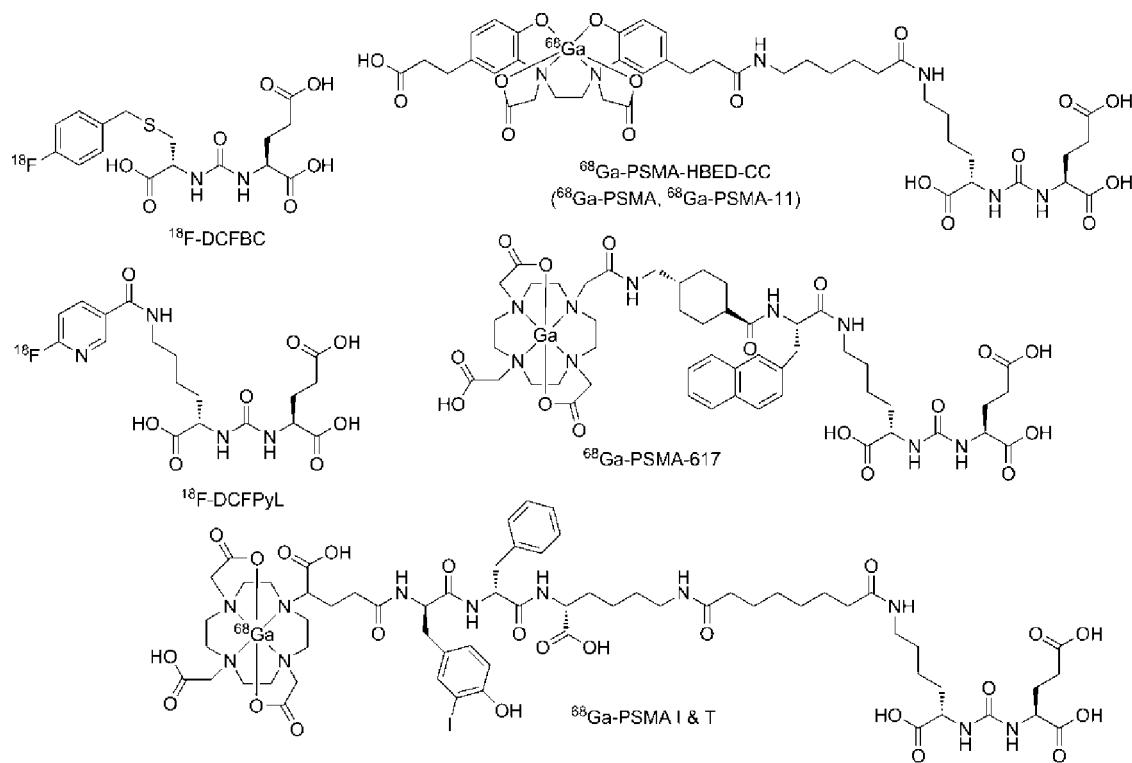
FIG. 1 shows examples of PSMA-targeting tracers used in the clinic for prostate cancer imaging.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

I. General Definitions

Any terms not directly defined herein shall be understood to have the meanings commonly associated with them as understood within the art of the invention. Certain terms are discussed below, or elsewhere in the specification, to provide additional guidance to the practitioner in describing the compounds, compositions, uses, methods and other embodiments of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it may be explicitly stated. Use of examples in the specification, including examples of terms, may be for illustrative purposes only and does not limit the scope and meaning of the embodiments of the invention herein.

As used herein, the terms "comprising," "having", "including" and "containing," and grammatical variations thereof, are inclusive or open-ended and do not exclude additional, non-recited elements and/or method steps. The term "consisting essentially of" if used herein in connection with a composition, use or method, denotes that additional elements and/or method steps may be present, but that these additions do not materially affect the manner in which the recited composition, method or use functions. The term "consisting of" when used herein in connection with a composition, use or method, excludes the presence of additional elements and/or method steps. A composition, use or method described herein as comprising certain elements and/or steps may also, in certain embodiments, consist essentially of those elements and/or steps, and in other embodiments consist of those elements and/or steps, whether or not these embodiments are specifically referred to. A use or method described herein as comprising certain elements and/or steps may also, in certain embodiments, consist essentially of those elements and/or steps, and in other embodiments, consist of those elements and/or steps, whether or not these embodiments are specifically referred to.

A reference to an element by the indefinite article "a" does not exclude the possibility that more than one of the elements is present, unless the context clearly requires that there be one and only one of the elements. The singular forms "a", "an", and "the" include plural referents unless the content clearly dictates otherwise. The use of the word "a" or "an" when used herein in conjunction with the term "comprising" may mean "one," but it is also consistent with the meaning of "one or more," "at least one" and "one or more than one." The term "plurality" if used herein means more than one, for example, two or more, three or more, four or more, and the like.

In this disclosure, the recitation of numerical ranges by endpoints includes all numbers subsumed within that range including all whole numbers, all integers and, where suitable, all fractional intermediates (e.g., 1 to 5 may include 1, 1.5, 2, 2.75, 3, 3.80, 4, and 5 etc.).

Unless otherwise specified, "certain embodiments", "various embodiments", "an embodiment" and similar terms includes the particular feature(s) described for that embodiment either alone or in combination with any other embodiment or embodiments described herein, whether or not the other embodiments are directly or indirectly referenced and regardless of whether the feature or embodiment is described in the context of a compound, method, product, use, composition, et cetera.

The term "subject" refers to an animal (e.g. a mammal or a non-mammal animal). The subject may be a human or a non-human primate. The subject may be a laboratory mammal (e.g., mouse, rat, rabbit, hamster and the like). The subject may be an agricultural animal (e.g., equine, ovine, bovine, porcine, camelid and the like) or a domestic animal (e.g., canine, feline and the like).

The compounds disclosed herein may also include base-free forms, prodrugs, salts or pharmaceutically acceptable salts thereof. Unless otherwise specified, the compounds claimed and described herein are meant to include all racemic mixtures and all individual enantiomers or combinations thereof, whether or not they are explicitly represented herein.

The compounds disclosed herein may be shown as having one or more charged groups (for example, $-R^2BF_3$ is typically shown as zwitterion $-(R^2)^+B^-F_3$) or may be shown with ionizable groups in an uncharged (e.g. protonated) state. As will be appreciated by the person of skill in the art, the ionization state of certain groups within a compound (e.g. without limitation, $CO_2H$, $PO_3H_2$, $SO_2H$, $SO_3H$, $SO_4H$, $OPO_3H_2$ and the like) is dependent, inter alia, on the pKa of that group and the pH at that location. For example, but without limitation, a carboxylic acid group (i.e. COOH) would be understood to usually be deprotonated (and negatively charged) at neutral pH and at most physiological pH values, unless the protonated state is stabilized (e.g. due to intramolecular H-bonding). Likewise, $-OSO_3H$ (i.e. $SO_4H$) groups, $SO_2H$ groups, $SO_3H$ groups, $-OPO_3H_2$ (i.e. $PO_4H_2$) groups and $PO_3H$ groups would generally be deprotonated (and negatively charged) at neutral and physiological pH values.

As used herein, the terms "salt" and "solvate" have their usual meaning in chemistry. As such, when the compound is a salt or solvate, it is associated with a suitable counter-ion. It is well known in the art how to prepare salts or to exchange counter-ions. Generally, such salts can be prepared by reacting free acid forms of these compounds with a stoichiometric amount of a suitable base (e.g. without limitation, Na, Ca, Mg, or K hydroxide, carbonate, bicarbonate, or the like), or by reacting free base forms of these compounds with a stoichiometric amount of a suitable acid. Such reactions are generally carried out in water or in an organic solvent, or in a mixture of the two. Counter-ions may be changed, for example, by ion-exchange techniques such as ion-exchange chromatography. All zwitterions, salts, solvates and counter-ions are intended, unless a particular form is specifically indicated.

In certain embodiments, the salt or counter-ion may be pharmaceutically acceptable, for administration to a subject. More generally, with respect to any pharmaceutical composition disclosed herein, non-limiting examples of suitable excipients include any suitable buffers, stabilizing agents, salts, antioxidants, complexing agents, tonicity agents, cryoprotectants, lyoprotectants, suspending agents, emulsifying agents, antimicrobial agents, preservatives, chelating agents, binding agents, surfactants, wetting agents, non-aqueous vehicles such as fixed oils, or polymers for sustained or controlled release. See, for example, Berge et al. 1977. (J. Pharm Sci. 66:1-19), or Remington—The Science and Practice of Pharmacy, 21st edition (Gennaro et al editors. Lippincott Williams & Wilkins Philadelphia).

As used herein, the expression "Xy-Xz", where y and z are integers (e.g. $X_1$-$X_{15}$, $X_1$-$X_{30}$, $X_1$-$X_{100}$, and the like), refers to the number of carbons (for alkyls and aryls, whether saturated or unsaturated) in a compound, R-group or substituent, or refers to the number of carbons and heteroatoms (for heteroalkyls and heteroaryls, whether saturated or unsaturated) in a compound, R-group or substituent. Heteroatoms may include any, some or all possible heteroatoms. For example, in some embodiments, the heteroatoms are selected from N, O, S, P and Se. In some embodiments, the heteroatoms are selected from N, O, S and P. Such embodiments are non-limiting.

Unless explicitly stated otherwise, the terms "alkyl" and "heteroalkyl" each includes any reasonable combination of the following: (1) saturated alkyls as well as unsaturated alkyls (e.g. alkenyls and alkynyls); (2) linear or branched; (3) acyclic, cyclic (aromatic or nonaromatic) or multi-cyclic (fused rings, multiple non-fused rings or a combination thereof); and (4) unsubstituted or substituted. For example, an alkyl or heteroalkyl (i.e. "alkyl/heteroalkyl") may be saturated, branched and cyclic, or unsaturated, branched and cyclic, or linear and unsaturated, or any other reasonable combination according to the skill of the person of skill in the art. Where the size of the alkyl/heteroalkyl is specified as $X_1$-$X_z$, where z is any integer larger than 1 (e.g. 15, 18, 30, 100 or the like), it will be understood that any cyclic alkyl/heteroalkyl therein comprises at least 3 carbons and heteroatoms so as to form a ring. If unspecified, the size of the alkyl/heteroalkyl is what would be considered reasonable to the person of skill in the art. For example, but without limitation, if unspecified, the size of an alkyl may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100 or more than 100 carbons in length, subject to the common general knowledge of the person of skill in the art. Further, but without limitation, if unspecified, the size of a heteroalkyl may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100 or more than 100 carbons and heteroatoms in length, subject to the common general knowledge of the person of skill in the art.

As used herein, the term "linear" may be used as it is normally understood to a person of skill in the art and generally refers to a chemical entity that comprises a skeleton or main chain that does not split off into more than one contiguous chain. Non-limiting examples of linear alkyls include methyl, ethyl, n-propyl, and n-butyl.

As used herein, the term "branched" may be used as it is normally understood to a person of skill in the art and generally refers to a chemical entity that comprises a skeleton or main chain that splits off into more than one contiguous chain. The portions of the skeleton or main chain that split off in more than one direction may be linear, cyclic or any combination thereof. Non-limiting examples of a branched alkyl group include tert-butyl and isopropyl.

As used herein, the term "saturated" when referring to a chemical entity may be used as it is normally understood to a person of skill in the art and generally refers to a chemical entity that comprises only single bonds. Non-limiting examples of a saturated $C_1$-$C_{15}$ alkyl group may include methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, 1-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl, 3-methylpentyl, sec-hexyl, t-hexyl, n-heptyl, i-heptyl, sec-heptyl, t-heptyl, n-octyl, i-octyl, sec-octyl, t-octyl, n-nonyl, i-nonyl, sec-nonyl, t-nonyl, n-decyl, i-decyl, sec-decyl and t-decyl. Non-limiting examples of $C_2$-$C_{15}$ alkenyl group may include vinyl, allyl, isopropenyl, 1-propene-2-yl, 1-butene-1-yl,1-butene-2-yl,1-butene-3-yl, 2-butene-1-yl, 2-butene-2-yl, octenyl and decenyl. Non-limiting examples of $C_2$-$C_{15}$ alkynyl group may include ethynyl, propynyl, butynyl, pentynyl, hexynyl, heptynyl, octynyl, nonynyl and decynyl. Without limitation, the above-defined saturated $C_1$-$C_{15}$ alkyls, $C_2$-$C_{15}$ alkenyls and $C_2$-$C_{15}$ alkynyls are all encompassed within the term "$X_1$-$X_{15}$ alkyl", as used herein. Without limitation, the term "$X_1$-$X_5$ heteroalkyl" would encompass each of the above-defined saturated $C_1$-$C_{15}$ alkyls, $C_2$-$C_{15}$ alkenyls and $C_2$-$C_{15}$ alkynyls, where one or more of the carbon atoms is independently replaced with a heteroatom. The person of skill in the art would understand that various combinations of different heteroatoms may be used.

Unless explicitly stated otherwise, the terms "aryl" and "heteroaryl" each includes any reasonable combination of the following: (1) cyclic or multi-cyclic (fused rings, multiple non-fused rings or a combination thereof); and (2) aromatic (i.e. unsaturated rings) or nonaromatic (i.e. saturated rings); and (3) unsubstituted or substituted. Non-limiting examples of aryls or heteroaryls (i.e. "aryl/heteroaryl") include: phenyl, naphthyl, thienyl, indolyl, pyridyl and the like. If unspecified, the size of the aryl/heteroaryl is what would be considered reasonable to the person of skill in the art. For example, but without limitation, if unspecified, the size of an aryl may be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100 or more than 100 carbons in length, subject to the common general knowledge of the person of skill in the art. Further, but without limitation, if unspecified, the size of a heteroaryl may be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100 or more than 100 carbons and heteroatoms in length, subject to the common general knowledge of the person of skill in the art. It is noted that an aryl or heteroaryl may have all or only a portion of its skeleton or main chain bonded in such a way so as to form a 'loop', circle or ring of atoms bonded together. That is, the aryl/heteroaryl may comprise linear or branched chains of carbons/heteroatoms that are not part of a ring or loop.

For example, a $X_3$-$X_{18}$ aryl/heteroaryl may include, without limitation, a saturated $C_3$-$C_{18}$ cycloalkyl group, a $C_3$-$C_{18}$ cycloalkenyl group, a $C_3$-$C_{18}$ cycloalkynyl group, a $C_3$-$C_{18}$ aromatic aryl group, a $X_3$-$X_{18}$ non-aromatic heterocyclic group where each X may independently be C, N, S, P, O or Se, and a $X_3$-$X_{18}$ aromatic heterocyclic group where each X may independently be C, N, S, P, O or Se. Non-limiting examples of the saturated $C_3$-$C_{18}$ cycloalkyl group may include cyclopropanyl, cyclobutanyl, cyclopentanyl, cyclohexanyl, cycloheptanyl, cyclooctanyl, cyclononanyl and cyclodecanyl. Non-limiting examples of the $C_3$-$C_{18}$ cycloalkenyl group may include cyclopropenyl, cyclobutenyl, cyclopentenyl, cyclohexenyl, cycloheptenyl, cyclooctenyl, cyclononanenyl and cyclodecanenyl. Non-limiting examples of the $C_3$-$C_{18}$ aromatic aryl group may include phenyl (Ph), pentalenyl, indenyl, naphthyl and azulenyl. Non-limiting examples of the $X_3$-$X_{18}$ non-aromatic heterocyclic group may include aziridinyl, azetidinyl, diazetidinyl, pyrrolidinyl, pyrrolinyl, piperidinyl, piperazinyl, imidazolidinyl, pyrazolidinyl, imidazolydinyl, phthalimidyl, succinimidyl, oxiranyl, tetrahydropyranyl, oxetanyl, dioxanyl, thietanyl, thiepinyl, morpholinyl, and oxathiolanyl. Non-limiting examples of the $X_3$-$X_{18}$ aromatic heterocyclic group may include pyrrolyl, imidazolyl, pyrazolyl, pyridinyl, pyridazinyl, pyrimidinyl, pirazinyl, quinolinyl, isoquinolinyl, acridinyl, indolyl, isoindolyl, indolizinyl, purinyl, carbazolyl, indazolyl, phthalazinyl, naphthyridinyl, quinoxalinyl, quinazolinyl, cinnolinyl, pteridinyl, phenanthridinyl, phenazinyl, phenanthrolinyl, perimidinyl, furyl, dibenzofuryl, xanthenyl, benzofuryl, thiophenyl, thianthrenyl, benzothiophenyl, phosphorinyl, phosphinolinyl, phosphindolyl, thiazolyl, oxazolyl, and isoxazolyl. Unless otherwise specified, $X_1$-$X_{18}$ alkyl/heteroalkyl would encompass, among others, $X_3$-$X_{18}$ aryl/heteroaryl, including the groups defined above.

As used herein, the term "substituted" is used as it would normally be understood to a person of skill in the art and generally refers to a compound or chemical entity that has one chemical group replaced with a different chemical group. Unless otherwise specified, a substituted alkyl may be an alkyl in which one or more hydrogen atom(s) may be/are replaced with one or more atom(s) that may be/are not hydrogen(s). For example, chloromethyl is a non-limiting example of a substituted alkyl, more particularly an example of a substituted methyl. Aminoethyl is another non-limiting example of a substituted alkyl, more particularly an example of a substituted ethyl. Unless otherwise specified, a substituted compound or group (e.g. alkyl, heteroalkyl, aryl, heteroaryl and the like) may be substituted with any chemical group reasonable to the person of skill in the art. For example, but without limitation, a hydrogen bonded to a carbon or heteroatom (e.g. N) may be substituted with halide (e.g. F, I, Br, Cl), amide, oxo, hydroxyl, thiol, phosphate, phosphonate, sulfate, $SO_2H$, $SO_3H$, alkyls, heteroalkyls, aryl, heteroaryl, ketones, carboxaldehyde, carboxylates, carboxamides, nitriles, monohalomethyl, dihalomethyl, trihalomethyl.

As used herein, the term "unsubstituted" is used as it would normally be understood to a person of skill in the art. Non-limiting examples of unsubstituted alkyls include methyl, ethyl, tert-butyl, and pentyl. The expression "optionally substituted" is used interchangeably with the expression "unsubstituted or substituted".

In the structures provided herein, hydrogen may or may not be shown. In some embodiments, hydrogens (whether shown or implicit) may be protium (i.e. $^1H$), deuterium (i.e. $^2H$) or combinations of $^1H$ and $^2H$ evident to the person of skill in the art. Methods for exchanging $^1H$ with $^2H$ are well known in the art. For solvent-exchangeable hydrogens, the exchange of $^1H$ with $^2H$ occurs readily in the presence of a suitable deuterium source, without any catalyst. The use of acid, base or metal catalysts, coupled with conditions of increased temperature and pressure, can facilitate the exchange of non-exchangeable hydrogen atoms, generally resulting in the exchange of all $^1H$ to $^2H$ in a molecule.

Unless otherwise specified, all "$BF_3$" or "$B^-F_3$" groups may comprise three $^{19}F$ at least one $^{18}F$.

II. Compounds

The present disclosure generally relates to a compound comprising a PSMA-binding moiety linked (e.g. through a linker) to a cationic nitrogen proximal to an anionic trifluorinated boron (—$BF_3$ or —$B^-F_3$) to give a zwitterion forming prosthetic group that provides for facile radiolabeling (vide infra).

The PSMA-binding moiety may be any chemical entity that binds PSMA. For example, but without limitation, the PSMA-targeting moiety may be a PSMA inhibitor or ligand (such as urea- or phosphoramidite-based targeting agents, 2-PMPA, and the like) or any other peptidic or non-peptidic PSMA-binding moiety known. The PSMA-binding moiety may be a glutamate-ureido-based ligand of PSMA, e.g. without limitation Glu-urea-Lys, Glu-urea-Ornithine (Glu-urea-Orn), Glu-urea-Gln, Glu-urea-Asn (Zhang et al. 2016 Oncol Lett. 12:1001-1006) and Glu-urea-Lys(AHX) and derivatives thereof, such as Glu-urea-Lys(AHX)-N,N'-bis[2-hydroxy-5-(carboxyethyl)benzyl]ethylenediamine-N,N'-diacetic acid (HBED-CC) (Schafer et al. 2012 EJNMMI Research 2:23).

In some embodiments, the compound comprises $R^2BF_3$ in which $R^2$ comprises the cationic nitrogen.

In some embodiments, $R^2BF_3$ is connected to the PSMA-binding moiety through a linker. The linker may be any linker, e.g. but without limitation, ether, ester, thioether, disulfide, thioester, amide, carbamate, ureido, phosphodiester, polyethylene glycol (PEG), peptide, polypeptide, alkyl (e.g. $X_1$-$X_{100}$ alkyl and the like), heteroalkyl (e.g. $X_1$-$X_{100}$ heteroalkyl and the like), aryl (e.g. $X_3$-$X_{100}$ aryl and the like) or heteroaryl (e.g. $X_3$-$X_{100}$ heteroaryl and the like). The alkyl or heteroalkyl may be one or more of: branched or linear; acyclic, cyclic or multi-cyclic; saturated or unsaturated; and unsubstituted or substituted. The aryl or heteroaryl may be one or more of: cyclic or multi-cyclic; aromatic or nonaromatic; and unsubstituted or substituted. In substituted embodiments, the alkyl, heteroalkyl, aryl or heteroaryl may be substituted with one or more of halide, amide, oxo, hydroxyl, thiol, phosphate and sulfate. In certain embodiments, each X is independently C, N, O, P, Se or S. In certain embodiments, each X is independently C, N, O, P or S. The halide may be —F, —Br, —I or —Cl. In certain embodiments, the halide is —Br, —I or —Cl.

In some embodiments, the $R^2BF_3$ group may be —$N(R^3)_2CH_2BF_3$ wherein each $R^3$ is independently H, methyl, akyl, heteroalkyl, aryl or heteroaryl. In certain embodiments, each $R^3$ is independently: H, methyl, $X_2$-$X_{15}$ akyl, $X_2$-$X_{15}$ heteroalkyl, $X_3$-$X_{15}$ aryl or $X_3$-$X_{15}$ heteroaryl; wherein the $X_2$-$X_{15}$ akyl or the $X_2$-$X_{15}$ heteroalkyl is one or more of: branched or linear; acyclic, cyclic or multi-cyclic; saturated or unsaturated; and optionally substituted with one or more of halide, amide, oxo, hydroxyl, thiol, phosphate and sulfate; wherein the $X_3$-$X_{15}$ aryl or the $X_3$-$X_{15}$ heteroaryl is one or more of: cyclic or multi-cyclic; aromatic or nonaromatic; and unsubstituted or substituted; wherein each X is independently carbon or a heteroatom; and wherein the N in the —$N(R^3)_2CH_2BF_3$ is linked to the $X_2$-$X_{15}$ akyl, the $X_2$-$X_{15}$ heteroalkyl, the $X_3$-$X_{15}$ aryl or the $X_3$-$X_{15}$ heteroaryl through at least two C atoms in the $X_2$-$X_{15}$ akyl, the $X_2$-$X_{15}$ heteroalkyl, the $X_3$-$X_{15}$ aryl or the $X_3$-$X_{15}$ heteroaryl. In substituted embodiments, the compound is substituted with one or more of halide, amide, oxo, hydroxyl, thiol, phosphate and sulfate. In certain embodiments, each X is independently C, N, O, P, Se or S. In certain embodiments, each X is independently C, N, O, P or S. The halide may be —F, —Br, —I or —Cl. In certain embodiments, the halide is —Br, —I or —Cl.

In some embodiments, the $R^2BF_3$ group may be —$N^-(CH_3)_2CH_2B^-F_3$.

In some embodiments, the $R^2BF_3$ group may be —$N(R^3)_2C(R^{10})_2BF_3$ wherein each $R^3$ is as defined above and each $R^{10}$ is independently H, methyl, ethyl, akyl, heteroalkyl, aryl or heteroaryl.

The $R^2BF_3$ group may form a pyridinium group that is C-substituted with —$B^-F_3$ or N-substituted with —$CH_2B^-F_3$, wherein the pyridinium group is unsubstituted or substituted. In certain embodiments, the pyridinium group is substituted with one or more halogens, methyl groups, aryl groups, branched or linear alkyl groups, hydroxyls, esters, thiols, thioethers, amines, ketones, carboxaldehyde, carboxylates, carboxamides, nitriles, monohalomethyl groups, dihalomethyl groups and trihalomethyl groups.

In some embodiments, the $R^2BF_3$ group may form one of the pyridinium groups in Table 1 (shown below), which may optionally be further substituted. In some embodiments, the $R^2BF_3$ group may form one of the pyridinium groups in Table 2 (shown below), which may optionally be further substituted. In some embodiments, the $R^2BF_3$ group may have Formula III (shown below). Where present, an "R" in the pyridine substituted —OR, —SR, —NR—, —NHR or —$NR_2$ is aryl/heteroaryl (e.g. without limitation, $C_3$-$C_{18}$ aryl or $X_3$-$X_{18}$ heteroaryl, where each X is independently C, N, O, S, P or Se) or branched or linear alkyl/heteralkyl (e.g. without limitation, saturated or unsaturated $C_1$-$C_{15}$ alkyl or saturated or unsaturated $X_1$-$X_{15}$ heteroalkyl, where each X is independently C, N, O, S, P or Se). In some embodiments, the pyridinium ring is otherwise unsubstituted. In some embodiments, the pyridinium ring may be further substituted with one or more of halogens, aryls/heteroaryls (e.g. without limitation, $C_3$-$C_{18}$ aryl or $X_3$-$X_{18}$ heteroaryl, where each X is independently C, N, O, S, P or Se), branched or linear alkyls (e.g. without limitation, saturated or unsaturated $C_1$-$C_{15}$ alkyl or saturated or unsaturated $X_1$-$X_{15}$ heteroalkyl, where each X is independently C, N, O, S, P or Se), ketones, carboxaldehydes, carboxylates, carboxamides, nitriles, monohalomethyl groups, dihalomethyl groups and trihalomethyl groups. In Tables 1 and 2 (and in Formula III), the symbol "

" denotes the position of the linkage between the pyridinium and the PSMA-binding moiety. The presence of an —O—, —S—, —NH— or —NR— between the pyridinium and the "

" indicates that the —O—, —S—, —NH— or —NR— is part of the PSMA-binding moiety or linker between the PSMA-binding moiety and pyridinium group.

TABLE 1

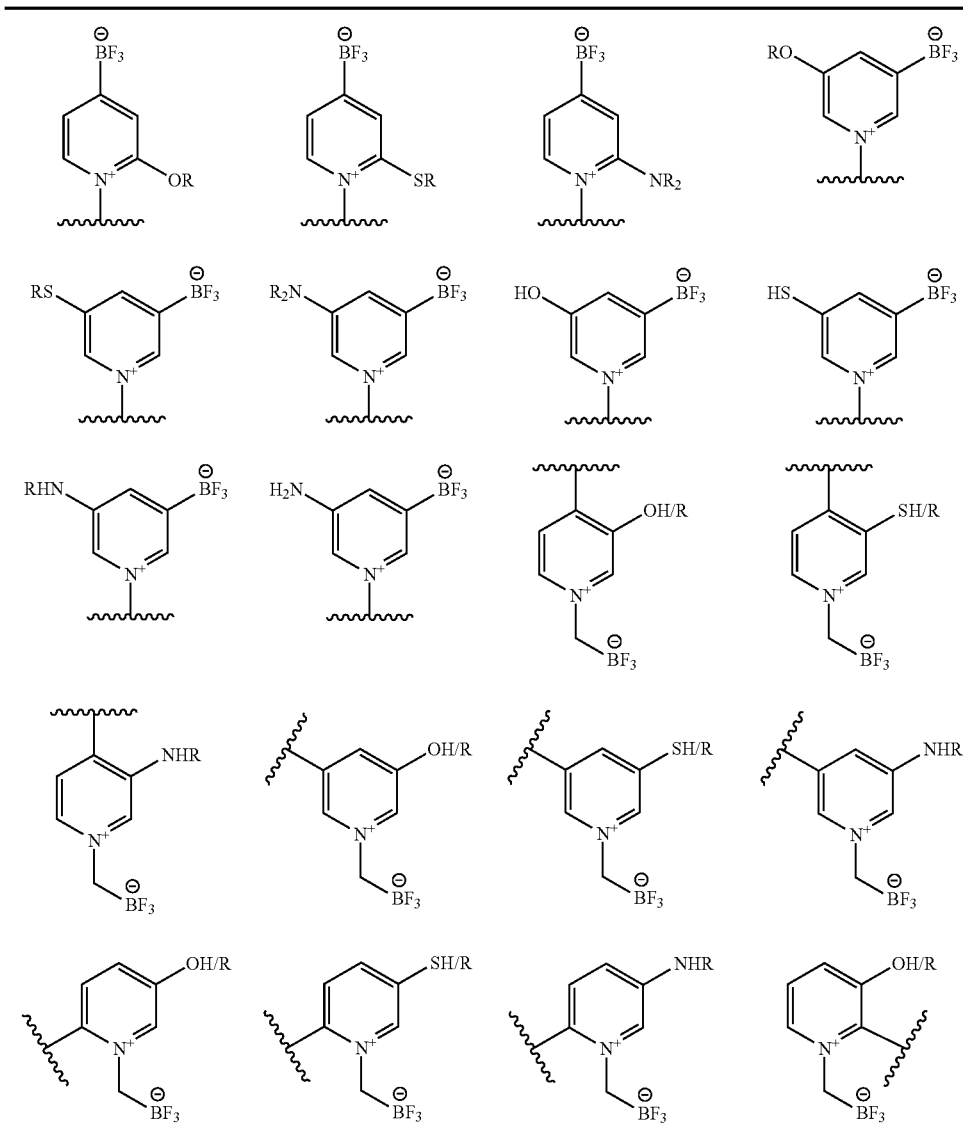

TABLE 1-continued
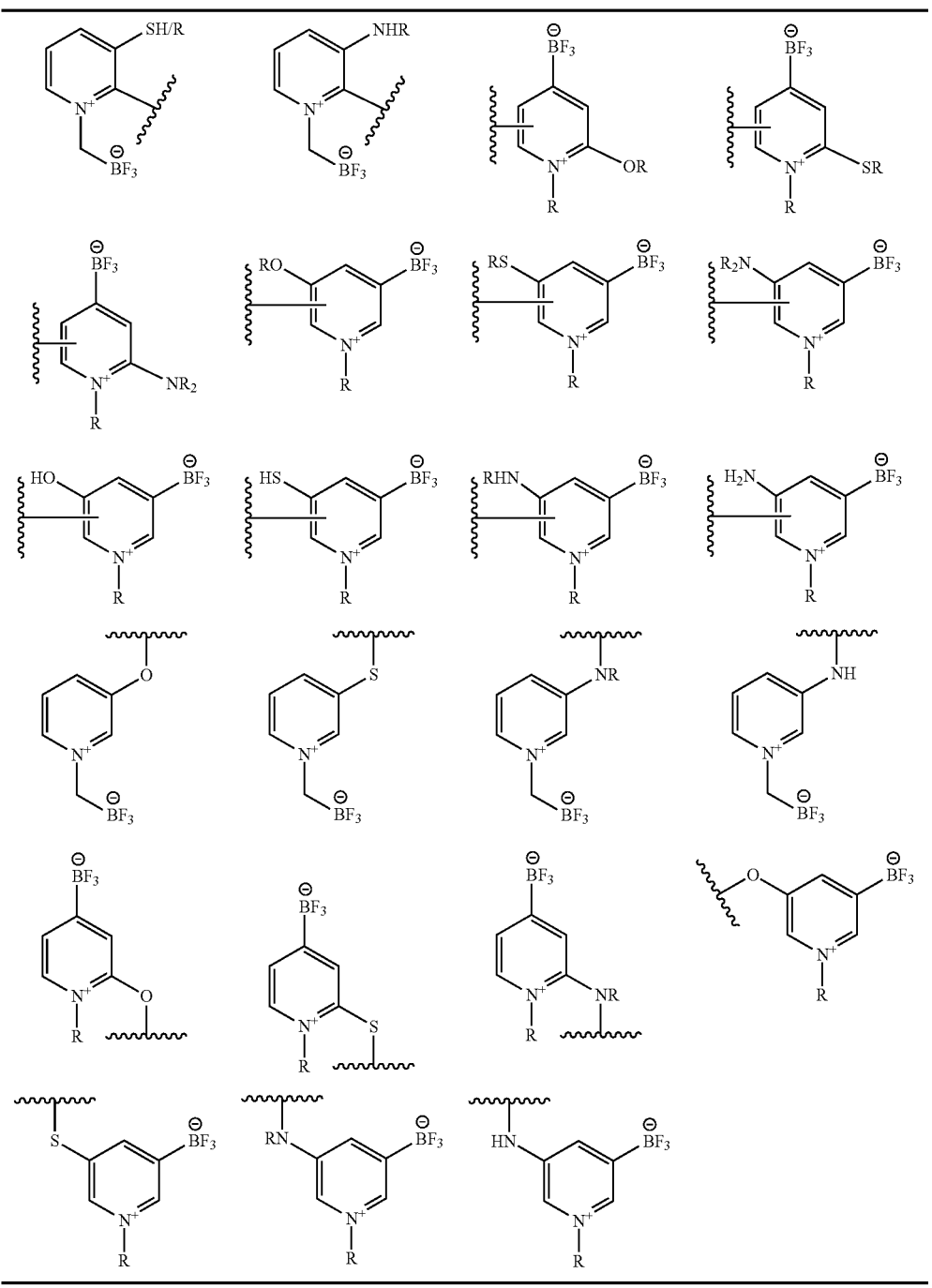
TABLE 2
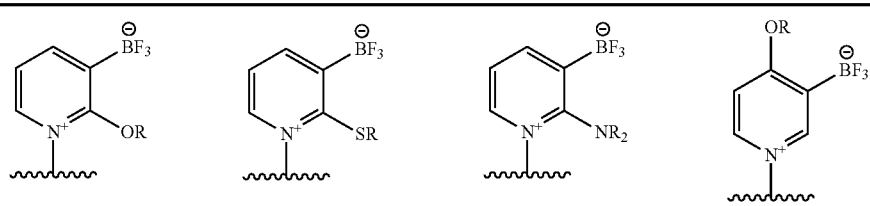

TABLE 2-continued
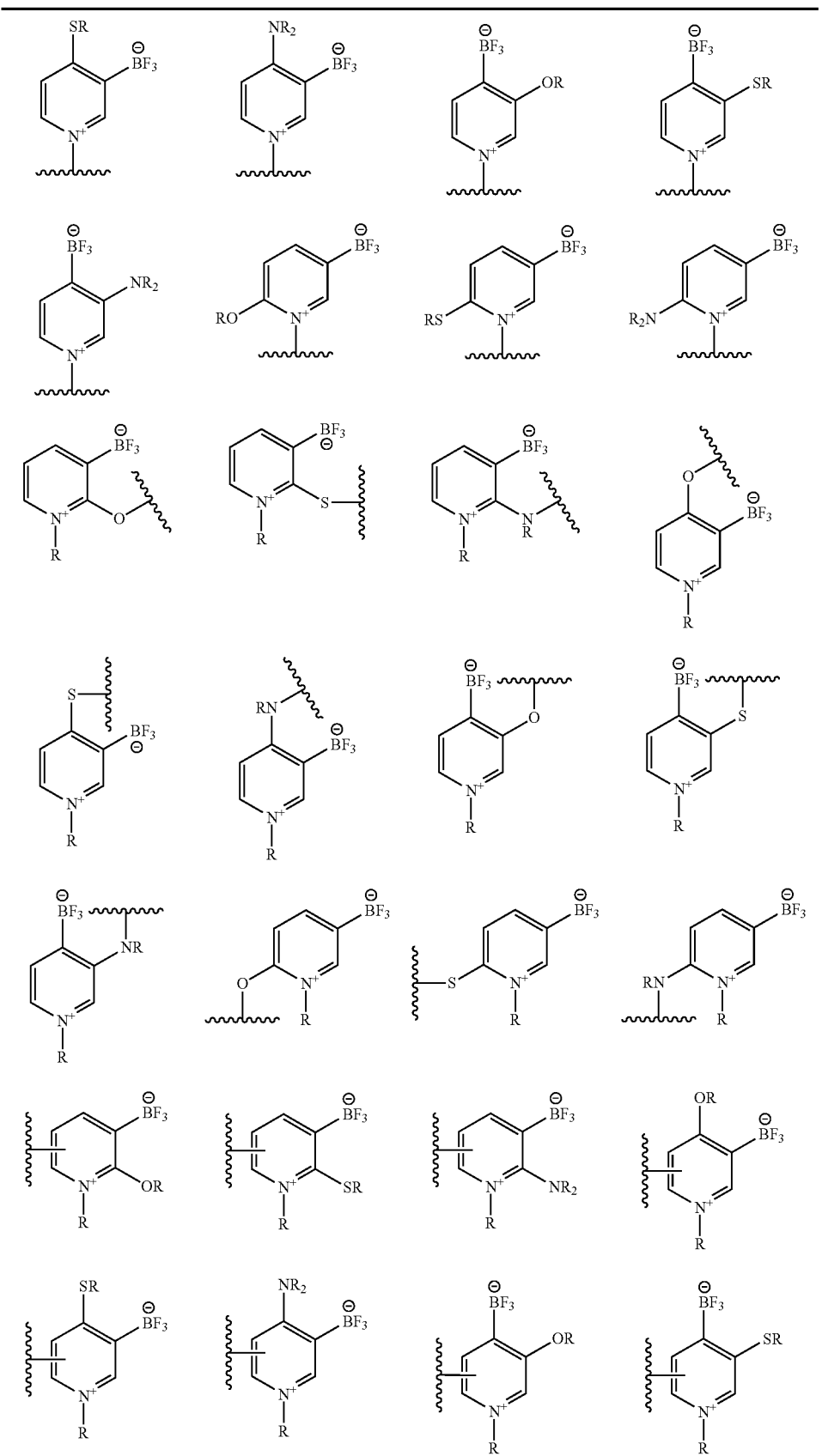

TABLE 2-continued

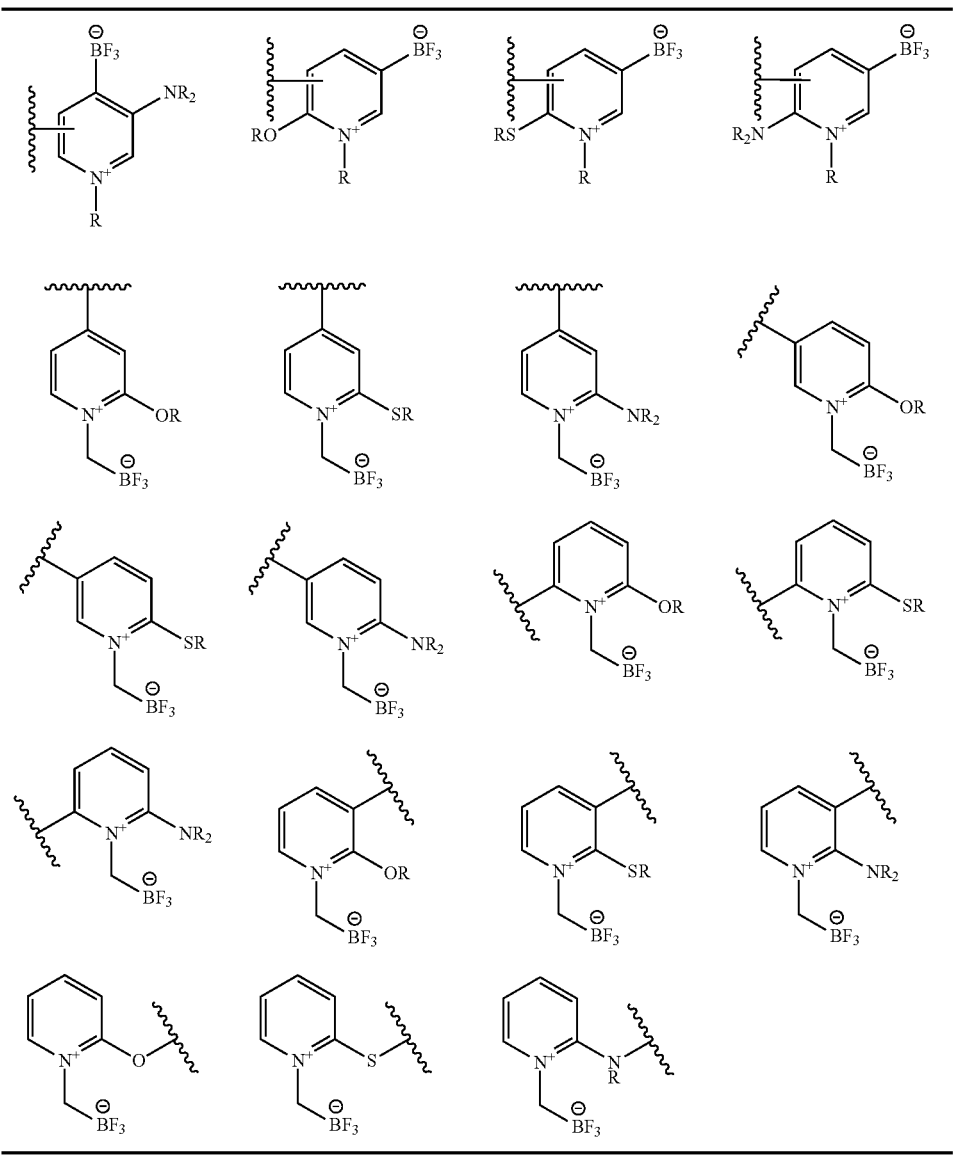

Formula III:

$$\text{(III)}$$

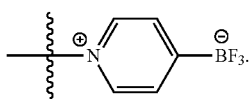

The R²BF₃ group may form an azole N-substituted with —CH₂B⁺F₃. For example, but without limitation, in some embodiments, the R²BF₃ group may form a structure shown in Table 3, wherein the azole ring is optionally further substituted. In Table 3, the symbol "

" denotes the position of the linkage between the azole and the PSMA-binding moiety. In some embodiments, the azole ring is not further substituted. In some embodiments, the azole ring is further substituted with one or more halogens (e.g. one or more of Cl, I and/or Br), alkyls/heteroalkyls (e.g. without limitation, saturated or unsaturated $C_1$-$C_{15}$ alkyl or saturated or unsaturated $X_1$-$X_{15}$ heteroalkyl, where each X is independently C, N, O, S, P or Se), ketones, carboxaldehyde, carboxylates, carboxamides, nitriles, monohalomethyl groups, dihalomethyl groups and trihalomethyl groups. The R-group in Table 3 may be alkyl/heteroalkyl (e.g. without limitation, saturated or unsaturated $C_1$-$C_{15}$ alkyl or saturated or unsaturated $X_1$-$X_{15}$ heteroalkyl, where each X is independently C, N, O, S, P or Se) or aryl/heteroaryl (e.g. without limitation, $C_3$-$C_{18}$ aryl or $X_3$-$X_{18}$ heteroaryl, where each X is independently C, N, O, S, P or Se).

TABLE 3

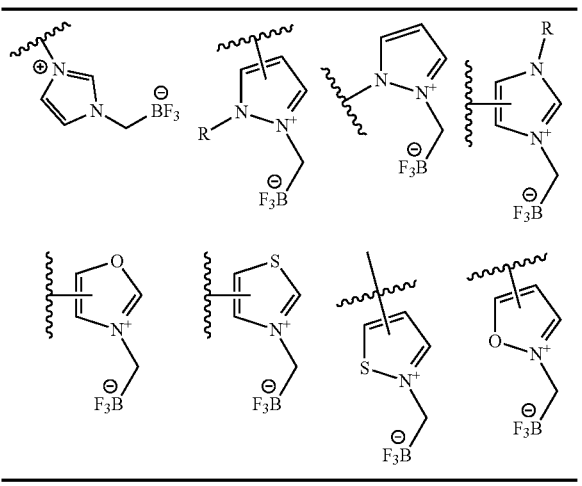

In some embodiments, the compound has Formula I (below) or is a salt or solvate of Formula I. In certain embodiments, the compound has Formula II (below) or is a salt or solvate of Formula II.

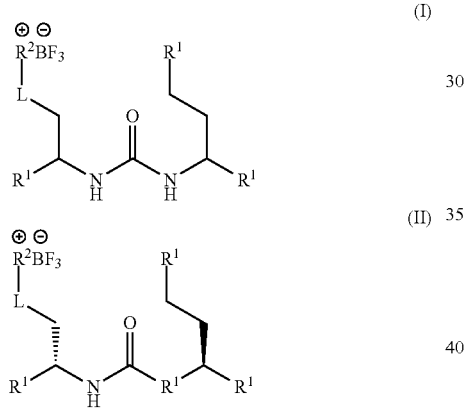

$R^1$ in Formula I or Formula II may be any group which forms an anion at physiological pH, e.g. but without limitation: $CO_2H$, $PO_3H_2$, $SO_2H$, $SO_3H$, $SO_4H$ or $OPO_3H_2$. In certain embodiments, $R^1$ is $CO_2H$ (or $CO_2$).

$R^2BF_3$ in Formula I or Formula II is as defined above.

L in Formula I or Formula II is any linker. In certain embodiments, L is, ether, ester, thioether, disulfide, thioester, amide, carbamate, ureido, phosphodiester, polyethylene glycol (PEG), peptide, polypeptide, alkyl (e.g. $X_1$-$X_{100}$ alkyl and the like), heteroalkyl (e.g. $X_1$-$X_{100}$ heteroalkyl and the like), aryl (e.g. $X_3$-$X_{100}$ aryl and the like) or heteroaryl (e.g. $X_3$-$X_{100}$ heteroaryl and the like). The alkyl or heteroalkyl may be one or more of: branched or linear; acyclic, cyclic or multi-cyclic; saturated or unsaturated; and unsubstituted or substituted. The aryl or heteroaryl may be one or more of: cyclic or multi-cyclic; aromatic or nonaromatic; and unsubstituted or substituted. In substituted embodiments, the alkyl, heteroalkyl, aryl or heteroaryl of L may be substituted with one or more of halide, amide, oxo, hydroxyl, thiol, phosphate and sulfate. In certain embodiments, each X is independently C, N, O, P, Se or S. In certain embodiments, each X is independently C, N, O, P or S. The halide may be —F, —Br, —I or —Cl. In certain embodiments, the halide is —Br, —I or —Cl. In various embodiments, L may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99 or 100 carbons and heteroatoms (if present) in length. L may be more than 100 carbons and heteroatoms (if present) in length.

In certain embodiments, L is $R^4R^5R^6$ in which $R^4$, $R^5$ and $R^6$ together form $X_1$-$X_{100}$ alkyl, $X_1$-$X_{100}$ heteroalkyl, $X_3$-$X_{100}$ aryl or $X_3$-$X_{100}$ heteroaryl, wherein the $X_1$-$X_{100}$ alkyl or the $X_1$-$X_{100}$ heteroalkyl of $R^4R^5R^6$ is one or more of: branched or linear; acyclic, cyclic or multi-cyclic; saturated or unsaturated; and optionally substituted with one or more of halide, amide, oxo, hydroxyl, thiol, phosphate and sulfate; wherein the $X_3$-$X_{15}$ aryl or the $X_3$-$X_{15}$ heteroaryl is one or more of: cyclic or multi-cyclic; aromatic or nonaromatic; and optionally substituted with one or more of halide, amide, oxo, hydroxyl, thiol, phosphate and sulfate; and wherein each X is independently C, N, O, P, S or Se. In certain embodiments, each X is independently C, N, O, P or S.

$R^4$ may be absent, —$CH_2$—, —$CH_2CH_2$— or —$CH_2CH_2CH_2$.

$R^5$ may be —S—, —NHC(O)—, —C(O)—, —C(O)O— or —OC(O)—.

$R^6$ may be (phenyl)$CH_2R^7$, (pyridyl)$CH_2R^7$, or

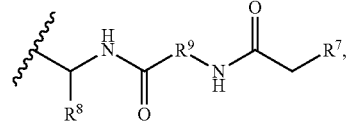

wherein $R^7$ is absent or

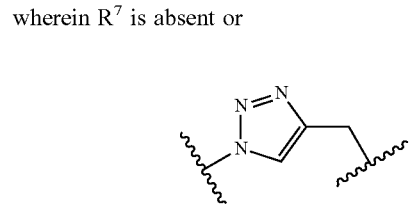

In some embodiments, $R^6$ is

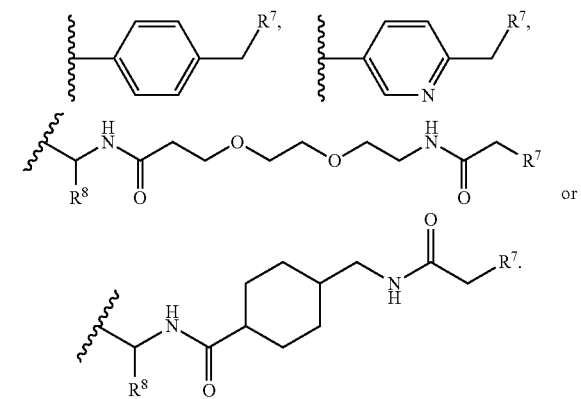

In these structures, the symbol "

" denotes the position of the linkage between $R^6$ and the remainder of the compound.

$R^8$ may be any aliphatic or aromatic hydrophobic side chain of an amino acid whether natural or artificial, or may be any group shown in Table 4, which is unsubstituted, substituted or further substituted (e.g. but without limitation with one or more of halogen, nitro, carboxy, carboxamide, hydroxyl, C1-C4 alkyl, C1-C4 alkoxy, thiol, thioether or cyano groups at any or multiple positions on the ring(s)). In Table 4, the symbol "

" denotes the position of the linkage between $R^8$ and the remainder of the compound.

TABLE 4

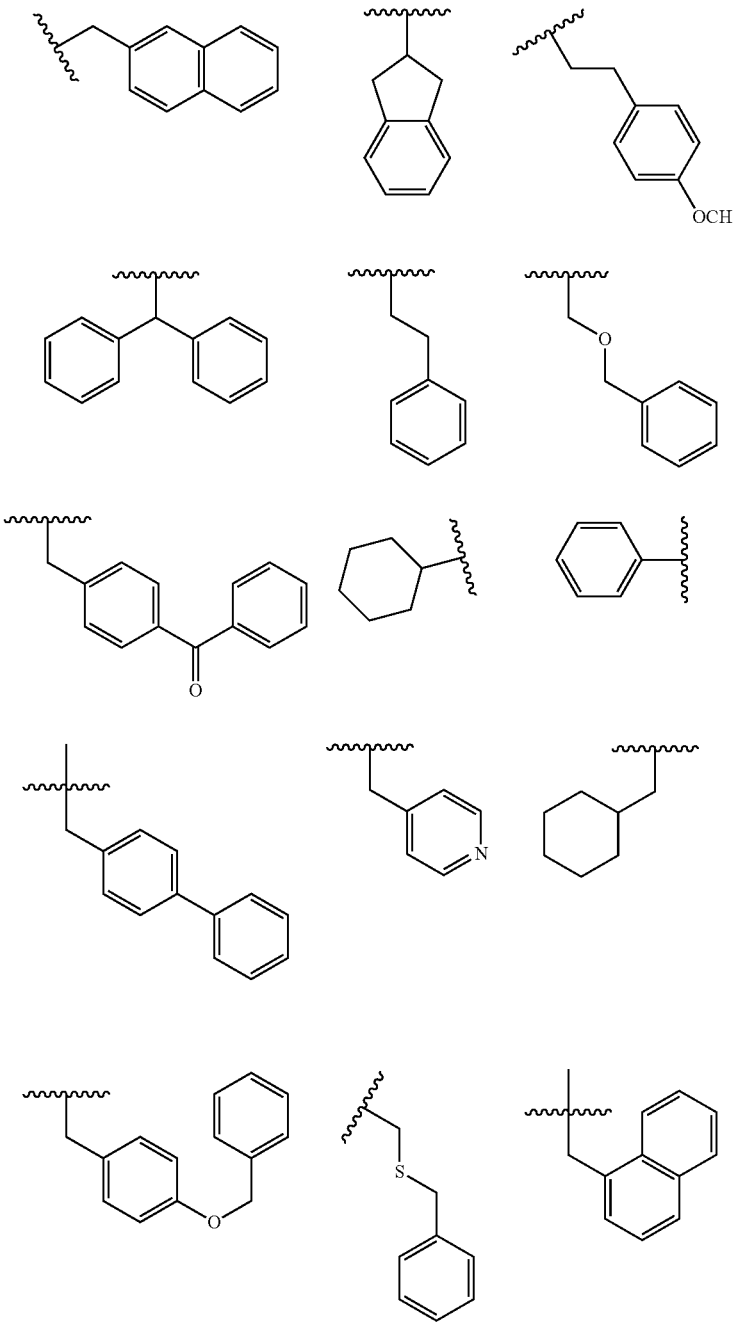

TABLE 4-continued
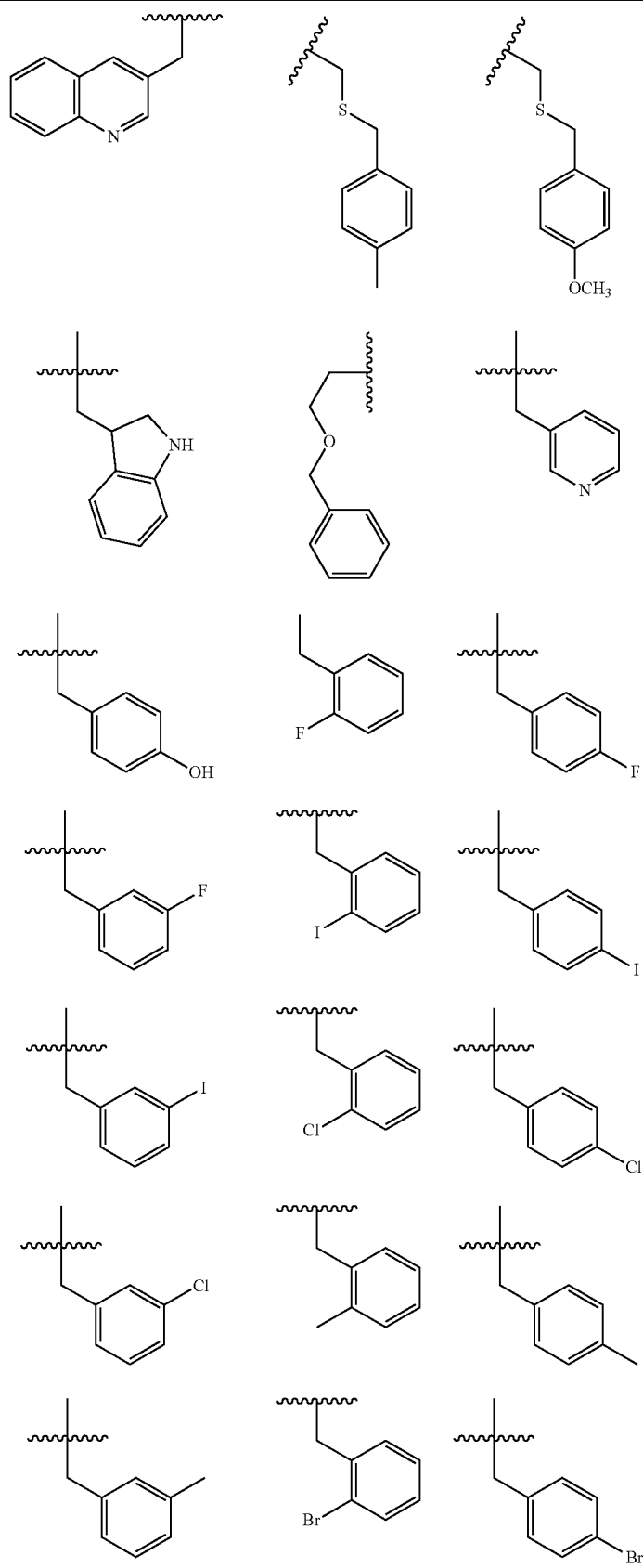

TABLE 4-continued
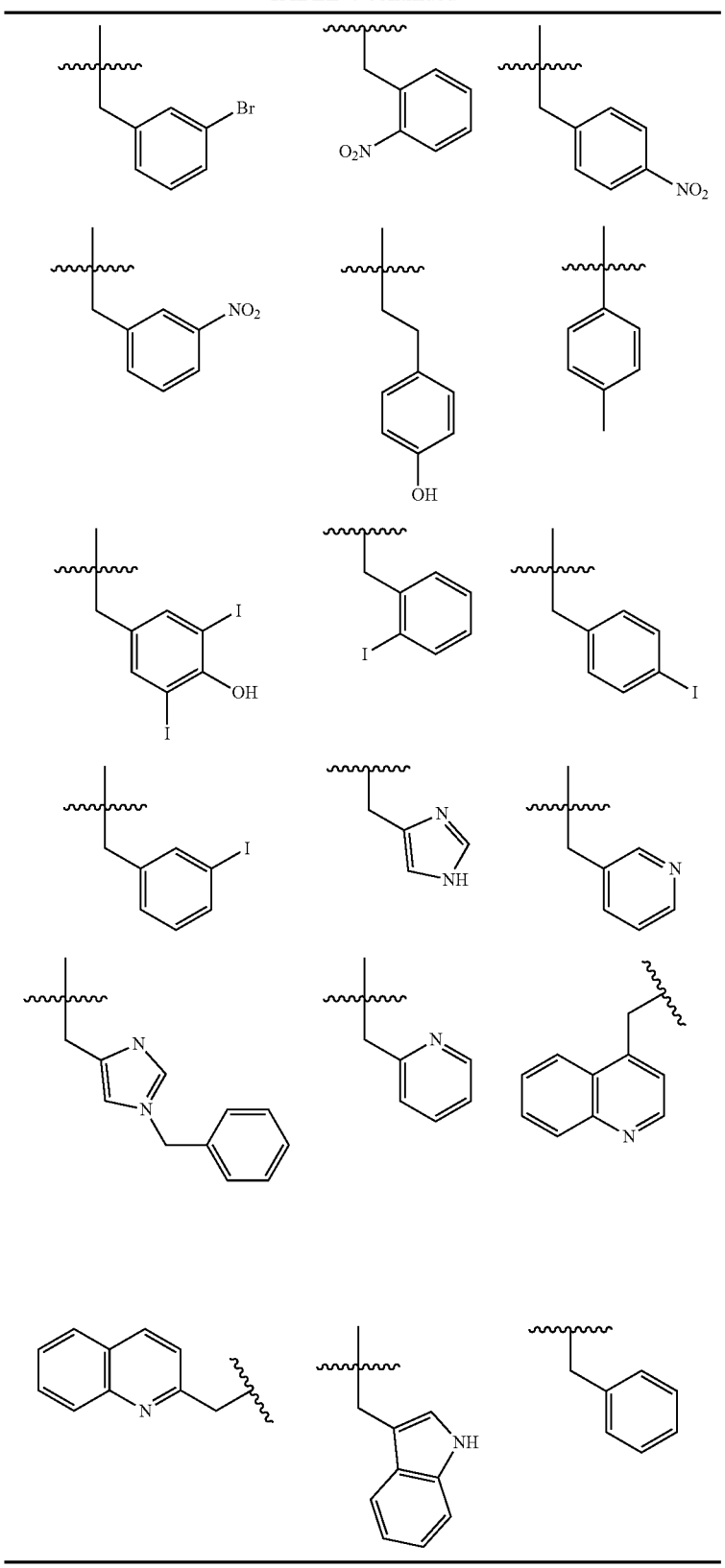
$R^9$ may be an $X_1$-$X_{30}$ alkyl or $X_1$-$X_{30}$ heteroalkyl that is one or more of: branched or linear; acyclic, cyclic or multi-cyclic; saturated or unsaturated; and unsubstituted or substituted (e.g. but without limitation with one or more of halide, amide, oxo, hydroxyl, thiol, phosphate and sulfate); wherein each X is independently C, N, O, P, S or Se.

In some embodiments, the compound is
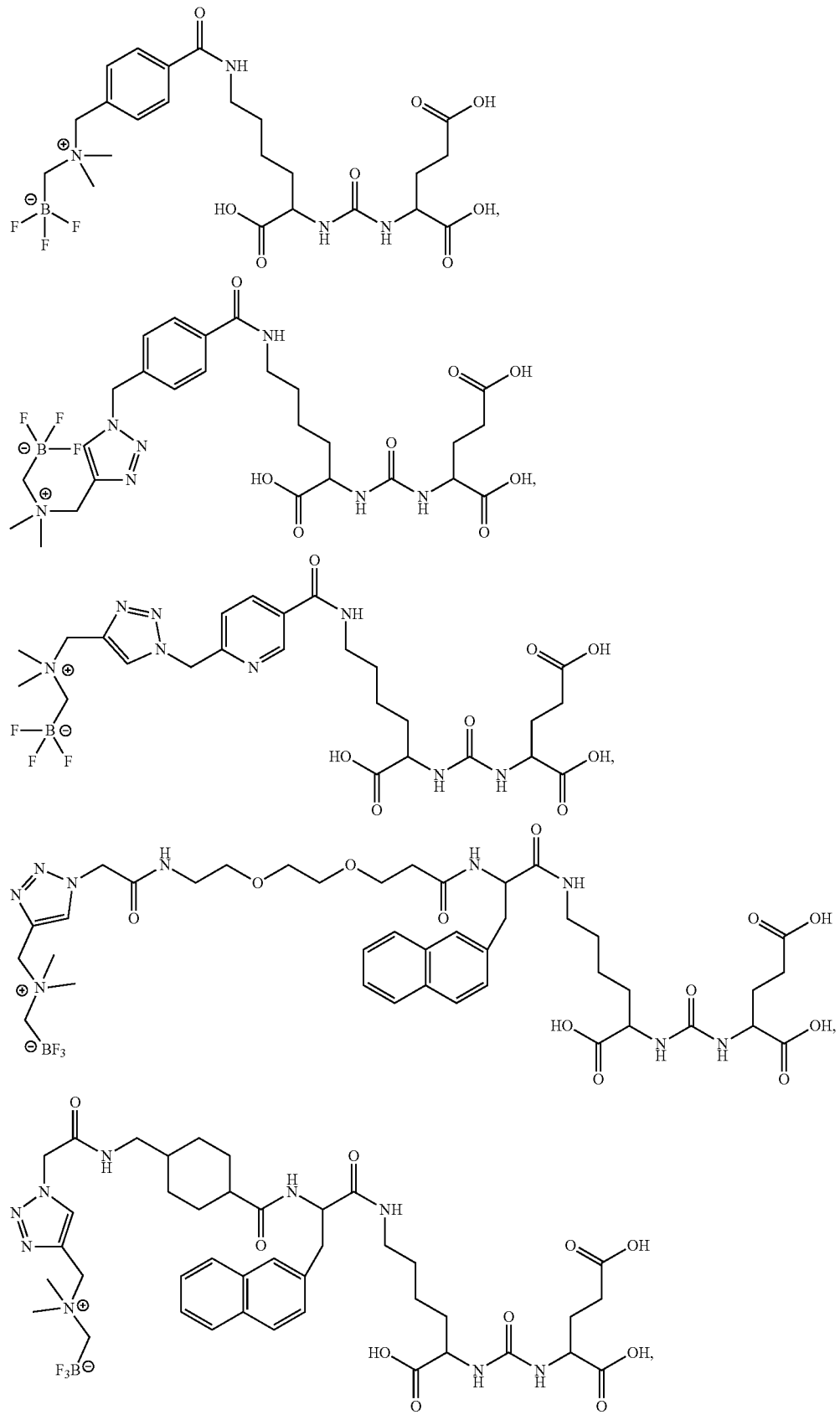

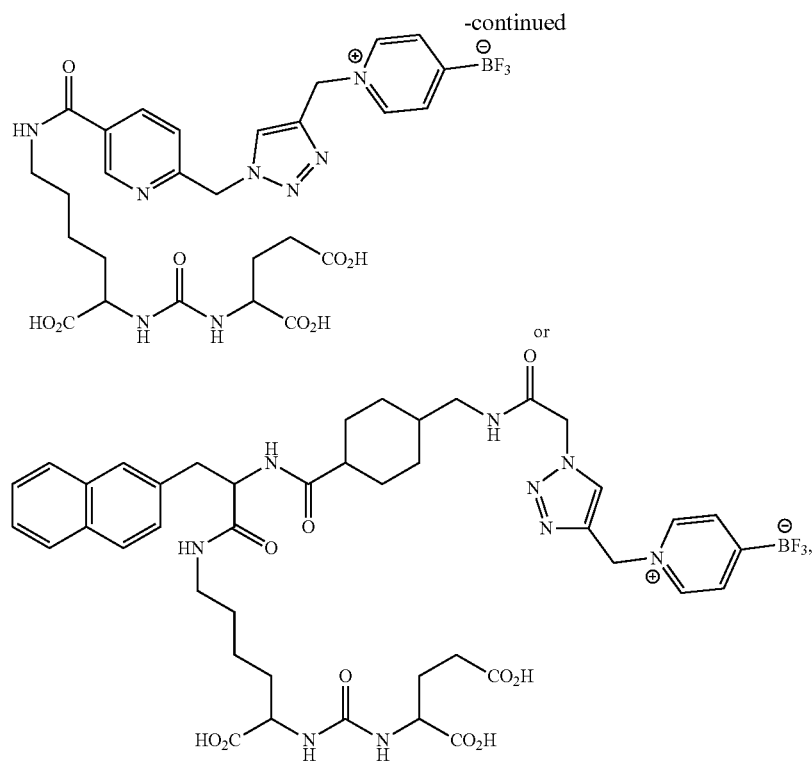
or a salt or solvate thereof.
In some embodiments, the compound is
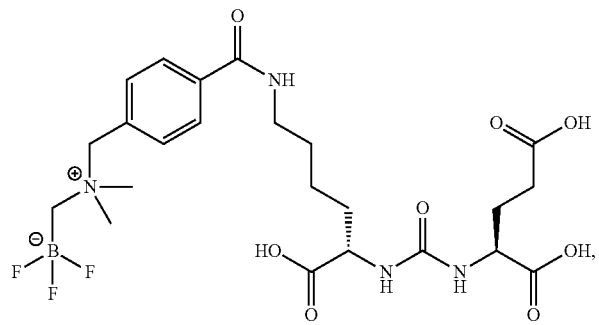
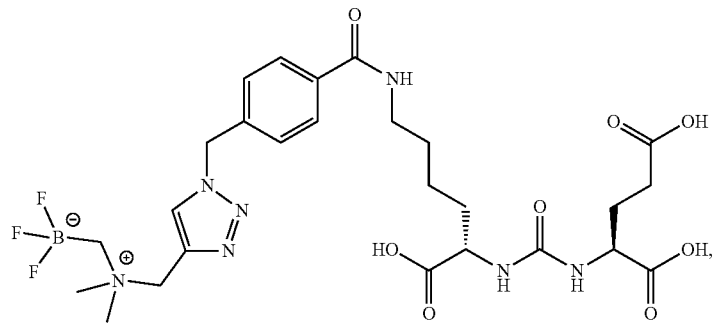

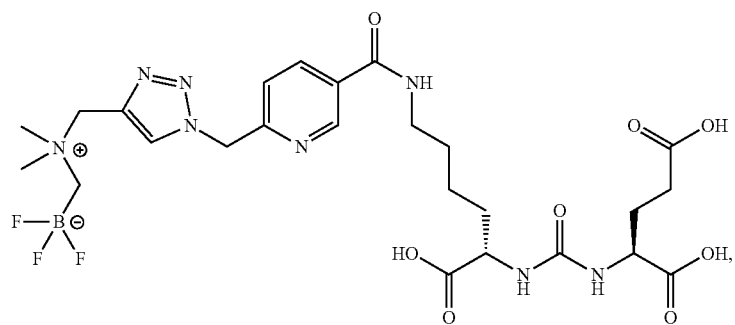
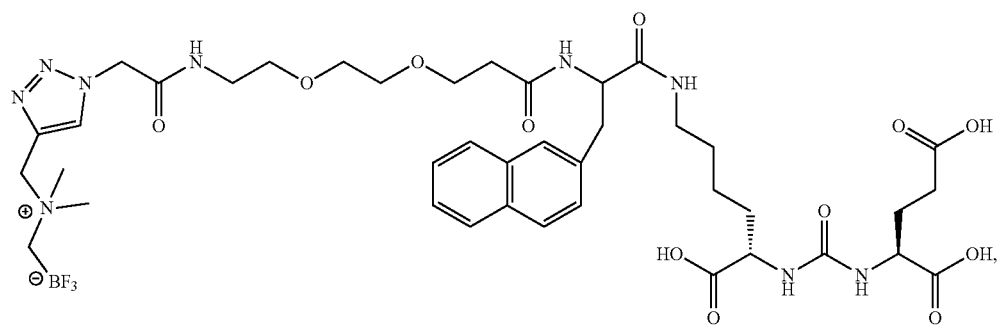
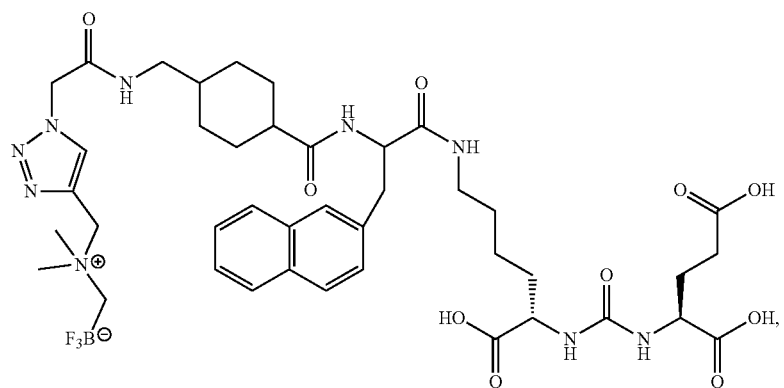
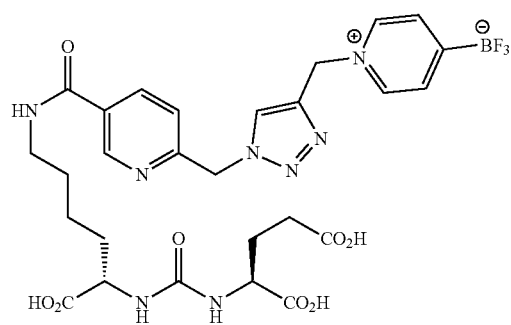
or

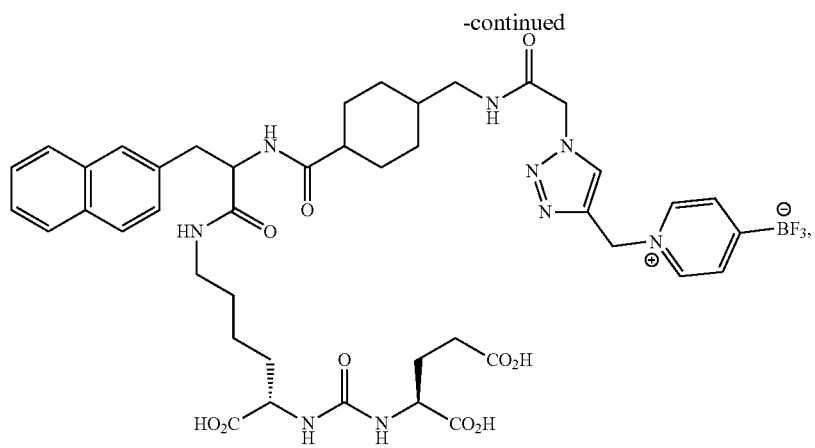

or a salt or solvate thereof.

In some embodiments, at least one fluorine in the —BF$_3$ moiety of the compound is $^{18}$F. As shown in the Examples (below), certain $^{18}$F-labeled compounds were prepared in one-step via a facile $^{18}$F-$^{19}$F isotope exchange reaction on the ammonium-methyl trifluoroborate moiety. Such isotope exchange reaction could be easily implemented for production using a GMP-compliant synthesis module.

III. Uses/Methods

There is also disclosed a pharmaceutical composition comprising the compound as defined in Section II and a pharmaceutically acceptable excipient.

When the compound comprises one or more $^{18}$F atoms bound to the boron atom contained in the —BF$_3$ moiety, the compound and pharmaceutical compositions thereof may, in some embodiments, be used as a $^{18}$F-labeled tracer for imaging PSMA-expressing cells or tissues (e.g. but without limitation for imaging PSMA-expressing cancer in a subject). As shown in the Examples (below) a number of $^{18}$F-labeled compounds were prepared and found suitable for imaging PSMA-expressing cancer.

Accordingly, there is disclosed use of certain embodiments of the compound for preparation of a radiolabelled tracer for imaging PSMA-expressing tissues in a subject. There is also disclosed a method of imaging PSMA-expressing tissues in a subject, in which the method comprises: administering to the subject a composition comprising certain embodiments of the compound and a pharmaceutically acceptable excipient; and imaging tissue of the subject using positron emission tomography (PET). When the tissue is a diseased tissue (e.g. a PSMA-expressing cancer), PSMA-targeted treatment may then be selected for treating the subject.

Regardless of the isotopic distribution of the fluorines in the BF$_3$ moiety of the compound, in certain embodiments the compound (or a pharmaceutical composition thereof) may be used for the treatment of PSMA-expressing diseases (e.g. cancer) in a subject (e.g. due to the inhibition of PSMA). Accordingly, there is provided use of the compound in preparation of a medicament for treating PSMA-expressing disease in a subject. There is also provided a method of treating PSMA-expressing disease in a subject, in which the method comprises: administering to the subject a composition comprising the compound and a pharmaceutically acceptable excipient. For example, but without limitation, the disease may be a PSMA-expressing cancer.

PSMA expression has been detected in various cancers (e.g. Rowe et al., 2015, Annals of Nuclear Medicine 29:877-882; Sathekge et al., 2015, Eur J Nucl Med Mol Imaging 42:1482-1483; Verburg et al., 2015, Eur J Nucl Med Mol Imaging 42:1622-1623; and Pyka et al., J Nucl Med Nov. 19, 2015 jnumed.115.164442). Accordingly, without limitation, the PSMA-expressing cancer may be prostate cancer, renal cancer, breast cancer, thyroid cancer, gastric cancer, colorectal cancer, bladder cancer, pancreatic cancer, lung cancer, liver cancer, brain tumor, melanoma, neuroendocrine tumor, ovarian cancer or sarcoma. In some embodiments, the cancer is prostate cancer.

The present invention will be further illustrated in the following examples.

EXAMPLE 1

Synthesis of HTK-01069

Compound HTK-01069 was prepared according to Schemes 1-3.

Scheme 1 shows the synthesis of intermediate compound HTC-01050:

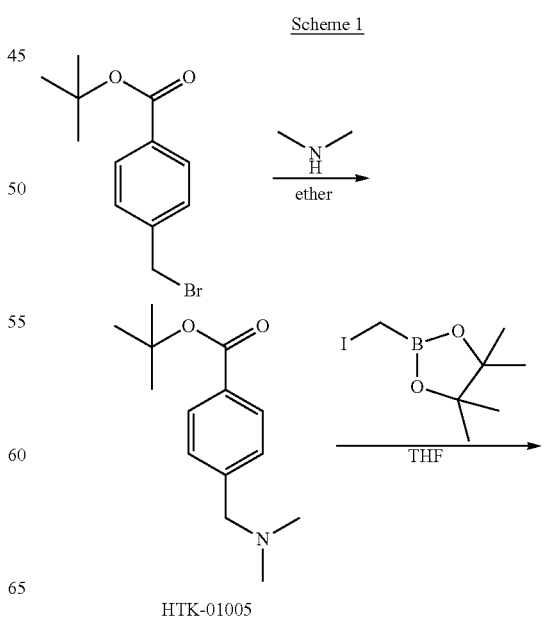

Scheme 1

-continued

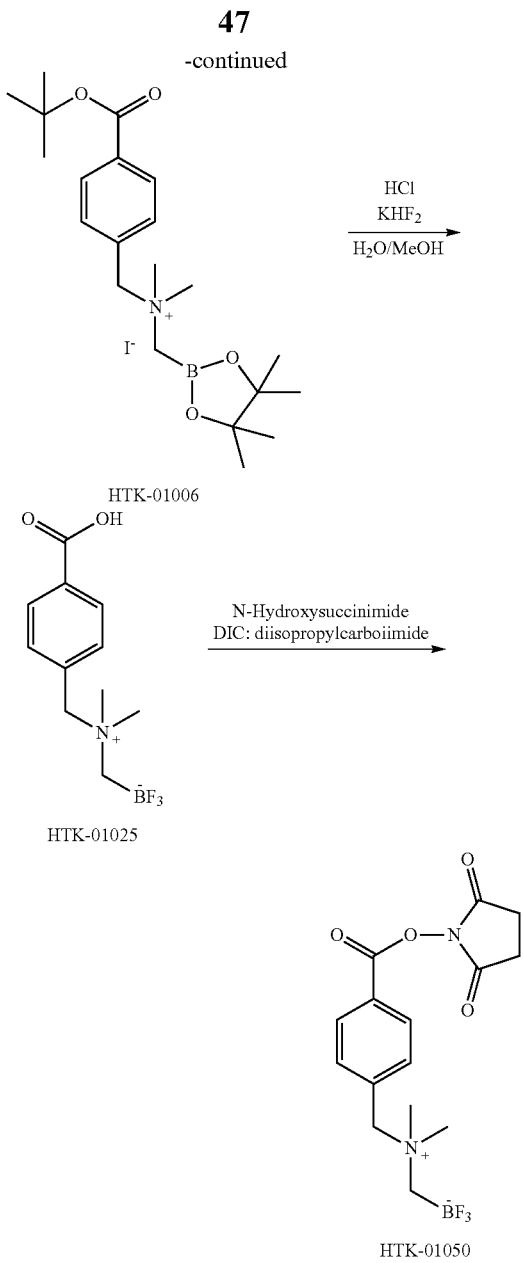

h. The reaction mixture was then concentrated under reduced pressure to obtain brown dense precipitant. The dense precipitant was washed with ether 5 times and dried under vacuum to give crude HTK-01006 as a viscous substance (3.1 g). The crude product of HTK-01006 was used in next step without further purification.

Synthesis of of HTK-01025: The crude product of HTK-01006 (2.5 g, 5.6 mmol) and potassium hydrogen difluoride (5.93 g, 50.4 mmol) were dissolved by $H_2O$ (10 mL) and MeOH (5 mL) in a 50 mL plastic falcon tube. HCl (5 mL, 12 M) was then added to the reaction to give a final concentration of 3 M HCl. The reaction mixture was heated at 60° C. and stirred for 3 days. After warm to room temperature, the reaction mixture was extracted with $CH_2Cl_2$ (50 mL×2). The organic phase was then dried over anhydrous magnesium sulfate and concentrated under reduced pressure. The residue was purified by chromatography on silica gel eluted with 3:7 EtOAc/MeOH to obtain the desired product HTK-01025 as a white solid (247 mg).

Synthesis of of HTK-01050: A solution of HTK-01025 (247 mg, 0.95 mmol), N-hydroxysuccinimide (116.4 mg, 1.01 mmol), and N, N'-diisopropylcarbodiimide (126.2 mg, 1.00 mmol) in DMF (10 mL) was stirred at room temperature for 24 h. The reaction mixture was then concentrated under reduced pressure and dried under vacuum. The product was purified by RP-HPLC using semi-preparative column eluted with 25% acetonitrile at a flow rate of 4.5 mL/min and the retention time was 10.6 minutes. The identity of the white solid product HTK-01050 (50 mg, 15%) was confirmed by ESI mass spectrometry. Calculated for $C_{15}H_{18}BF_3N_2O_4$ $[MNa]^+=381.12$; observed $[MNa]^+=381.09$.

Scheme 2 shows the synthesis of intermediate compound HTK-01068:

Scheme 2

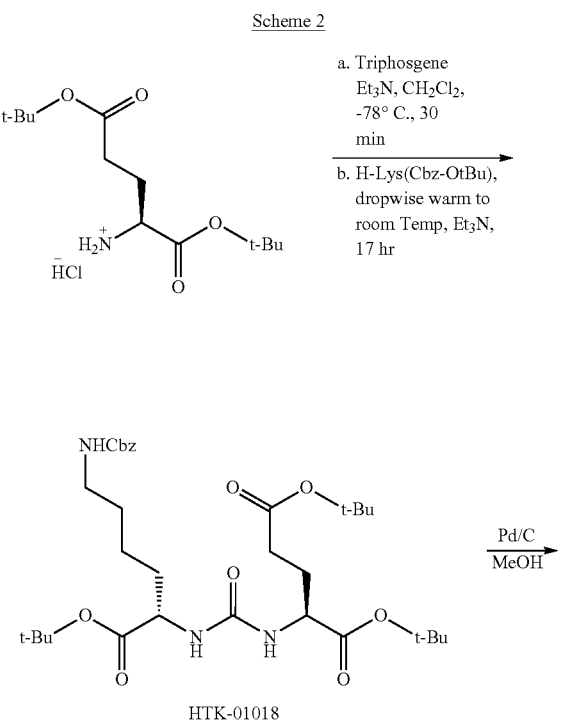

Synthesis of of HTK-01005: A solution of tert-butyl 4-(bromomethyl)benzoate (1.7 g, 6.2 mmol) in ether (6.2 mL, 1M) was added a solution of 40% aqueous dimethylamine (3.9 mL, 31 mmol) solution at room temperature. After stirring for 24 h, the two phase of the reaction mixture were separated by separatory funnel. The organic phase was extracted with 10% citric acid. The combined aqueous extracts were treated with 15% sodium hydroxide. The mixture was extracted with ether and then combined the two parts of organic phases. The organic phase was washed with brine, and then dried over anhydrous magnesium sulfate. The dry organic solution was concentrated under reduced pressure to obtained HTK-01005 as light yellow oil (943 mg, 64.7%). The crude product of HTK-01005 was used in next step without further purification.

Synthesis of of HTK-01006: A solution of crude HTK-01005 (943 mg, 4.0 mmol) and 2-(iodomethyl)-4,4,5,5-tetramethyl-1,3,2-dioxaborolane (1.5 g, 5.6 mmol) in distilled THF (10 mL) was stirred at room temperature for 24

Scheme 3 shows the synthesis of HTK-01069 from intermediates HTK-01050 and HTK-01068:

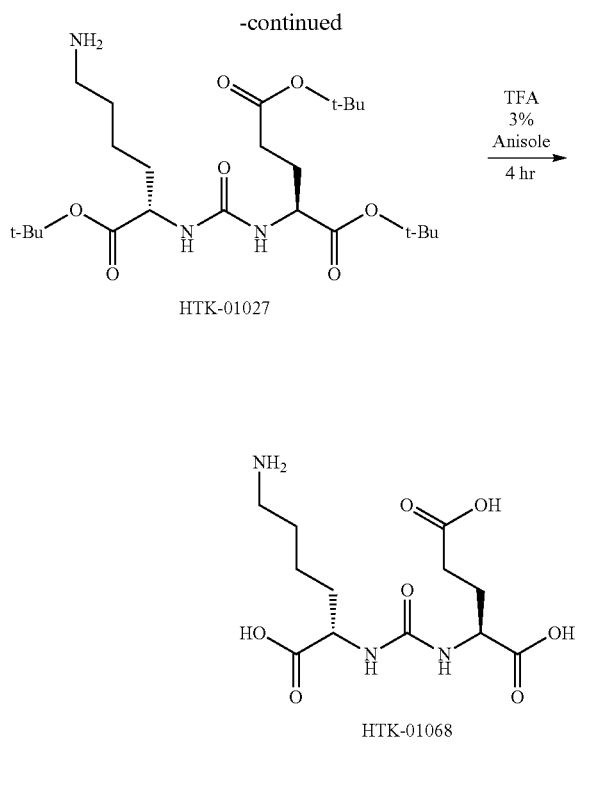

HTK-01027

HTK-01068

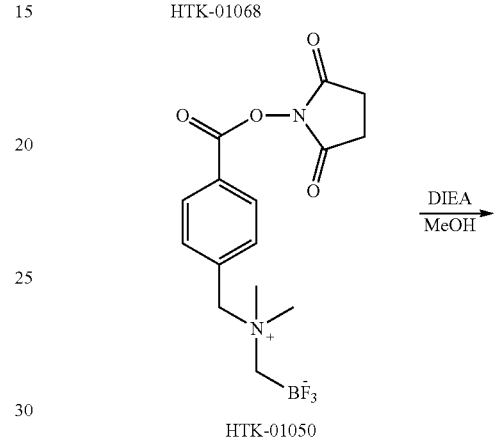

HTK-01050

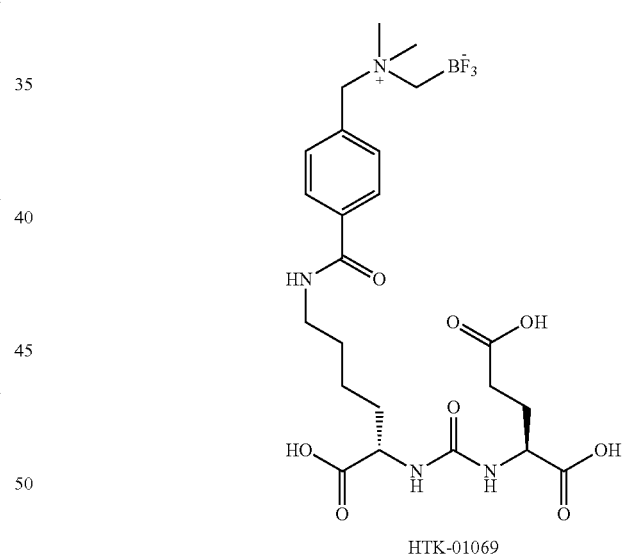

HTK-01069

Synthesis of of HTK-01018: A solution of L-glutamic acid di-tertbutyl ester hydrochloride (1.5 g, 5.07 mmol) and triethylamine (2.31 mL, 16.63 mmol) in $CH_2Cl_2$ (40 mL) was cooled to −78° C. in a dry ice/acetone bath. Triphosgene (525 mg, 1.77 mmol) dissolved in $CH_2Cl_2$ (10 mL) was added dropwise to the reaction. After the addition was complete, the reaction was allowed to warm to room temperature and stirred for 30 minutes. H-Lys(cbz)-OtBu hydrochloride (1.5 g, 4.06 mmol) was then added to the reaction mixture, followed by triethylamine (566 μL, 4.06 mmol). After stirred overnight for 17 h, the reaction mixture was diluted with $CH_2Cl_2$ (50 mL) and washed with $H_2O$ (60 mL×2). The organic phase was then dried over anhydrous magnesium sulfate and concentrated under reduced pressure. The residue was purified by chromatography on silica gel eluted with 3:2 hexane/EtOAc to obtain the desired product HTK-01018 as colorless oil (2.32 g, 92.3%).

Synthesis of of HTK-01027: A solution of HTK-01018 (2.32 g, 4.47 mmol) in MeOH (45 mL) was slowly added Pd/C (117 mg, wet by 5·10 mL MeOH) to the reaction. The reaction mixture was hydrogenated at room temperature under 1 atm. After stirred overnight, the solution was filtered through celite and concentrated under reduced pressure to obtain HTK-01027 as viscous oil (1.81 g). The crude product of HTK-01027 was used in next step without further purification.

Synthesis of HTK-01068: A solution of HTK-01027 (203 mg, 0.32 mmol) in TFA (5 mL) followed by 3% anisole was stirred at room temperature. After 4 h, the reaction mixture was concentrated under reduced pressure. The concentrate diluted with water (1 mL) and extracted with hexane (1 mL×3) to remove anisole. The water phase was then iced and lyophilized to obtain crude HTK-01068 as a yellow oil. The crude product of HTK-01068 was used in next step without further purification.

Synthesis of of HTK-01069: HTK-01068 (38.8 mg, 0.122 mmol) and HTK-01050 (26 mg, 0.073 mmol) was dissolved in MeOH (3 mL) followed by diisopropylethylamine (312 μL, 1.792 mmol). The reaction mixture was heated at 50° C. and stirred for 3 days and then concentrated under reduced pressure. The product was purified by RP-HPLC using semi-preparative column eluted with 15-35% acetonitrile with 0.5% acetic acid at a flow rate of 4.5 mL/min and the retention time was 10.0 minutes. The identity of the white solid product HTK-01069 (13 mg, 32%) was confirmed by ESI mass spectrometry. Calculated for $C_{23}H_{34}BF_3N_4O_8$ $[MH]^+$=563.25; observed $[MH]^+$=563.38.

EXAMPLE 2

Synthesis of HTK-01070

Schemes 4 and 5 show the synthesis of HTK-01070. Scheme 4 shows the synthesis of intermediate compound LIN-03097. Scheme 5 shows the synthesis of HTK-01070 from intermediate compounds HTK-01027 (described above) and LIN-03097.

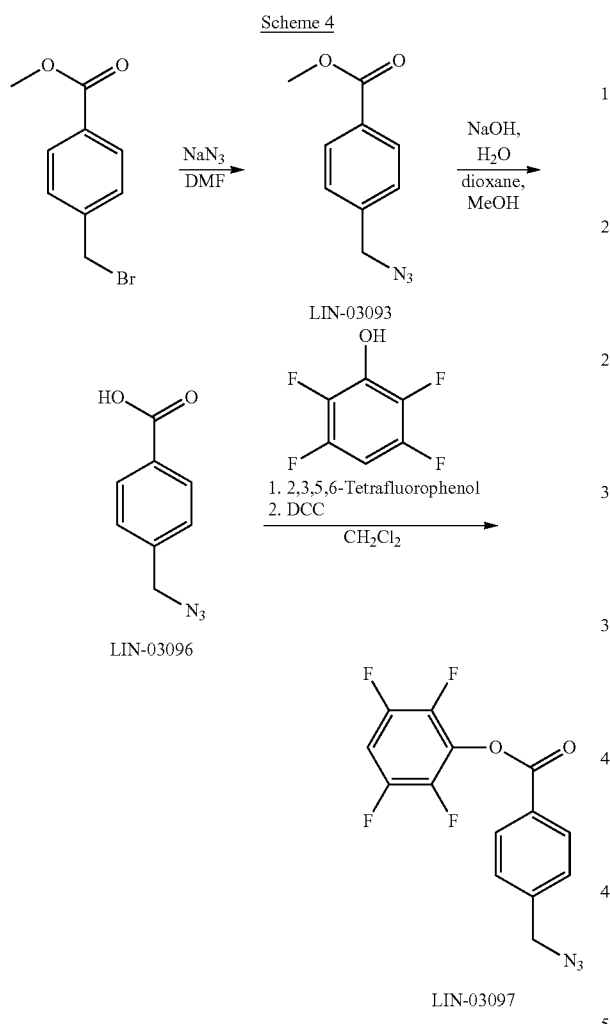

Synthesis of LIN-03093: A solution of methyl 4-(bromomethyl)benzoate (1.0 g, 4.37 mmol) and sodium azide (1.14 g, 17.47 mmol) in DMF (10 mL) was heated at 65° C. and stirred. After 24 h, the reaction mixture was diluted with hexane (50 mL) and washed with H$_2$O (50 mL×2). The organic phase was then dried over anhydrous magnesium sulfate and concentrated under reduced pressure to obtain LIN-03093 as colorless oil (781 mg). The crude product of LIN-03093 was used in next step without further purification.

Synthesis of LIN-03096: A solution of LIN-03093 (781 mg, 4.09 mmol) in 1N NaOH (5 mL), dioxane (5 mL), and MeOH (5 mL) was stirred at room temperature. After 2 days, the reaction mixture was diluted with water (20 mL) and washed with ether (30 mL). The aqueous phase was acidified with HCl (conc.) then extracted with CH$_2$Cl$_2$ (50 mL). The organic phase was then dried over anhydrous magnesium sulfate and concentrated under reduced pressure to obtain LIN-03096 as a white solid (719 mg). The crude product of LIN-03096 was used in next step without further purification.

Synthesis of LIN-03097: A solution of LIN-03096 (719 mg, 4.0 mmol) and 2,3,5,6-tetrafluorophenol (731 mg, 4.4 mmol) in CH$_2$Cl$_2$ (20 mL) was cooled to in an ice/water bath. N, N'-dicyclohexylcarbodiimide (743 mg, 3.6 mmol) was then added to the reaction and stirred for 3 h. The reaction mixture was then filtered and dissolved the residues in hexane (100 mL). The result mixture was then filtered again and washed with 1N NaOH. After dried over anhydrous magnesium sulfate, the solution was concentrated under reduced pressure and purified by chromatography on silica gel eluted with 1:5 ether/hexane to obtain the desired product LIN-03097 as a white solid (1.06 g, 82%).

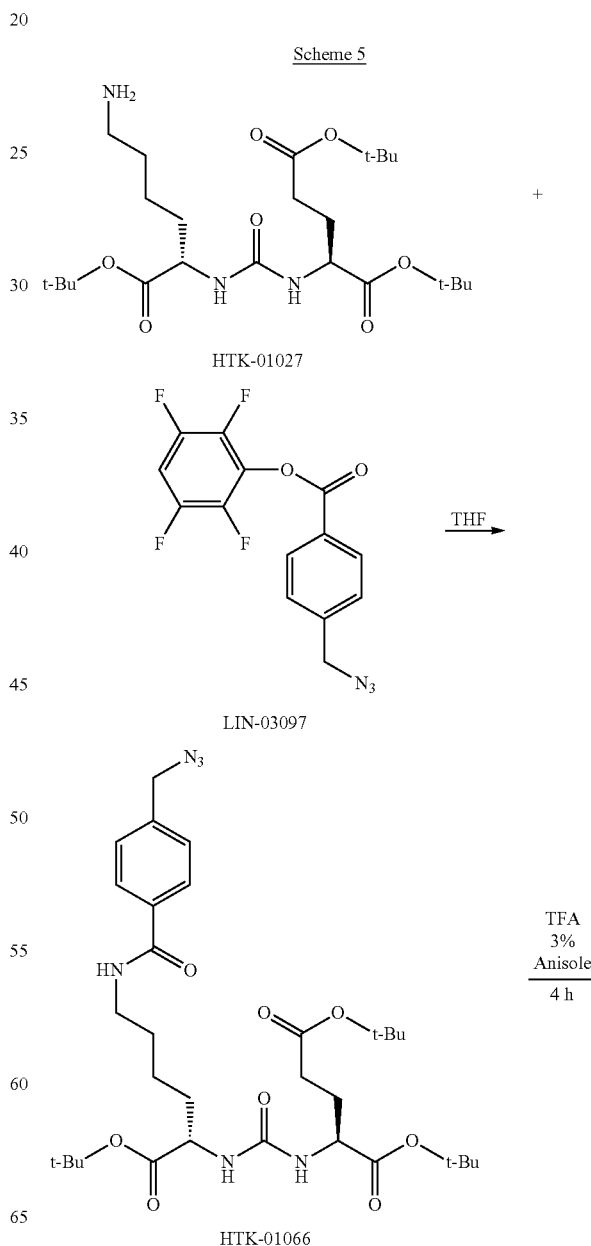

was confirmed by ESI mass spectrometry. Calculated for $C_{26}H_{37}BF_3N_7O_8$ [MH]$^+$=644.28; observed [MH]$^+$=644.44.

EXAMPLE 3

Synthesis of HTK01130

Scheme 6 shows the synthesis of compound HTK01130:

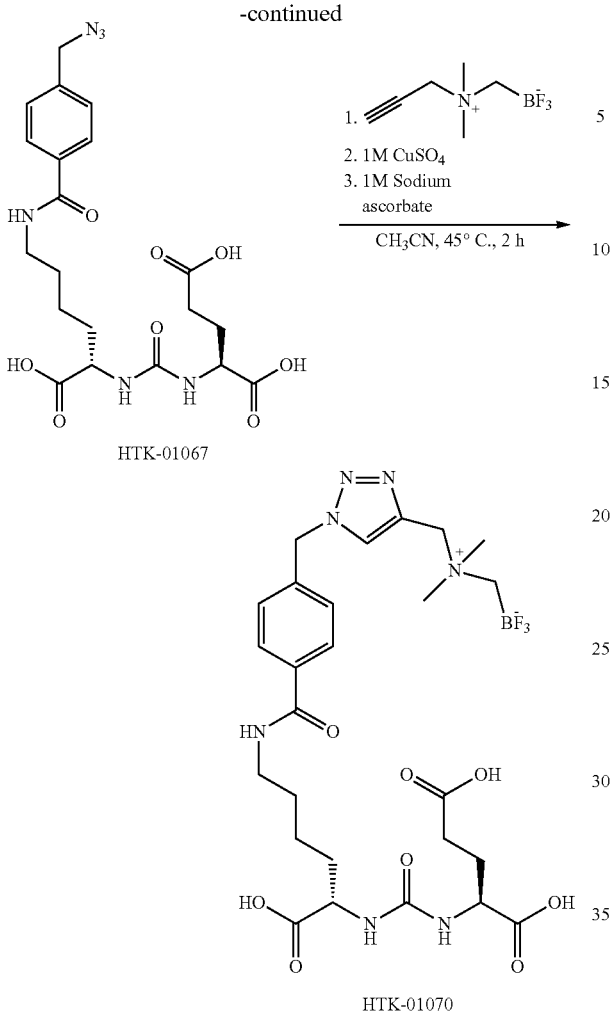

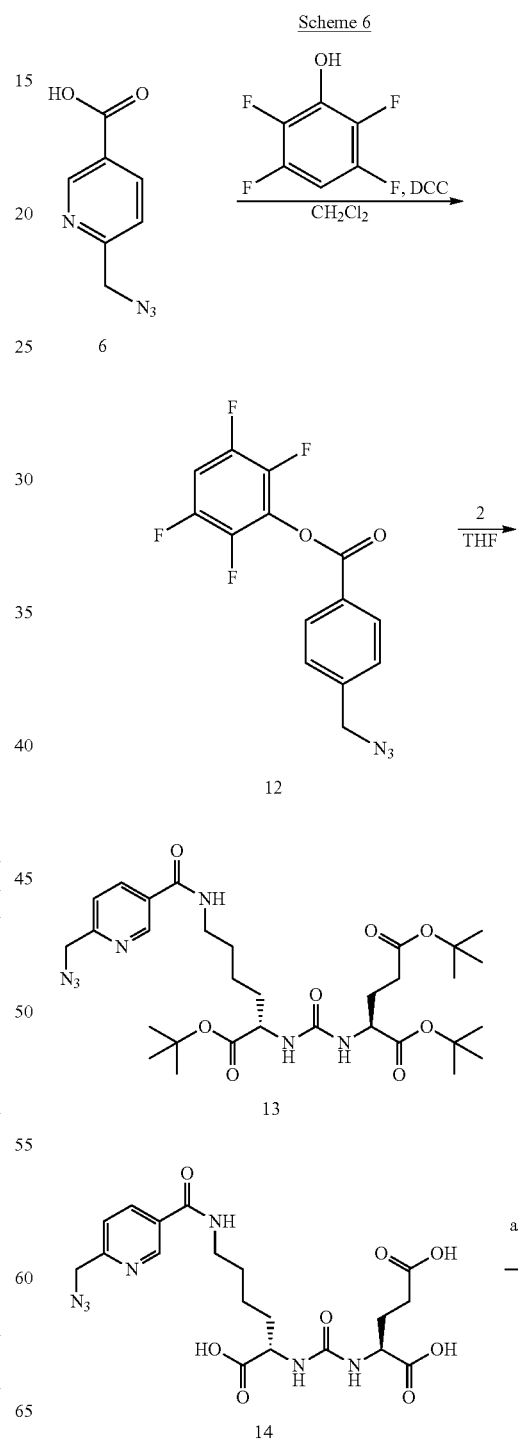

Synthesis of HTK-01066: A solution of HTK-01027 (101.9 mg, 0.21 mmol) and LIN-03097 (100.1 mg, 0.31 mmol) in distilled THF (20 mL) was stirred overnight at room temperature. The reaction mixture was concentrated under reduced pressure and purified by chromatography on silica gel eluted with 1:1 hexane/EtOAc to obtain the desired product HTK-01066 as light yellow oil (120.6 mg, 88.9%).

Synthesis of HTK-01067: A solution of HTK-01066 (98 mg, 0.15 mmol) in TFA (5 mL) followed by 3% anisole was stirred at room temperature. After 4 h, the reaction mixture was concentrated under reduced pressure. The concentrate diluted with water (1 mL) and extracted with hexane (1 mL×3) to remove anisole. The water phase was then iced and lyophilized to obtain crude HTK-01067 as yellow oil. The product was purified by RP-HPLC using semi-preparative column eluted with 25-50% acetonitrile with 0.1% TFA at a flow rate of 4.5 mL/min and the retention time was 10.0 minutes.

Synthesis of HTK-01070: A solution of HTK-01068 (10.5 mg, 0.022 mmol), 1 M CuSO$_4$ (65 μL), and 1 M sodium ascorbate (162.5 μL) in acetonitrile (150 μL) was incubated at 45° C. in sand bath for 2 h. The reaction mixture was purified by RP-HPLC using semi-preparative column eluted with 15-35% acetonitrile with 0.5% acetic acid at a flow rate of 4.5 mL/min and the retention time was 10.4 minutes. The identity of the white solid product HTK-01070 (7 mg, 49%)

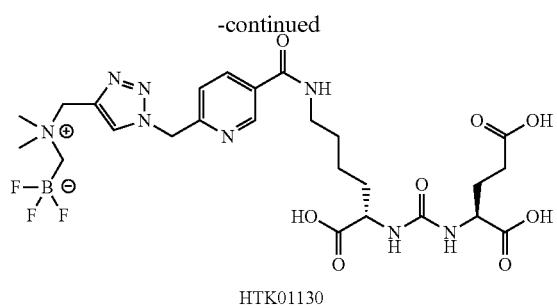

HTK01130

Synthesis of 2,3,5,6-tetrafluorophenyl4-azidomethylnicotinate (12). A solution of 6 (507 mg, 2.8 mmol) and 2,3,5,6-tetrafluorophenol (700 mg, 4.2 mmol) in $CH_2Cl_2$ (20 mL) was cooled in an ice/water bath. N,N'-dicyclohexylcarbodiimide (865 mg, 4.2 mmol) was added to the reaction mixture and stirred for 3 h. The reaction mixture was filtered and the filtrate was concentrated under reduced pressure, and purified by chromatography on silica gel eluted with 1:30 ether/hexane to obtain the desired product 12 as white solid (626.7 mg, 68%). $^1$H NMR (300 MHz, $CDCl_3$): δ9.36 (d, J=2.2 Hz, 1H), δ8.49 (dd, J=8.0, 2.2 Hz, 1H), δ7.57 (d, J=8.0 Hz, 1H), δ7.08 (m, 1H), δ4.64 (s, 2H) MS (ESI): calculated for $C_{13}H_6F_4N_4O_2$ $[MH]^+$=327.05; observed $[MH]^+$=327.30.

Synthesis of (S)-2-[3-[5-(4-azidomethylpicolylamino)-(S)-1-(tert-butoxyloxycarbonyl)pentyl]ureido]pentanedioic acid bis(4-tert-butyl) ester (13). A solution of t-butyl protected Glu-ureido-Lys 2 (141.1 mg, 0.30 mmol) and 12 (118.0 mg, 0.36 mmol) in THF (20 mL) was stirred overnight at room temperature. The reaction mixture was concentrated under reduced pressure and purified by chromatography on silica gel eluted with 2:3 hexane/EtOAc to obtain the desired product 13 as light yellow oil (163.2 mg, 84%). $^1$H NMR (300 MHz, $CDCl_3$): δ9.09 (d, J=1.9 Hz 1H), δ8.26 (dd, J=8.3, 2.2 Hz 1H), δ7.45 (bt, 1H), δ7.43 (d, J=8.3 Hz, 1H), δ5.50 (d, J=7.7 Hz 1H), δ5.32 (d, J=8.0 Hz 1H), δ4.53 (s, 2H), δ4.23 (m, 2H), δ3.57–3.38 (m, 2H), δ2.29 (m, 2H), δ2.20–1.97 (m, 1H), δ1.82–1.76 (m, 2H), δ1.68–1.56 (m, 3H), δ1.43 (s, 18H), δ1.38 (s, 9H). MS (ESI): calculated for $C_{31}H_{49}N_7O_8$ $[MH]^+$=648.37; observed $[MH]^+$=648.60.

Synthesis of HTK01130. A solution of 13 (163.2 mg, 0.15 mmol) in TFA (5 mL) containing 3% anisole was stirred at room temperature. After 4 h, the reaction mixture was concentrated under reduced pressure. The residue was dissolved in water (2 mL) and wash with hexane (2 mL×3) to remove anisole. The aqueous phase was lyophilized to obtain crude 14 as yellow oil (180.2 mg). The crude product (20.0 mg, 0.04 mmol), N-propargyl-N,N-dimethyl-ammoniomethyltrifluoroborate 5 (20.6 mg, 0.13 mmol), 1 M $CuSO_4$ (124 μL), and 1 M sodium ascorbate (310 μL) in acetonitrile (150 μL) and 5% $NH_4OH$ (300 μL) was incubated at 45° C. for 2 h. The reaction mixture was purified by HPLC using semi-preparative column eluted with 3-13% acetonitrile in ammonium formate buffer (40 mM, pH 6.0) at a flow rate of 4.5 mL/min and the retention time was 10.0 minutes. HTK-01130 was obtained as white solid (10.4 mg, 40%). MS (ESI): calculated for $C_{25}H_{36}BF_3N_8O_8$ $[MH]^+$=645.28; observed $[MH]^+$=645.50.

EXAMPLE 4

Synthesis of HTK02066 and HTK02073

Compounds HTK02066 and HTK02073 are shown below:

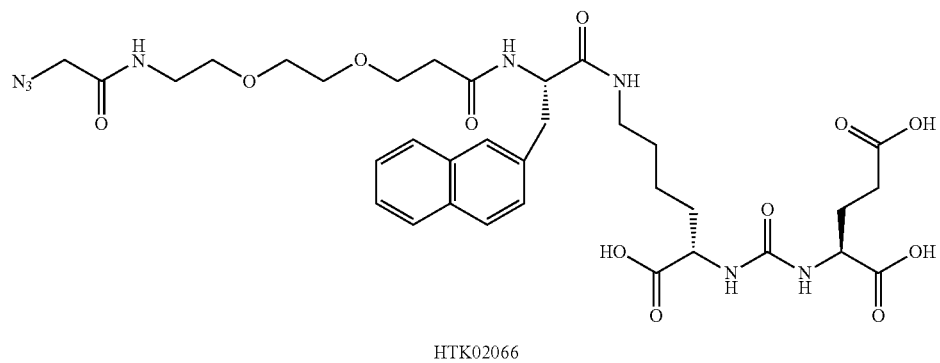

HTK02066

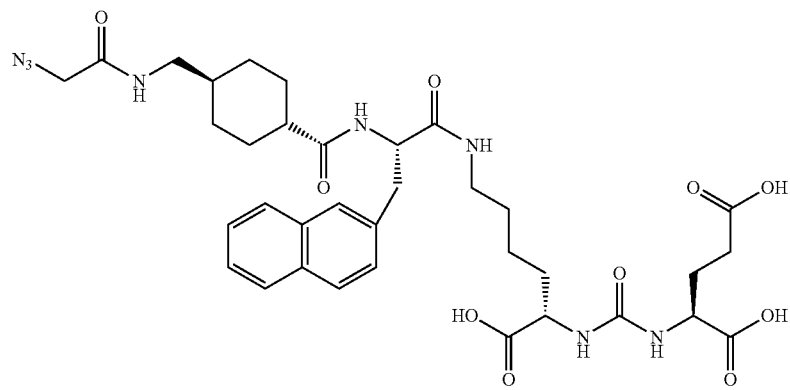

HTK02073

Synthesis of HTK02066. Fmoc was deprotected from Fmoc-Lys(Alloc)-Wang resin followed by adding the isocyanate of the glutamyl moiety (11) and reacted for 16 h to obtain the protected resin bound Glu-ureido-Lys(Alloc). After washing with DMF, the Alloc protecting group was removed by treating with 0.3 equiv of tetrakis(triphenl) palladium in the presence of 1 mL/g (resin) 4-methylmorpholine and 0.5 mL/g (resin) acetic acid in chloroform for 2 h twice. Fmoc-protected 2-NaI and Fmoc-protected dPEG2 were then subsequently coupled onto the Glu(tBu)$_2$-ureido-Lys-Wang resin by solid phase peptide synthesis. After Fmoc deprotection, 2-azidoacetic acid (5 equivalents) was coupled to the N-terminus of dPEG2-HTK02066 sequence with in situ activating reagent N,N'-diisopropylcarbodiimide (5 equivalents) and N-hydroxysuccinimide (6 equivalents). At the end, the peptide was deprotected and simultaneously cleaved from the resin by treating with 95/5 TFA/TIS for 2 h at room temperature. After filtration, the peptide was precipitated by the addition of cold diethyl ether to the TFA solution. The crude peptide was purified by HPLC using the semi-preparative column eluted with 31-40% acetonitrile (0.1% TFA) in water at a flow rate of 4.5 mL/min. The retention time was 9.8 min, and the yield of the peptide HTK02066 was 35.5%. MS (ESI): calculated for $C_{34}H_{46}N_8O_{12}$ [MH]$^+$=759.33; observed [MH]$^+$=759.50.

Synthesis of HTK02073. Fmoc was deprotected from Fmoc-Lys(Alloc)-Wang resin followed by adding the isocyanate of the glutamyl moiety (11) and reacted for 16 h to obtain the protected resin bound Glu-ureido-Lys(Alloc). After washing with DMF, the Alloc protecting group was removed by treating with 0.3 equiv of tetrakis(triphenl) palladium in the presence of 1 mL/g (resin) 4-methylmorpholine and 0.5 mL/g (resin) acetic acid in chloroform for 2 h twice. Fmoc-protected 2-NaI and Fmoc-protected tranexamic acid were then subsequently coupled onto the Glu(tBu)$_2$-ureido-Lys-Wang resin by solid phase peptide synthesis. After Fmoc deprotection, 2-azidoacetic acid (5 equivalents) was coupled to the N-terminus of the sequence with in situ activating reagent N,N'-diisopropylcarbodiimide (5 equivalents) and N-hydroxysuccinimide (6 equivalents). At the end, the peptide was deprotected and simultaneously cleaved from the resin by treating with 95/5 TFA/TIS for 2 h at room temperature. After filtration, the peptide was precipitated by the addition of cold diethyl ether to the TFA solution. The crude peptide was purified by HPLC using the semi-preparative column eluted with 35-45% acetonitrile (0.1% TFA) at a flow rate of 4.5 mL/min. The retention time was 9.1 min, and the yield of the peptide HTK02066 was 25.5%. MS (ESI): calculated for $C_{35}H_{46}N_8O_{10}$ [MH]$^+$=739.80; observed [MH]$^+$=740.26.

EXAMPLE 5

Synthesis of HTK01146 and HTK01157

Compounds HTK01146 and HTK01157 are shown below:

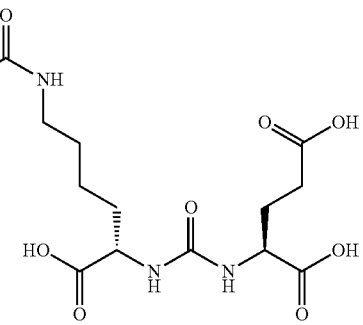

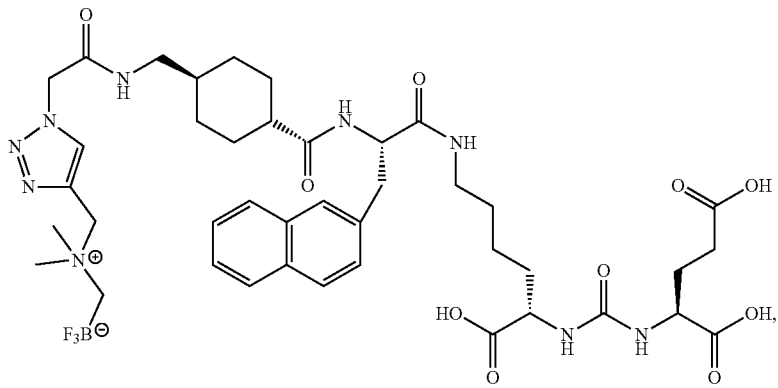

Synthesis of HTK01146. A solution of HTK02066 (10.5 mg, 0.014 mmol), N-propargyl-N,N-dimethyl-ammoniomethyltrifluoroborate (8.0 mg, 48.6 μmol), 1 M CuSO$_4$ (30 μL), and 1 M sodium ascorbate (72 μL) in acetonitrile (100 μL) and 5% NH$_4$OH (100 μL) was incubated at 45° C. oil bath for 2 h. The reaction mixture was purified by HPLC using the semi-preparative column eluted with 20% acetonitrile and 80% ammonia formate buffer (40 mM, pH 6.0) at a flow rate of 4.5 mL/min. The retention time was 7.6 min, and the yield of the peptide was 50.0%. MS (ESI): calculated for $C_{40}H_{57}BF_3N_9O_{12}$ [MNa]$^+$=946.41; observed [MNa]$^+$=946.60.

Synthesis of HTK01157. A solution of HTK02073 (3.8 mg, 5 μmol), N-propargyl-N,N-dimethyl-ammoniomethyltrifluoroborate (4 mg, 24.2 μmol), 1 M CuSO$_4$ (25 μL), and 1 M sodium ascorbate (70 μL) in acetonitrile (150 μL) and 5% NH₄OH (150 μL) was incubated at 45° C. oil bath for 2 h. The reaction mixture was purified by HPLC using the semi-preparative column eluted with 21% acetonitrile and 79% ammonia formate buffer (40 mM, pH 6.0) at a flow rate of 4.5 mL/min. The retention time was 10.5 min, and the yield of the peptide was 84%. MS (ESI): calculated for $C_{41}H_{57}BF_3N_9O_{10}$ [MH]⁺=904.44; observed [MH]⁺=904.60.

EXAMPLE 6

Synthesis of PSMA-PyrBF3 and PSMA-6517-PyrBF3

Scheme 7 shows the synthesis of prosthetic propargylpyridinium trifluoroborate ML-02:

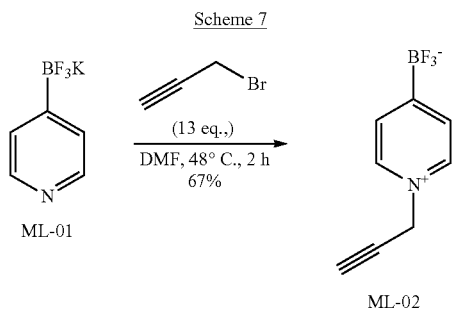

Synthesis of prosthetic propargylpyridinium trifluoroborate ML-02. To an oven-dried 50 mL round bottom flask containing a clear pale yellow solution of potassium pyridine-4-trifluoroborate ML-01 (1 eq., 0.200 g, 1.09 mmol) in DMF (5 mL) was added a 80w % propargyl bromide solution in toluene (13 eq., 1.57 mL, 13.2 mmol) at room temperature. The mixture was heated at 48° C. in an oil bath for 2 h. The reaction progress was monitored by TLC, developed using methanol in ethyl acetate (1:10, v/v) and visualized under UV (Rf=0.33). The reaction mixture was then cooled to room temperature and solvent was removed under high vacuum. The residue was purified by silica gel column chromatography using methanol in ethyl acetate (1:10, v/v) to afford ML-02 a pale yellow solid (0.135 g, 67% yield). ¹H NMR (300 MHz, CD₃CN) δ (ppm) 8.52 (d, J=5.8 Hz, 2H), 8.04 (d, J=5.8 Hz, 2H), 5.27 (d, J=2.6 Hz, 2H), 3.16 (t, J=2.6 Hz, 1H). ¹³C{¹H} NMR (75.5 MHz, CD₃CN) δ (ppm) 141.60 (Ar C), 131.47 (Ar C), 80.32 (CH₂), 75.06 (C), 50.13 (CH). ¹⁹F NMR (282 MHz, CD₃CN) δ (ppm) −146.4 (1:1:1:1 q, J=47 Hz). ESI-MS (TOF) m/z [M+Br]⁻264.2; calc. 263.98 for $C_8H_7N^{11}BF_3Br$.

Compounds PSMA-PyrBF3 and PSMA-617-PyrBF3 are shown below:

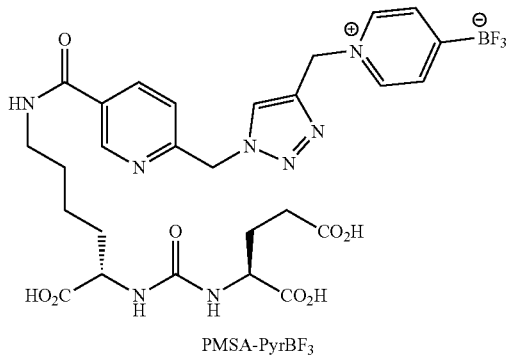

PMSA-PyrBF₃

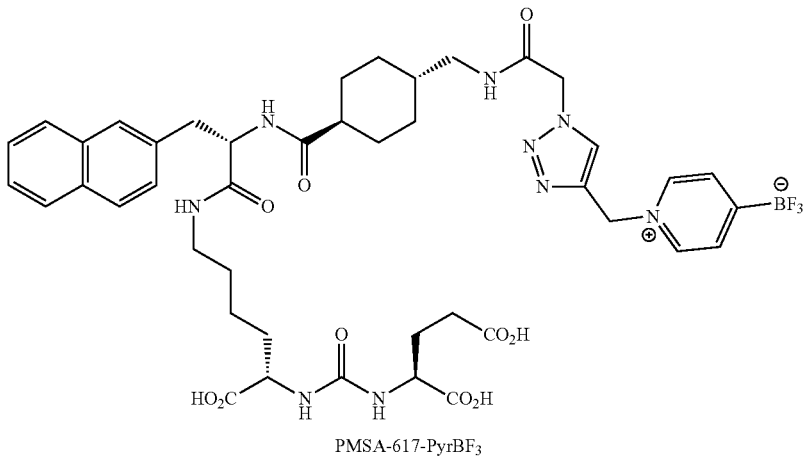

PMSA-617-PyrBF₃

Synthesis of PSMA-PyrBF$_3$. To a solution of prosthetic ML-02 (1 eq., 2.6 mg, 14 μmol) and 14 (2.5 eq., 16.8 mg, 35 μmol) in DMF (500 μL) at room temperature was added a bright yellow solution of Cu$^{(I)}$ prepared by mixing 0.1M aq. CuSO$_4$ (10 mol %, 14 μL, 1.4 μmol), 0.2M aq. sodium ascorbate (20 mol %, 14 μL, 2.8 μmol) and 1M aq. sodium bicarbonate (1 eq., 14 μL, 14 μmol) with H$_2$O (58 μL). The mixture was stirred at room temperature for 2 h, but low conversion was assessed by TLC. An excess of 1M aq. sodium bicarbonate (10 eq., 141 μL, 141 μmol) was added, causing a gas release. To ensure reaction rate, another portion of 0.1 M aq. CuSO$_4$ (35 mol %, 49 μL, 4.9 μmol) and 0.2M aq. sodium ascorbate (70 mol %, 49 μL, 98 μmol) were added. The mixture was stirred at room temperature for 5 min. The reaction was then quenched with 10 drops of ammonia and then filtered through a small silica gel pad (height 2 cm, diameter 0.5 cm) built in a Pasteur pipette, eluting with a 9.5/9.5/1 mixture of MeCN/MeOH/ammonium hydroxide (10 mL). The filtrate was concentrated, then diluted with water (4 mL), frozen and lyophilized. The dry residue was purified by HPLC to afford pure PSMA-pyrBF$_3$ (6.1 mg, 65% yield). $^1$H NMR (300 MHz, MeOD) δ (ppm) 8.92 (d, J=2.0 Hz, 1H), 8.73 (d, J=6.3 Hz, 2H), 8.33 (s, 1H), 8.20 (dd, J=8.1, 2.0 Hz, 1H), 8.05 (d, J=6.3 Hz, 2H), 7.45 (d, J=8.1 Hz, 1H), 5.85 (s, 2H), 5.81 (s, 2H), 4.28 (dd, J=8.4, 4.9 Hz, 2H), 3.39 (t, J=6.7 Hz, 2H), 2.45–2.34 (m, 2H), 2.22–2.05 (m, 1H), 1.97–1.78 (m, 2H), 1.76–1.56 (m, 3H), 1.49 (dd, J=14.4, 7.3 Hz, 2H). $^{19}$F NMR (282 MHz, MeOD) δ (ppm) −147.84 (br s). ESI-HRMS (TOF) m/z [M-H]$^−$ 662.2352; calc. 662.2346 for C$_{27}$H$_{31}$N$_3$O$_8$$^{10}$BF$_3$.

Synthesis of precursor PSMA-617-PyrBF3. To a solution of prosthetic ML-02 (2.0 eq., 1.3 mg, 6.8 μmol) and HTK02073 (1.0 eq., 2.5 mg, 3.4 μmol) in DMF (500 μL), previously treated with 1M aq. NaHCO$_3$ solution (6.0 eq., 20 μL, 20.3 μmol), was added a bright yellow mixture of 0.1M aq. CuSO$_4$ (1 eq., 35 μL, 3.4 μmol) and 0.2M aq. sodium ascorbate (2 eq., 35 μL, 6.8 μmol) in water (110 μL) at room temperature. The mixture was stirred at room temperature for 22 h. Then aq. ammonium hydroxide (200 μL) was added to the mixture, which was then filtered on a silica plug in a Pasteur pipette (height 2 cm, diameter 0.5 cm), eluting with a 9.5/9.5/1 mixture of MeOH/MeCN/ammonium hydroxide (10 mL). The filtrate was concentrated, then diluted with water (5 mL), frozen and lyophilized. The dry residue was purified by HPLC to afford pure PSMA-617-pyrBF$_3$ (1.4 mg, 45% yield). $^1$H NMR (300 MHz, MeOD) δ (ppm) 8.74 (d, J=6.3 Hz, 2H), 8.26 (s, 1H), 8.05 (d, J=6.3 Hz, 2H), 7.85–7.75 (m, 3H), 7.70 (s, 1H), 7.49–7.36 (m, 3H), 5.85 (s, 2H), 5.19 (s, 2H), 4.68 (dd, J=8.8, 6.4 Hz, 2H), 4.22 (dd, J=7.5, 5.1 Hz, 1H), 4.12 (dd, J=8.1, 4.6 Hz, 1H), 3.14–2.98 (m, 4H), 2.46–2.34 (m, 2H), 2.26–2.05 (m, 2H), 2.02–1.86 (m, 1H), 1.74 (dd, J=24.8, 11.0 Hz, 5H), 1.63–1.52 (m, 3H), 1.52–1.23 (m, 8H). $^{19}$F NMR (282 MHz, MeOD) δ (ppm) −148.32 (br s). ESI-HRMS (TOF) m/z [M-H]$^−$921.3918; calc. 921.3919 for C$_{43}$H$_{52}$N$_9$O$_{10}$$^{10}$BF$_3$.

EXAMPLE 7

Radiolabeling

Radiolabeling of $^{19}$F-HTK10069 and $^{19}$F-HTK01070 (synthesis of $^{18}$F-HTK10069 and $^{18}$F-HTK01070). 100 nmol of $^{19}$F-HTK10069 or $^{19}$F-HTK01070 was resuspended with aqueous pyridazine-HCl buffer (15 μL, 1M, pH=2) and DMF (15 μL) in a polypropylene tube. No carrier-added $^{18}$F-fluoride was obtained by bombardment of H$_2$$^{18}$O with 18 MeV protons, followed by trapping on an anion exchange column (9 mg, QMA, chloride form). The $^{18}$F-fluoride was eluted off with saline (70 μL) into the reaction tube. The reaction mixture was heated at 80° C. for 20 min under vacuum, and diluted with PBS (1 mL). The solution was purified by HPLC using the semi-preparative column at a flow rate of 4.5 mL/min, eluted with 3/97 ethanol/PBS or 6/94 ethanol/PBS at a flow rate of 4.5 mL/min, for $^{18}$F-HTK01069 or $^{18}$F-HTK01070, respectively. The retention time was 15.6 min or 11.1 min, for $^{18}$F-HTK01069 or $^{18}$F-HTK01070, respectively. The decay-corrected radiochemical yield was 9% or 3%, for $^{18}$F-HTK01069 or $^{18}$F-HTK01070, respectively. Radiochemical purity of >99% was achieved for the both of labeled tracers as determined by radio HPLC. The specific activity was measured using the analytical HPLC system. It was calculated by dividing the injected radioactivity (·1 mCi) in final product solution by the mass in the injected solution. The mass of injected product was estimated by comparing the UV absorbance obtained from the injection with a previously prepared standard curve. The specific activity was 2.0 Ci/μmol or 1.3 Ci/μmol, for $^{18}$F-HTK01069 or $^{18}$F-HTK01070, respectively.

Radiolabelling of $^{19}$F-HTK01130, $^{19}$F-HTK01146, and $^{19}$F-HTK01157 (synthesis of $^{18}$F-HTK01130, $^{18}$F-HTK01146 and $^{18}$F-HTK01157). 100 nmol of $^{19}$F-HTK01130, $^{19}$F-HTK01146, or $^{19}$F-HTK01157 was suspended with aqueous pyridazine-HCl buffer (15 μL, 1M, pH=2) and DMF (15 μL) in a polypropylene tube. No-carrier-added $^{18}$F-fluoride was obtained by bombardment of H$_2$$^{18}$O with 18 MeV proton, followed by trapping on an anion exchange column (9 mg, chloride form). $^{18}$F-Fluoride was eluted off with saline (70 μL) into the reaction tube. The reaction mixture was heated at 80° C. for 20 min under vacuum, and then diluted with PBS (1 mL). The solution was purified by HPLC using the semi-preparative column at a flow rate of 4.5 mL/min, eluted with 4/96 ethanol/PBS, 18/82 acetonitrile/PBS or 20/80 acetonitrile/PBS at a flow rate of 4.5 mL/min, for $^{18}$F-HTK01130, $^{18}$F-HTK01146, or $^{18}$F-HTK01157, respectively. The retention time was 8.8 min, 18.9 min or 17.7 min for $^{18}$F-HTK01130, $^{18}$F-HTK01146, or $^{18}$F-HTK01157, respectively. The eluate fraction containing $^{18}$F-HTK01130, $^{18}$F-HTK01146, or $^{18}$F-HTK01157 was collected, and used for imaging and biodistribution studies. Quality control was performed using the analytical column eluted with 87/13 water/acetonitrile (0.1% TFA), 73/27 water/acetonitrile (0.1% TFA) or 70/30 water/acetonitrile (0.1% TFA) at a flow rate of 2 mL/min for $^{18}$F-HTK01130, $^{18}$F-HTK01146, or $^{18}$F-HTK01157, respectively. The retention time was 6.4 min, 7.8 min or 7.8 min for $^{18}$F-HTK01130, $^{18}$F-HTK01146, or $^{18}$F-HTK01157, respectively.

Radiolabeling of $^{18}$F-PSMA-PyrBF$_3$ and $^{18}$F-PSMA-617-PyrBF$_3$ (synthesis of $^{18}$F-PSMA-PyrBF$_3$ and $^{18}$F-PSMA-617-PyrBF$_3$). 80 nmol of $^{19}$F-PSMA-pyrBF$_3$ or $^{19}$F-PSMA-617-pyrBF$_3$ was resuspended with aqueous pyridazine-HCl buffer (15 μL, 1M, pH=2), DMF (15 μL) and aqueous KHF$_2$ (4 μL, 5 mM) in a polypropylene tube. No carrier-added $^{18}$F-fluoride was obtained by bombardment of H$_2$$^{18}$O with 18 MeV protons, followed by trapping on an anion exchange column (9 mg, QMA, chloride form). The $^{18}$F-fluoride was eluted off with saline (100 μL) into the reaction tube. The reaction mixture was heated at 80° C. for 20 min under vacuum, and diluted with 40 mM aqueous ammonium formate (2 mL). The solution was purified by HPLC using the semi-preparative column, eluted with 12.5/87.5 MeCN/water (+0.1% TFA) or 35/65 MeCN/water (+0.1% TFA) at a flow rate of 4.5 mL/min, for $^{18}$F-PSMA- PyrBF$_3$ or $^{18}$F-PSMA-617-PyrBF$_3$, respectively. The retention time was 21.6 min or 9.3 min, for $^{18}$F-PSMA-PyrBF$_3$ or $^{18}$F-PSMA-617-PyrBF$_3$, respectively.

EXAMPLE 8

In Vivo Evaluation of F-18 Labeled HTK-01069 and HTK-01070

Cell Culture

LNCap cell line used in the tumor model was obtained commercially from ATTC (LNCaP clone FGC, CRL-1740). It was established from a metastatic site of left supraclavicular lymph node of human prostatic adenocarcinoma. Cells were cultured in PRMI 1640 (StemCell Technologies, Vancouver, BC) supplemented by 10% FBS, 100 U/mL penicillin and 100 µg/mL streptomycin at 37° C. in a humidified incubator containing 5% CO2. Cells grown to 80-90% confluence were then washed with sterile phosphate-buffered saline (1×PBS pH 7.4) and trypsinization. The collected cells number was counted with Hemacytometer (Hausser Scientific).

Imaging and Biodistribution of F-18 Labeled HTK-01069 and HTK-01070 in Mice

Tumor implantation: Imaging and biodistribution experiments were performed using NODSCID 1L2RγKO male mice. Three or four mice in each cage equipped with enrichments. The mice were maintained and the experiments were conducted in according to the guidelines established by Canadian Council on Animal Care and approved by Animal Ethics Committee of the University of British Columbia. Mice were housed under pathogen-free conditions and kept on twelve hours light and twelve hours dark cycle in the Animal Research Centre, British Columbia Cancer Research Centre, Vancouver, Canada.

Mice were anesthetized by inhalation with 2.5% isoflurane in 2.0 L/min of oxygen during cells implantation. Mice were implanted subcutaneously with 1×107 LNCaP cells behind left shoulder. Mice were imaged or used in biodistribution studies when the tumor grew up to reach 5-8 mm in diameter during 5-6 weeks.

Figure 2A:
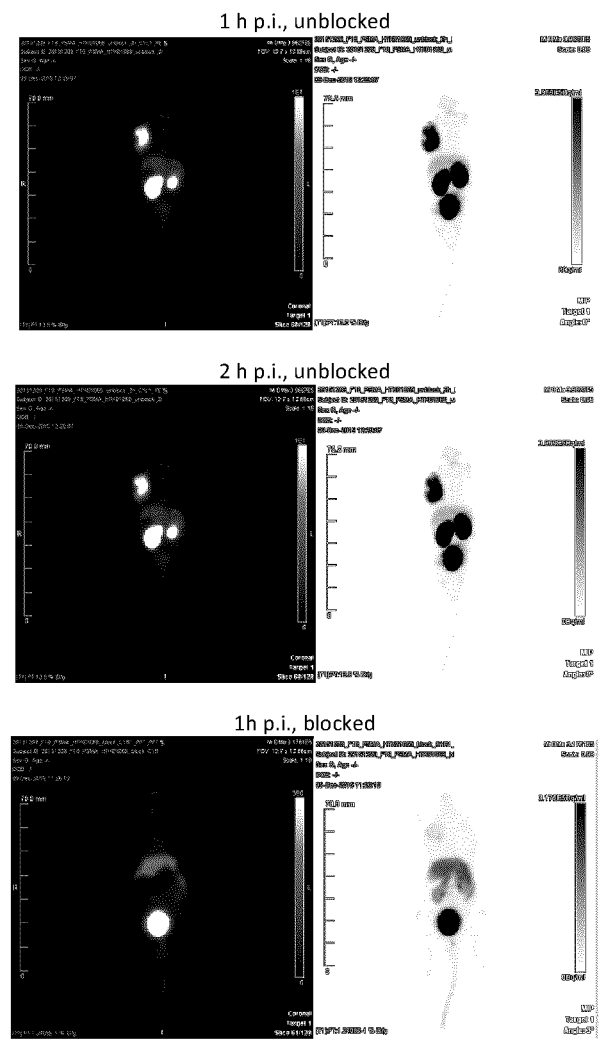
FIG. 2A shows reconstructed F-18 HTK-01069 images of SCID IL2RγKO mouse bearing tumors derived from LNCaP cells. Unblocked, 1 h (upper) and 2 h (middle) post-injection (Scale bar 0-10% ID/g); blocked (bottom), 1 h post-injection by pre-injected with 0.5 mg DCFPyL.
Figure 2B:
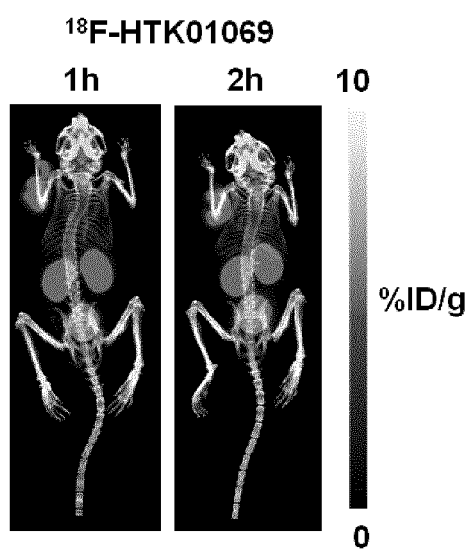
FIG. 2B shows maximum intensity projection PET/CT images of $^{18}$F-HTK01069 acquired at 1 h and 2 h post-injection.
Figure 3A:
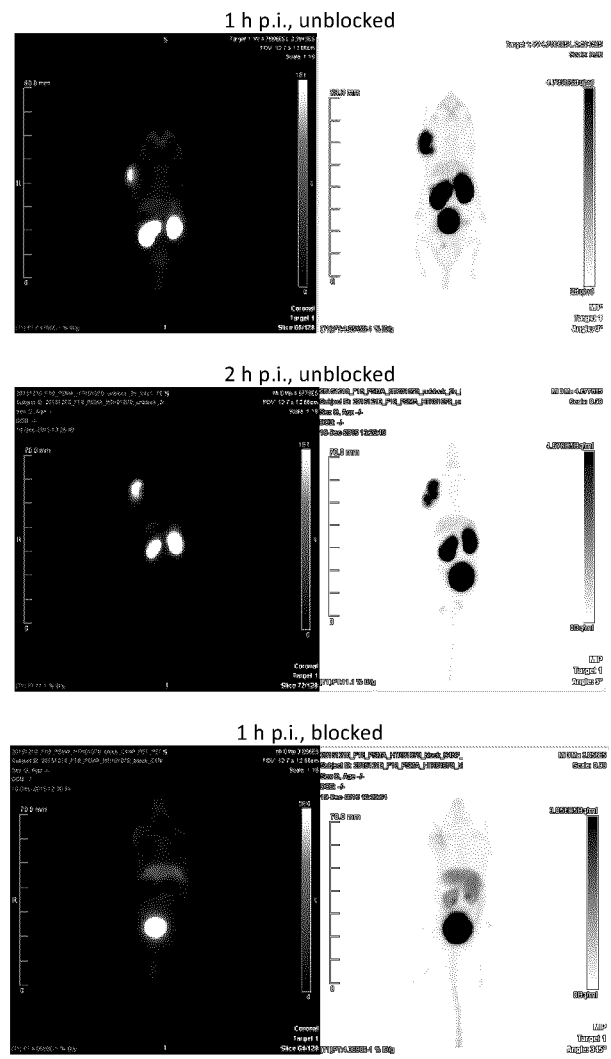
FIG. 3A shows a reconstructed F-18 HTK-01070 images of SCID IL2RγKO mouse bearing tumors derived from LNCaP cells. Unblocked, 1 h (upper) and 2 h (middle) post-injection (Scale bar 0-10% ID/g); blocked (bottom), 1 h post-injection by pre-injected with 0.5 mg DCFPyL.
Figure 3B:
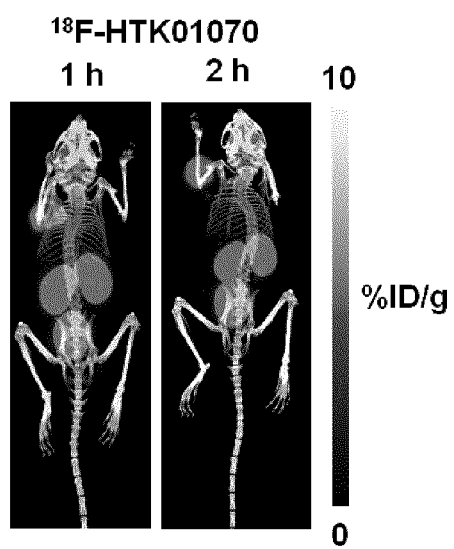
FIG. 3B shows maximum intensity projection PET/CT images of 18F-HTK01070 acquired at 1 h and 2 h post-injection.
Figure 4:
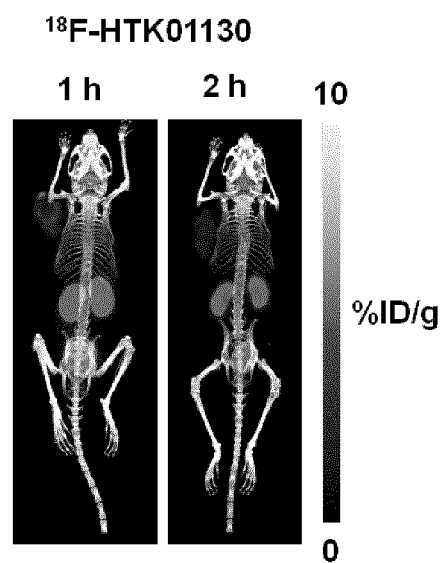
FIG. 4 shows maximum intensity projection PET/CT images of $^{18}$F-HTK01130 acquired at 1 h and 2 h post-injection.
Figure 5:
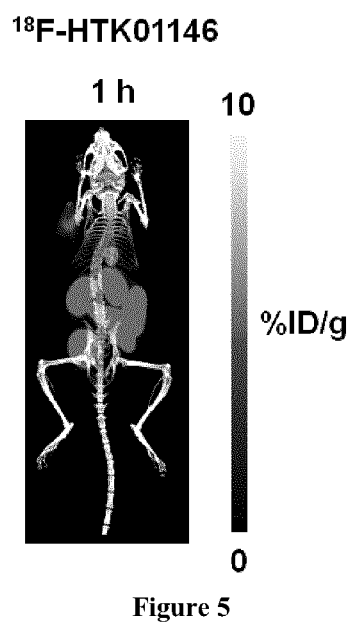
FIG. 5 shows maximum intensity projection PET/CT image of 18F-HTK01146 acquired at 1 h post-injection.
Figure 6:
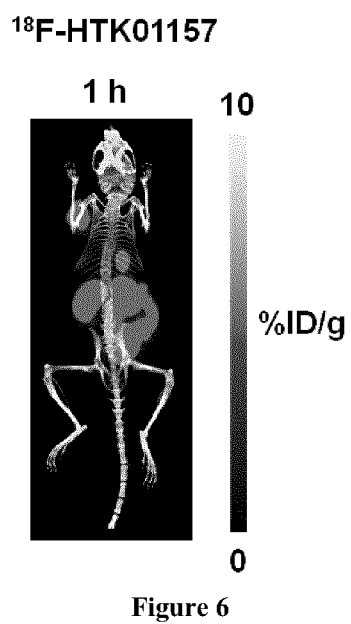
FIG. 6 shows maximum intensity projection PET/CT image of $^{18}$F-HTK01157 acquired at 1 h post-injection.
Figure 7:
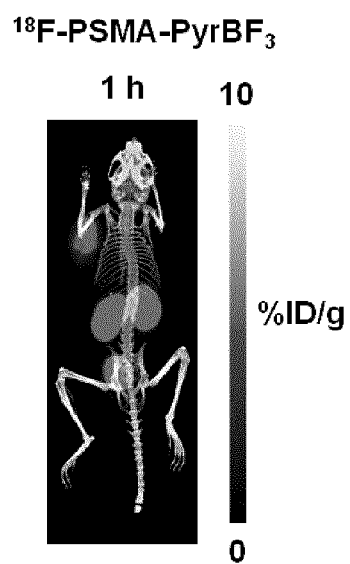
FIG. 7 shows maximum intensity projection PET/CT image of 18F-PSMA-PyrBF3 acquired at 1 h post-injection.
Figure 8:
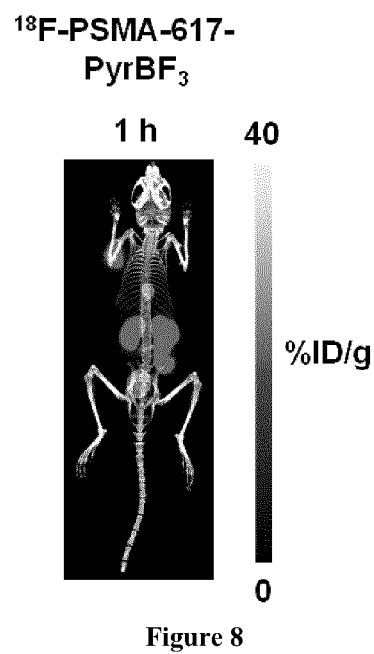
FIG. 8 shows maximum intensity projection PET/CT image of 18F-PSMA-617-PyrBF3 acquired at 1 h post-injection.

PET/CT Imaging: PET imaging experiments were conducted using Siemens inveon micro PET/CT scanner. Each tumor bearing mouse was injected ~6.44 MBq of F-18 labeled HTK-01069 and ~7.08 MBq of F-18 labeled HTK-01070 through the tail vein under anesthesia. After one hour, the mice were sedated again with 2% isoflurane inhalation and positioned in the scanner. Static PET imaging was performed to determined activity uptake of tumor and other organs. A CT scan was obtained for localization and attenuation correction after segmentation for reconstructing the PET images. The data was acquired by scanning the mice for 10 minutes each. The mice were kept warm by a heating pad during acquisition. The mice were euthanized after imaging and followed by biodistribution. Please see FIGS. 2 and 3 of this specification for reconstructed PET images for 1L2RγKO mice injected with HTK-01069 and HTK-01070 respectively.

Biodistribution: Each mouse was anesthetized by 2% isoflurane inhalation, and then sacrificed by CO2 inhalation at 60 minutes p.i. Blood was withdrawn immediately, and the organs of interest were quickly removed. Each organ was weighed and the tissue radioactivity was measured with a Cobra II gamma counter (Packard), normalized to the injected dose using a standard curve and expressed as the percentage of the injected dose per gram of tissue (% ID/g).

Biodistribution data are shown for HTK-01069 in Tables 5, 6 and 7 and HTK-01070 in Tables 8, 9, 10 of the specification respectively.

TABLE 5

Biodistribution of F-18 HTK-01069 in SCID IL2RγKO tumor-bearing mice at 1 h p.i.

| Tissue | Mouse 1 % ID/g | Mouse 2 % ID/g | Mouse 3 % ID/g | Mouse4 % ID/g | Avg % ID/g | STD |
|---|---|---|---|---|---|---|
| Blood | 0.79 | 0.40 | 0.36 | 0.53 | 0.52 | 0.19 |
| Fat | 0.95 | 1.21 | 0.74 | 1.46 | 1.09 | 0.31 |
| Seminal | 0.13 | 0.11 | 1.19 | 9.86 | 2.82 | 4.72 |
| Testes | 0.44 | 0.58 | 0.51 | 0.60 | 0.53 | 0.07 |
| Intestine | 0.43 | 0.59 | 0.54 | 0.64 | 0.55 | 0.09 |
| Stomach | 1.64 | 4.28 | 3.35 | 2.70 | 2.99 | 1.11 |
| Spleen | 0.30 | 0.51 | 0.38 | 0.72 | 0.48 | 0.18 |
| Liver | 0.08 | 0.09 | 0.24 | 0.14 | 0.14 | 0.07 |
| Pancreas | 2.32 | 2.86 | 2.76 | 3.17 | 2.77 | 0.35 |
| Adrenals | 3.55 | 2.85 | 3.73 | 5.80 | 3.98 | 1.27 |
| Kidney | 36.69 | 117.33 | 93.48 | 124.11 | 92.90 | 39.71 |
| Lung | 0.21 | 0.28 | 0.22 | 0.32 | 0.26 | 0.05 |
| Heart | 0.83 | 1.02 | 1.14 | 1.67 | 1.16 | 0.36 |
| Tumour | 7.84 | 4.16 | 4.47 | 5.86 | 5.58 | 1.68 |
| Muscle | 0.36 | 0.39 | 0.34 | 0.35 | 0.36 | 0.02 |
| Bone | 0.45 | 0.19 | 0.18 | 0.27 | 0.27 | 0.12 |
| Brain | 0.03 | 0.03 | 0.03 | 0.03 | 0.03 | 0.00 |
| Tail | 0.70 | 0.47 | 0.57 | 0.74 | 0.62 | 0.13 |

TABLE 6

Biodistribution of F-18 HTK-01069 in SCID IL2RγKO tumor-bearing mice at 2 h p.i.

| Tissue | Mouse 1 % ID/g | Mouse 2 % ID/g | Mouse 3 % ID/g | Mouse4 % ID/g | Avg % ID/g | STD |
|---|---|---|---|---|---|---|
| Blood | 0.20 | 0.08 | 0.22 | 0.14 | 0.16 | 0.06 |
| Fat | 0.00 | 0.44 | 0.53 | 0.77 | 0.43 | 0.32 |
| Seminal | 1.84 | 0.05 | 9.96 | 1.13 | 3.24 | 4.54 |
| Testes | 0.41 | 0.37 | 0.39 | 0.41 | 0.39 | 0.02 |
| Intestine | 0.78 | 0.92 | 0.63 | 0.68 | 0.75 | 0.13 |
| Stomach | 0.66 | 1.89 | 2.78 | 3.67 | 2.25 | 1.29 |
| Spleen | 0.31 | 0.18 | 0.21 | 0.33 | 0.26 | 0.07 |
| Liver | 0.06 | 0.10 | 0.04 | 0.05 | 0.06 | 0.03 |
| Pancreas | 2.39 | 1.89 | 2.21 | 2.48 | 2.24 | 0.26 |
| Adrenals | 3.70 | 1.17 | 1.11 | 2.06 | 2.01 | 1.21 |
| Kidney | 62.04 | 35.60 | 49.89 | 59.65 | 51.79 | 12.01 |
| Lung | 0.16 | 0.09 | 0.11 | 0.14 | 0.12 | 0.03 |
| Heart | 0.63 | 0.61 | 0.79 | 0.84 | 0.72 | 0.12 |
| Tumour | 5.03 | 4.25 | 5.74 | 6.41 | 5.36 | 0.93 |
| Muscle | 0.29 | 0.18 | 0.22 | 0.28 | 0.24 | 0.05 |
| Bone | 0.12 | 0.08 | 0.14 | 0.13 | 0.12 | 0.03 |
| Brain | 0.04 | 0.02 | 0.03 | 0.02 | 0.03 | 0.01 |
| Tail | 0.29 | 0.24 | 0.36 | 0.34 | 0.31 | 0.05 |

TABLE 7

Biodistribution of F-18 HTK-01069 in SCID IL2RγKO tumor-bearing mice at 1 h p.i. with co-injection of 0.5 mg DCFPyL.

| Tissue | Mouse 1 % ID/g | Mouse 2 % ID/g | Mouse 3 % ID/g | Mouse4 % ID/g | Avg % ID/g | STD |
|---|---|---|---|---|---|---|
| Blood | 0.23 | 0.84 | 0.38 | 0.34 | 0.45 | 0.27 |
| Fat | 0.00 | 0.26 | 0.12 | 0.08 | 0.11 | 0.11 |
| Seminal | 0.09 | 0.09 | 1.29 | 0.05 | 0.38 | 0.61 |
| Testes | 0.07 | 0.13 | 0.12 | 0.09 | 0.10 | 0.02 |
| Intestine | 0.37 | 0.89 | 0.48 | 0.55 | 0.57 | 0.23 |
| Stomach | 0.08 | 0.13 | 0.15 | 0.15 | 0.13 | 0.03 |
| Spleen | 0.06 | 0.15 | 0.12 | 0.11 | 0.11 | 0.03 |
| Liver | 0.03 | 0.14 | 0.07 | 0.21 | 0.11 | 0.08 |
| Pancreas | 2.40 | 3.36 | 2.71 | 3.53 | 3.00 | 0.53 |
| Adrenals | 0.17 | 0.48 | 0.44 | 0.30 | 0.35 | 0.14 |

TABLE 7-continued

Biodistribution of F-18 HTK-01069 in SCID IL2RγKO tumor-bearing mice at 1 h p.i. with co-injection of 0.5 mg DCFPyL.

| Tissue | Mouse 1 % ID/g | Mouse 2 % ID/g | Mouse 3 % ID/g | Mouse4 % ID/g | Avg % ID/g | STD |
|---|---|---|---|---|---|---|
| Kidney | 2.35 | 3.57 | 4.08 | 4.15 | 3.54 | 0.83 |
| Lung | 0.10 | 0.20 | 0.16 | 0.13 | 0.15 | 0.04 |
| Heart | 0.17 | 0.31 | 0.27 | 0.26 | 0.25 | 0.06 |
| Tumour | 0.30 | 0.35 | 0.26 | 0.42 | 0.33 | 0.07 |
| Muscle | 0.22 | 0.36 | 0.37 | 0.26 | 0.30 | 0.07 |
| Bone | 0.15 | 0.17 | 0.11 | 0.10 | 0.13 | 0.03 |
| Brain | 0.02 | 0.03 | 0.04 | 0.02 | 0.03 | 0.01 |
| Tail | 0.43 | 0.41 | 0.37 | 0.55 | 0.44 | 0.08 |

TABLE 8

Biodistribution of F-18 HTK-01070 in SCID IL2RγKO tumor-bearing mice at 1 h p.i.

| Tissue | Mouse 1 % ID/g | Mouse 2 % ID/g | Mouse 3 % ID/g | Mouse4 % ID/g | Mouse 5 % ID/g | Mouse 6 % ID/g | Avg % ID/g | STD |
|---|---|---|---|---|---|---|---|---|
| Blood | 0.46 | 0.63 | 0.50 | 0.51 | 0.50 | 0.51 | 0.52 | 0.06 |
| Fat | 0.39 | 1.04 | 0.69 | 0.48 | 0.81 | 0.97 | 0.73 | 0.26 |
| Seminal | 15.94 | 0.12 | 0.37 | 0.11 | 1.99 | 0.23 | 3.13 | 6.32 |
| Testes | 0.94 | 0.79 | 0.49 | 0.57 | 0.58 | 0.64 | 0.67 | 0.17 |
| Intestine | 0.26 | 0.32 | 0.42 | 0.37 | 0.31 | 0.31 | 0.33 | 0.05 |
| Stomach | 0.08 | 0.09 | 0.10 | 0.16 | 0.08 | 0.12 | 0.10 | 0.03 |
| Spleen | 5.58 | 4.75 | 5.97 | 4.51 | 4.95 | 4.31 | 5.01 | 0.64 |
| Liver | 1.51 | 1.53 | 1.65 | 1.90 | 1.60 | 1.94 | 1.69 | 0.19 |
| Pancreas | 0.30 | 0.33 | 0.35 | 0.28 | 0.32 | 0.41 | 0.33 | 0.05 |
| Adrenals | 4.98 | 7.35 | 4.19 | 1.90 | 4.52 | 4.96 | 4.65 | 1.75 |
| Kidney | 62.45 | 54.11 | 52.66 | 91.10 | 76.59 | 93.32 | 71.70 | 18.03 |
| Lung | 1.32 | 1.35 | 1.24 | 1.21 | 1.59 | 1.61 | 1.39 | 0.17 |
| Heart | 0.36 | 0.47 | 0.37 | 0.27 | 0.24 | 0.28 | 0.33 | 0.08 |
| Tumour | 7.56 | 10.45 | 8.06 | 8.60 | 8.31 | 6.70 | 8.28 | 1.25 |
| Muscle | 0.28 | 0.21 | 0.24 | 0.17 | 0.25 | 0.22 | 0.23 | 0.04 |
| Bone | 0.37 | 0.33 | 0.58 | 0.52 | 0.38 | 0.45 | 0.44 | 0.09 |
| Brain | 0.03 | 0.03 | 0.04 | 0.04 | 0.03 | 0.05 | 0.04 | 0.01 |
| Tail | 0.85 | 0.56 | 0.63 | 1.14 | 0.75 | 0.61 | 0.76 | 0.21 |

TABLE 9

Biodistribution of F-18 HTK-01070 in SCID IL2RγKO tumor-bearing mice at 2 h p.i.

| Tissue | Mouse 1 % ID/g | Mouse 2 % ID/g | Mouse 3 % ID/g | Mouse4 % ID/g | Mouse 5 % ID/g | Avg % ID/g | STD |
|---|---|---|---|---|---|---|---|
| Blood | 0.08 | 0.19 | 0.20 | 0.08 | 0.27 | 0.16 | 0.08 |
| Fat | 0.00 | 0.53 | 0.67 | 0.32 | 0.38 | 0.38 | 0.25 |
| Seminal | 10.78 | 2.48 | 17.33 | 1.31 | 0.13 | 6.41 | 7.40 |
| Testes | 0.23 | 0.34 | 0.26 | 0.19 | 0.36 | 0.28 | 0.07 |
| Intestine | 0.21 | 0.23 | 0.26 | 0.24 | 0.32 | 0.25 | 0.04 |
| Stomach | 1.10 | 0.76 | 1.56 | 1.25 | 1.83 | 1.30 | 0.41 |
| Spleen | 0.09 | 0.22 | 0.19 | 0.10 | 0.24 | 0.17 | 0.07 |
| Liver | 0.04 | 0.06 | 0.04 | 0.05 | 0.07 | 0.05 | 0.01 |
| Pancreas | 1.30 | 1.76 | 1.41 | 1.23 | 1.80 | 1.50 | 0.26 |
| Adrenals | 0.83 | 1.93 | 2.18 | 1.48 | 2.51 | 1.79 | 0.65 |
| Kidney | 16.75 | 71.59 | 58.29 | 29.51 | 37.76 | 42.78 | 22.08 |
| Lung | 0.05 | 0.11 | 0.09 | 0.06 | 0.12 | 0.09 | 0.03 |
| Heart | 0.32 | 0.58 | 0.55 | 0.44 | 0.46 | 0.47 | 0.10 |
| Tumour | 6.12 | 6.47 | 7.93 | — | — | 6.84 | 0.96 |
| Muscle | 0.31 | 0.39 | 0.27 | 0.33 | 0.44 | 0.35 | 0.06 |
| Bone | 0.07 | 0.10 | 0.10 | 0.16 | 0.08 | 0.10 | 0.04 |
| Brain | 0.02 | 0.03 | 0.02 | 0.02 | 0.02 | 0.02 | 0.00 |
| Tail | 0.34 | 0.79 | 0.97 | 0.31 | 0.40 | 0.56 | 0.30 |

TABLE 10

Biodistribution of F-18 HTK-01070 in SCID IL2RγKO tumor-bearing mice at 1 h p.i. with co-injection of 0.5 mg DCFPyL.

| Tissue | Mouse 1 % ID/g | Mouse 2 % ID/g | Mouse 3 % ID/g | Mouse4 % ID/g | Avg % ID/g | STD |
|---|---|---|---|---|---|---|
| Blood | 0.31 | 0.70 | 0.62 | 0.21 | 0.46 | 0.24 |
| Fat | 0.00 | 0.06 | 0.06 | 0.05 | 0.04 | 0.03 |
| Seminal | 0.14 | 7.28 | 0.03 | 0.03 | 1.87 | 3.61 |
| Testes | 0.09 | 0.10 | 0.06 | 0.06 | 0.08 | 0.02 |
| Intestine | 0.31 | 0.30 | 0.28 | 0.32 | 0.31 | 0.02 |
| Stomach | 0.09 | 0.14 | 0.07 | 0.07 | 0.09 | 0.03 |
| Spleen | 0.06 | 0.06 | 0.05 | 0.05 | 0.06 | 0.01 |
| Liver | 0.06 | 0.08 | 0.07 | 0.05 | 0.06 | 0.02 |
| Pancreas | 1.92 | 1.65 | 1.88 | 1.57 | 1.76 | 0.17 |

TABLE 10-continued

Biodistribution of F-18 HTK-01070 in SCID IL2RγKO
tumor-bearing mice at 1 h p.i. with co-injection of 0.5 mg DCFPyL.

| Tissue | Mouse 1 % ID/g | Mouse 2 % ID/g | Mouse 3 % ID/g | Mouse 4 % ID/g | Avg % ID/g | STD |
|---|---|---|---|---|---|---|
| Adrenals | 0.23 | 0.26 | 0.17 | 0.16 | 0.20 | 0.05 |
| Kidney | 2.40 | 2.05 | 2.05 | 1.96 | 2.11 | 0.19 |
| Lung | 0.11 | 0.10 | 0.07 | 0.08 | 0.09 | 0.02 |
| Heart | 0.21 | 0.27 | 0.20 | 0.19 | 0.22 | 0.03 |
| Tumour | 0.35 | 0.26 | 0.21 | 0.26 | 0.27 | 0.06 |
| Muscle | 0.31 | 0.38 | 0.23 | 0.29 | 0.30 | 0.06 |
| Bone | 0.07 | 0.12 | 0.11 | 0.18 | 0.12 | 0.05 |
| Brain | 0.02 | 0.02 | 0.02 | 0.02 | 0.02 | 0.00 |
| Tail | 0.45 | 0.35 | 0.35 | 0.36 | 0.38 | 0.05 |

EXAMPLE 8

In Vivo Evaluation of F-18 Labeled Compounds
Cell Culture

LNCap cell line was obtained from ATCC (LNCaP clone FGC, CRL-1740). It was established from a metastatic site of left supraclavicular lymph node of human prostatic adenocarcinoma. Cells were cultured in PRMI 1640 medium supplemented with 10% FBS, penicillin (100 U/mL) and streptomycin (100 μg/mL) at 37° C. in a humidified incubator containing 5% $CO_2$. Cells grown to 80-90% confluence were then washed with sterile phosphate-buffered saline (1×PBS pH 7.4) and trypsinization. The collected cells number was counted with a Hausser Scientific (Horsham, Pa.) Hemacytometer.

PET/CT Imaging and Biodistribution

Imaging and biodistribution experiments were performed using NODSCID 1L2RγKO male mice. Mice were anesthetized by inhalation with 2% isoflurane in oxygen, and implanted subcutaneously with $1 \times 10^7$ LNCaP cells behind left shoulder. Mice were imaged or used in biodistribution studies when the tumor grew up to reach 5-8 mm in diameter during 5-6 weeks.

PET imaging experiments were conducted using Siemens Inveon micro PET/CT scanner. Each tumor bearing mouse was injected 6-8 MBq of F-18 labeled tracer through the tail vein under anesthesia (2% isoflurane in oxygen). The mice were allowed to recover and roam freely in their cage. After 50 min, the mice were sedated again with 2% isoflurane in oxygen inhalation and positioned in the scanner. A 10-min CT scan was conducted first for localization and attenuation correction after segmentation for reconstructing the PET images. Then, a 10-min static PET imaging was performed to determined uptake in tumor and other organs. The mice were kept warm by a heating pad during acquisition. For imaging studies acquired at 2 h post-injection (p.i.), the mice were placed in the micro PET/CT scanner at 110 min p.i. Then, the CT and PET acquisitions were conducted as described above.

For biodistribution studies, the mice were injected with the radiotracer as described above. At predetermined time points (1 or 2 h), the mice was anesthetized with 2% isoflurane inhalation, and euthanized by $CO_2$ inhalation. Blood was withdrawn immediately from the heart, and the organs/tissues of interest were collected. The collected organs/tissues were weighed and counted using an automatic gamma counter. The uptake in each organ/tissue was normalized to the injected dose using a standard curve, and expressed as the percentage of the injected dose per gram of tissue (% ID/g).

TABLE 11

Biodistribution data and tumor-to-background contrast ratios of $^{18}$F-labeled HTK01069, HTK01070 and HTK01130 in mice bearing PSMA-expressing LNCAP cancer xenografts

| Tissue (% ID/g) | $^{18}$F-HTK01069 | | $^{18}$F-HTK01070 | | $^{18}$F-HTK01130 | |
|---|---|---|---|---|---|---|
| | 1 h (n = 8) | 2 h (n = 10) | 1 h (n = 6) | 2 h (n = 7) | 1 h (n = 6) | 2 h (n = 5) |
| Blood | 0.57 ± 0.15 | 0.24 ± 0.10 | 0.52 ± 0.06 | 0.23 ± 0.11 | 0.58 ± 0.09 | 0.21 ± 0.10 |
| Fat | 0.99 ± 0.39 | 0.86 ± 0.53 | 0.73 ± 0.26 | 0.62 ± 0.34 | 0.39 ± 0.14 | 0.32 ± 0.30 |
| Testes | 0.62 ± 0.15 | 0.40 ± 0.06 | 0.67 ± 0.17 | 0.36 ± 0.21 | 0.30 ± 0.05 | 0.16 ± 0.10 |
| Intestine | 0.54 ± 0.11 | 0.72 ± 0.15 | 0.33 ± 0.05 | 0.29 ± 0.08 | 0.31 ± 0.01 | 0.24 ± 0.11 |
| Spleen | 2.67 ± 0.98 | 1.93 ± 0.85 | 5.01 ± 0.64 | 1.30 ± 0.48 | 0.95 ± 0.56 | 0.39 ± 0.35 |
| Pancreas | 0.55 ± 0.16 | 0.41 ± 0.20 | 0.33 ± 0.05 | 0.21 ± 0.07 | 0.31 ± 0.11 | 0.20 ± 0.18 |
| Stomach | 0.12 ± 0.05 | 0.09 ± 0.03 | 0.10 ± 0.03 | 0.06 ± 0.02 | 0.09 ± 0.03 | 0.05 ± 0.03 |
| Liver | 2.90 ± 0.56 | 2.75 ± 0.56 | 1.69 ± 0.19 | 1.50 ± 0.30 | 1.26 ± 0.27 | 1.20 ± 0.30 |
| Adrenal glands | 4.77 ± 1.75 | 3.66 ± 2.01 | 4.65 ± 1.75 | 2.11 ± 0.78 | 1.46 ± 0.56 | 1.08 ± 0.51 |
| Kidneys | 114 ± 41.3 | 103 ± 56.7 | 71.7 ± 18.0 | 68.5 ± 28.7 | 63.3 ± 13.5 | 48.2 ± 24.6 |
| Heart | 0.30 ± 0.06 | 0.20 ± 0.08 | 0.33 ± 0.08 | 0.13 ± 0.06 | 0.21 ± 0.05 | 0.10 ± 0.04 |
| Lungs | 1.37 ± 0.36 | 0.99 ± 0.32 | 1.39 ± 0.17 | 0.69 ± 0.23 | 0.75 ± 0.10 | 0.30 ± 0.10 |
| Tumor | 6.04 ± 1.24 | 5.47 ± 0.75 | 8.28 ± 1.25 | 7.56 ± 1.57 | 4.44 ± 1.11 | 4.27 ± 0.65 |
| Bone | 0.36 ± 0.02 | 0.30 ± 0.10 | 0.44 ± 0.09 | 0.30 ± 0.06 | 0.22 ± 0.05 | 0.20 ± 0.09 |
| Muscle | 0.26 ± 0.08 | 0.15 ± 0.04 | 0.23 ± 0.04 | 0.12 ± 0.03 | 0.20 ± 0.07 | 0.08 ± 0.03 |
| Brain | 0.04 ± 0.01 | 0.04 ± 0.01 | 0.04 ± 0.01 | 0.03 ± 0.01 | 0.04 ± 0.01 | 0.03 ± 0.01 |
| Tumor:Blood | 10.8 ± 1.64 | 26.9 ± 13.3 | 16.0 ± 1.37 | 38.9 ± 18.8 | 7.60 ± 1.33 | 7.60 ± 1.33 |
| Tumor:Muscle | 23.4 ± 3.71 | 37.4 ± 8.86 | 37.3 ± 9.53 | 67.7 ± 14.8 | 24.1 ± 8.79 | 24.1 ± 8.79 |
| Tumor:kidney | 0.07 ± 0.06 | 0.07 ± 0.03 | 0.12 ± 0.04 | 0.14 ± 0.10 | 0.07 ± 0.02 | 0.07 ± 0.02 |

TABLE 12

Biodistribution data and tumor-to-background contrast ratios of $^{18}$F-labeled HTK01146, HTK01157, PSMA-PyrBF$_3$ and PSMA-617 PyrBF$_3$ in mice bearing PSMA-expressing LNCAP cancer xenografts.

| Tissue (% ID/g) | $^{18}$F-HTK01146 1 h (n = 6) | $^{18}$F-HTK01157 1 h (n = 6) | $^{18}$F-PSMA-617-PyrBF$_3$ 1 h (n = 8) | $^{18}$F-PSMA PyrBF$_3$ 1 h (n = 7) |
|---|---|---|---|---|
| Blood | 0.13 ± 0.08 | 0.89 ± 0.42 | 1.45 ± 1.15 | 0.74 ± 0.15 |
| Fat | 0.27 ± 0.14 | 0.83 ± 0.33 | 0.42 ± 0.30 | 1.05 ± 0.49 |
| Testes | 0.18 ± 0.05 | 0.74 ± 0.55 | 0.39 ± 0.13 | 0.67 ± 0.27 |
| Intestine | 22.2 ± 2.79 | 13.0 ± 4.61 | 20.8 ± 4.79 | 0.48 ± 0.22 |
| Spleen | 0.75 ± 0.36 | 2.67 ± 0.98 | 2.84 ± 1.51 | 3.36 ± 1.08 |
| Pancreas | 0.13 ± 0.11 | 0.30 ± 0.17 | 0.26 ± 0.08 | 0.68 ± 0.50 |
| Stomach | 0.21 ± 0.12 | 0.37 ± 0.45 | 0.98 ± 0.12 | 0.15 ± 0.03 |
| Liver | 0.83 ± 0.34 | 1.14 ± 0.48 | 1.10 ± 0.28 | 1.28 ± 0.18 |
| Adrenal glands | 0.81 ± 0.25 | 2.89 ± 1.94 | 2.02 ± 0.56 | 6.66 ± 2.33 |
| Kidneys | 29.9 ± 25.0 | 73.9 ± 35.2 | 83.5 ± 35.7 | 164 ± 50.2 |
| Heart | 0.07 ± 0.02 | 0.31 ± 0.11 | 0.25 ± 0.06 | 0.34 ± 0.08 |
| Lungs | 0.40 ± 0.13 | 1.21 ± 0.48 | 1.06 ± 0.23 | 1.67 ± 0.47 |
| Tumor | 5.09 ± 1.10 | 14.0 ± 5.20 | 23.1 ± 8.26 | 6.26 ± 0.82 |
| Bone | 0.10 ± 0.07 | 0.34 ± 0.14 | 0.54 ± 0.14 | 0.76 ± 0.57 |
| Muscle | 0.05 ± 0.01 | 0.36 ± 0.18 | 0.18 ± 0.03 | 0.28 ± 0.07 |
| Brain | 0.01 ± 0.01 | 0.04 ± 0.01 | 0.03 ± 0.00 | 0.05 ± 0.01 |
| Tumor:Blood | 54.6 ± 38.5 | 17.1 ± 5.40 | 35.4 ± 27.6 | 8.67 ± 1.74 |
| Tumor:Muscle | 117 ± 52.1 | 49.7 ± 28.5 | 145 ± 57.0 | 23.5 ± 5.00 |
| Tumor:kidney | 0.28 ± 0.22 | 0.21 ± 0.08 | 0.32 ± 0.11 | 0.04 ± 0.02 |

The suitability of the tracers disclosed herein for imaging was demonstrated for various compounds herein in imaging studies in mice bearing PSMA-expressing LNCap prostate cancer xenografts (see FIGS. 2-8 and Tables 5-12).

F-18 DCFPyL is currently the most sensitive tracer for the identification of PSMA-positive prostate cancer. Compared with F-18 DCFPyL, HTK-01069 and HTK-01070 showed comparable uptake and PET imaging properties in PSMA-expressing LNCap prostate cancer xenografts, which indicates the usefulness of at least these two tracers for detection/identification of PSMA-expressing tumours in prostate cancer patients who could then benefit from PSMA-targeted therapies (such as Lu-177 labeled PSMA for radiotherapy).

In addition, since PSMA expression has been demonstrated in the tumor neovasculature of a number of cancers, radiolabeled PSMA-targeting tracers (such as those disclosed therein) may be used for the detection/treatment of cancers other than prostate cancer.

REFERENCES NOT CITED IN-LINE

Maresca K P, Hillier S M, Femia F J, Keith D, Barone C, Joyal J L, Zimmerman C N, Kozikowski A P, Barrett J A, Eckelman W C, Babich J W. A series of halogenated heterodimeric inhibitors of prostate specific membrane antigen (PSMA) as radiolabeled probes for targeting prostate cancer. Journal of Medicine Chemistry 2009; 52: 347-357.

Bouvet V, Wuest M, Jans H-S, Janzen N, Genady A R, Valliant J F, Bernard F, Wuest F. Automated synthesis of [18F]DCFPyL via direct radiofluorination and validation in preclinical prostate cancer models. EJNMMI Research 2016; 6: 40.

Horiuchi T, Nagata M, Kitagawa M, Akahane K, Uoto K. Discovery of novel thieno[2,3-d]pyrimidin-4-yl hydrazone-based inhibitors of Cyclin D1-CDK4: Synthesis, biological evaluation and structure-activity relationships. Part 2. Bioorganic and Medicinal Chemistry 2009; 17: 7850-7860.

Zhou Z, Fahrni C J. A fluorogenic probe for the copper(I)-catalyzed azide-alkyne ligation reaction: modulation of the fluorescence emission via $^3(n,\pi^*)$-$^1(\pi, \pi^*)$ inversion. Journal of American Chemical Society 2004; 126: 8862-8863.

Liu Z, Pourghiasian M, Benard F, Pan J, Lin K S, Perrin D M. Preclinical evaluation of a high affinity $^{18}$F-trifluoroborate octreotate derivative for somatostatin receptor imaging. Journal of Nuclear Medicine 2014; 55: 1499-1505.

Mukherjee S, van der Donk W A. Mechanistic studies on the substrate-tolerant lanthipeptide synthetase ProcM. Journal of the American Chemical Society 2014; 136: 10450-10459.

Eder M, Schafer M, Bauder-Wust U, Hull W-E, Wangler C, Mier W, Haberkorn U, Eisenhut M. Bioconjugate Chemistry 2012; 23: 688-697.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A compound, the compound having Formula I or being a salt or solvate of Formula I

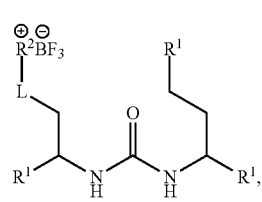

(I)

wherein:
each $R^1$ is independently CO$_2$H, PO$_3$H$_2$, SO$_2$H, SO$_3$H, SO$_4$H or OPO$_3$H$_2$;

$R^2BF_3$:

is —$N(R^3)_2CH_2BF_3$ wherein each $R^3$ is independently: H, methyl, $X_2$-$X_{15}$ akyl, $X_2$-$X_{15}$ heteroalkyl, $X_3$-$X_{15}$ aryl or $X_3$-$X_{15}$ heteroaryl; wherein the $X_2$-$X_{15}$ akyl or the $X_2$-$X_{15}$ heteroalkyl is one or more of: branched or linear; acyclic, cyclic or multi-cyclic; saturated or unsaturated; and optionally substituted with one or more of halide, amide, oxo, hydroxyl, thiol, phosphate and sulfate; wherein the $X_3$-$X_{15}$ aryl or the $X_3$-$X_{15}$ heteroaryl is one or more of: cyclic or multi-cyclic; aromatic or nonaromatic; and optionally substituted with one or more of halide, amide, oxo, hydroxyl, thiol, phosphate and sulfate; wherein each X is independently C, N, O, P, S or Se; and wherein the N in the —$N(R^3)_2CH_2BF_3$ is linked to the $X_2$-$X_{15}$ akyl, the $X_2$-$X_{15}$ heteroalkyl, the $X_3$-$X_{15}$ aryl or the $X_3$-$X_{15}$ heteroaryl through at least two C atoms in the $X_2$-$X_{15}$ akyl, the $X_2$-$X_{15}$ heteroalkyl, the $X_3$-$X_{15}$ aryl or the $X_3$-$X_{15}$ heteroaryl;

forms a pyridinium group that is C-substituted with —$B^-F_3$ or N-substituted with $CH_2B^-F_3$, and which is optionally substituted with one or more halogens, methyl groups, aryl groups, branched or linear alkyl groups, hydroxyls, esters, thiols, thioethers, amines, ketones, carboxaldehyde, carboxylates, carboxamides, nitriles, monohalomethyl groups, dihalomethyl groups and trihalomethyl groups; or forms:

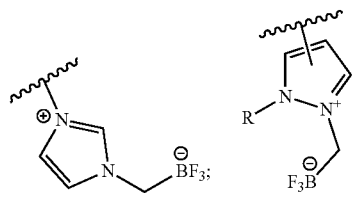

in which R is alkyl or aryl;

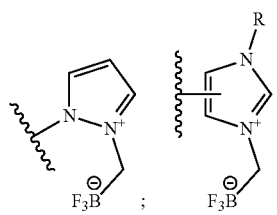

in which R is alkyl or aryl;

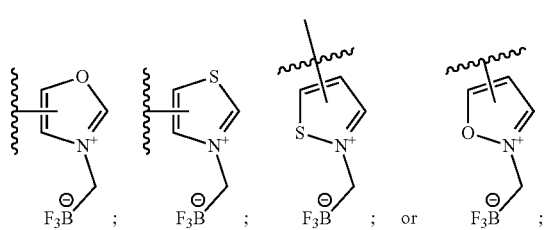

wherein the azole ring is optionally further substituted with one or more halogens, alkyls, ketones, carboxaldehyde, carboxylates, carboxamides, nitriles, monohalomethyl groups, dihalomethyl groups and trihalomethyl groups; and L is ether, ester, thioether, disulfide, thioester, amide, carbamate, ureido, phosphodiester, polyethylene glycol (PEG), peptide, polypeptide or $R^4R^5R^6$ in which $R^4$, $R^5$ and $R^6$ together form $X_1$-$X_{100}$ alkyl, $X_1$-$X_{100}$ heteroalkyl, $X_3$-$X_{100}$ aryl or $X_3$-$X_{100}$ heteroaryl, wherein the $X_1$-$X_{100}$ alkyl or the $X_1$-$X_{100}$ heteroalkyl of $R^4R^5R^6$ is one or more of: branched or linear; acyclic, cyclic or multi-cyclic; saturated or unsaturated; and optionally substituted with one or more of halide, amide, oxo, hydroxyl, thiol, phosphate and sulfate; wherein the $X_3$-$X_{15}$ aryl or the $X_3$-$X_{15}$ heteroaryl is one or more of: cyclic or multi-cyclic; aromatic or nonaromatic; and optionally substituted with one or more of halide, amide, oxo, hydroxyl, thiol, phosphate and sulfate; and wherein each X is independently C, N, O, P, S or Se.

2. The compound of claim 1, having Formula II or a salt or solvate thereof

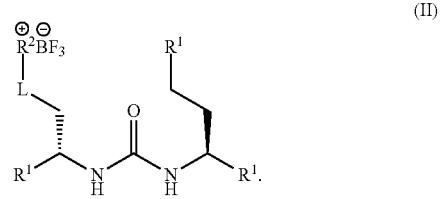

3. The compound of claim 1, wherein $R^1$ is $CO_2H$.

4. The compound of claim 1, wherein $R^2BF_3$ forms

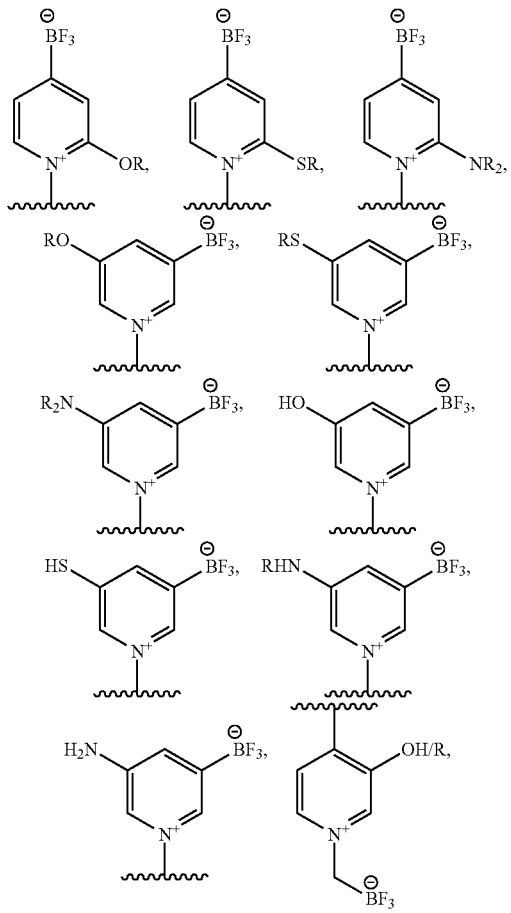

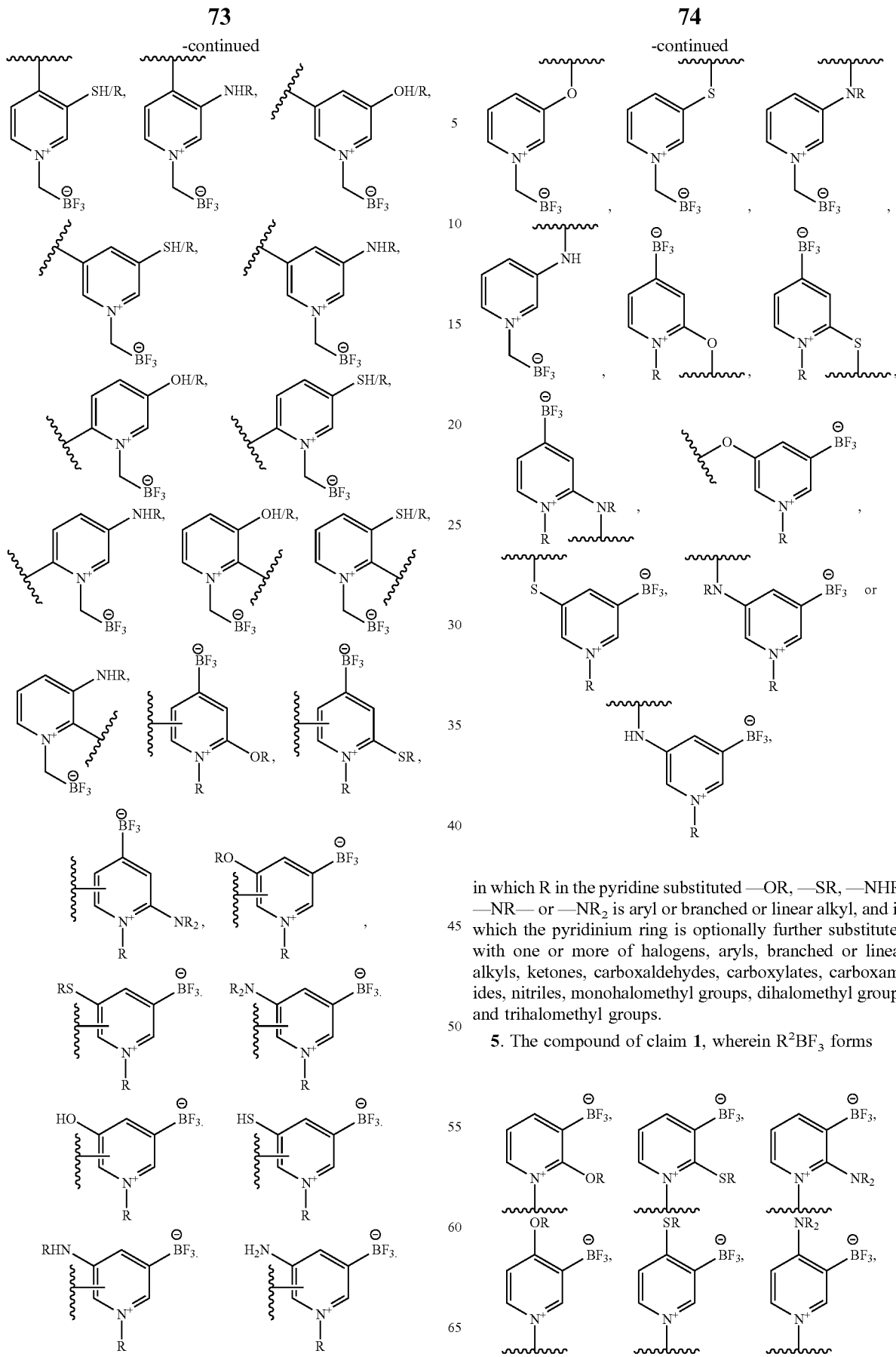

in which R in the pyridine substituted —OR, —SR, —NHR, —NR— or —NR₂ is aryl or branched or linear alkyl, and in which the pyridinium ring is optionally further substituted with one or more of halogens, aryls, branched or linear alkyls, ketones, carboxaldehydes, carboxylates, carboxamides, nitriles, monohalomethyl groups, dihalomethyl groups and trihalomethyl groups.

5. The compound of claim 1, wherein $R^2BF_3$ forms

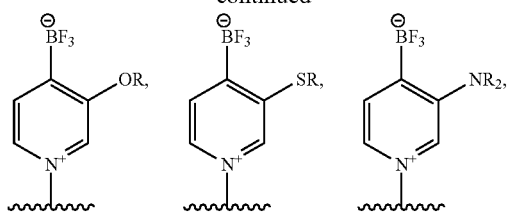
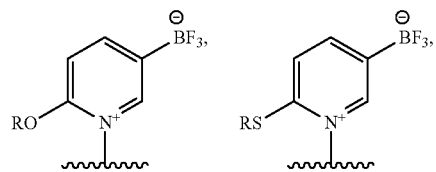
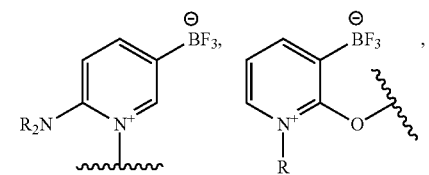
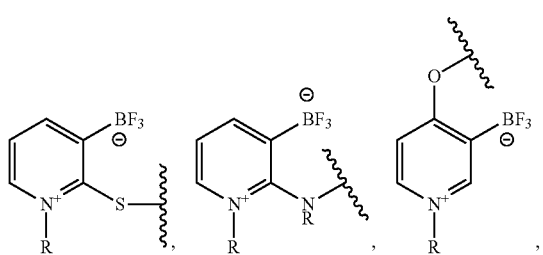
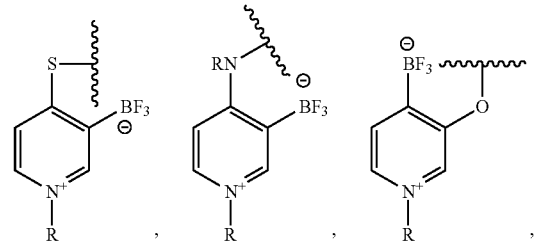
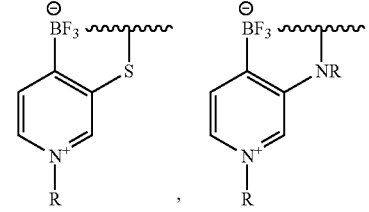
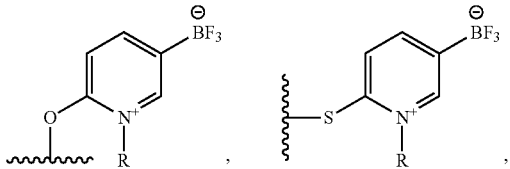
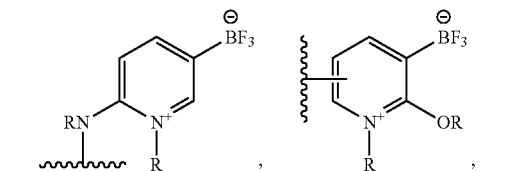
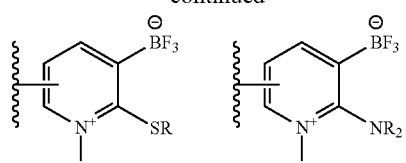
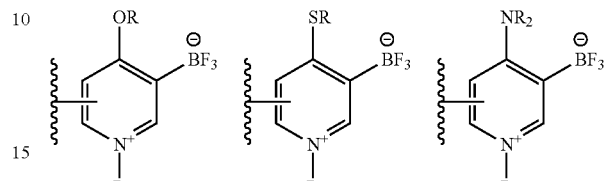
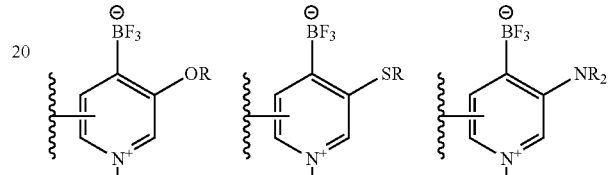
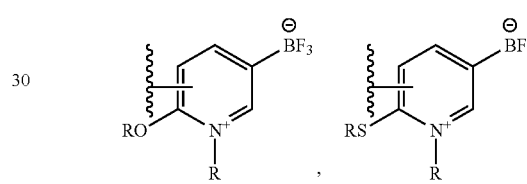
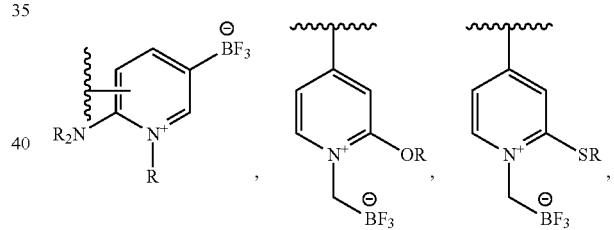
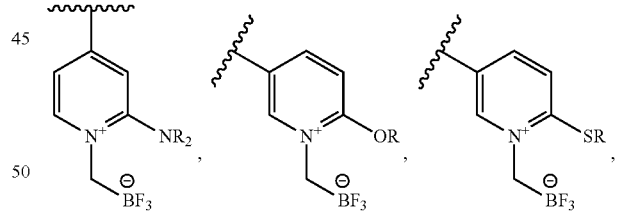
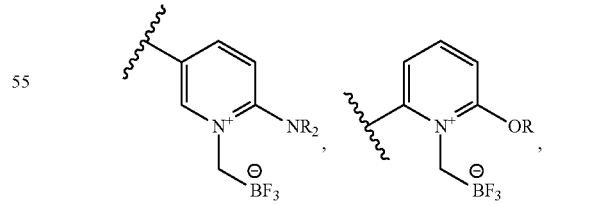
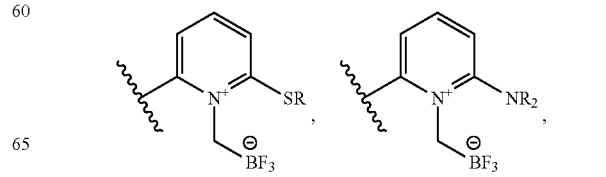

-continued

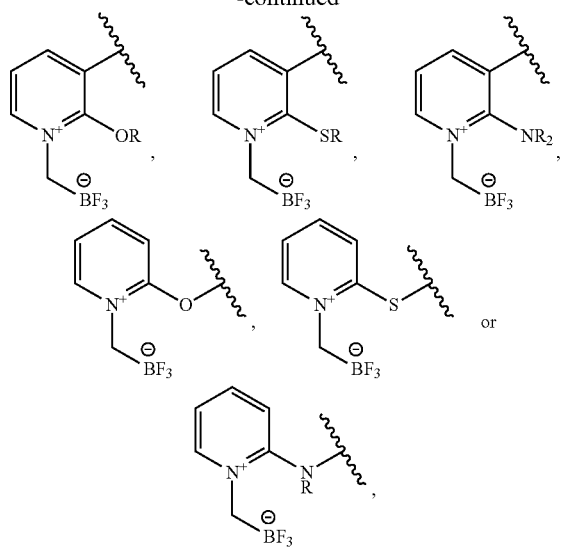

in which R in the pyridine substituted —OR, —SR, —NR— or —NR$_2$ is aryl or branched or linear alkyl, and in which the pyridinium ring is optionally further substituted with one or more of halogens, aryls, branched or linear alkyls, ketones, carboxaldehydes, carboxylates, carboxamides, nitriles, monohalomethyl groups, dihalomethyl groups and trihalomethyl groups.

6. The compound of claim 1, wherein R$^2$BF$_3$ is

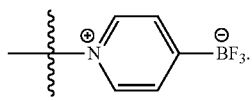

7. The compound of claim 1, wherein R$^4$ is absent, —CH$_2$—, —CH$_2$CH$_2$— or —CH$_2$CH$_2$CH$_2$.

8. The compound claim 1, wherein R$^5$ is —S—, —NHC(O)—, —C(O)—, —C(O)O— or —OC(O)—.

9. The compound of claim 1, wherein R$^6$ is (phenyl)CH$_2$R$^7$, (pyridyl)CH$_2$R$^7$, or

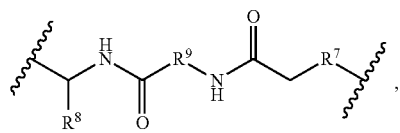

wherein R$^7$ is absent or

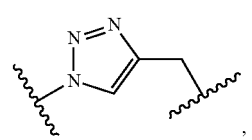

wherein R$^8$ is a an aliphatic or aromatic hydrophobic side chain of a natural or artificial amino acid, and wherein R$^9$ is an X$_1$-X$_{30}$ alkyl or X$_1$-X$_{30}$ heteroalkyl that is one or more of: branched or linear; acyclic, cyclic or multi-cyclic; saturated or unsaturated; and optionally substituted with one or more of halide, amide, oxo, hydroxyl, thiol, phosphate and sulfate; wherein each X is independently C, N, O, P, S or Se.

10. The compound of claim 9, wherein R$^6$ is

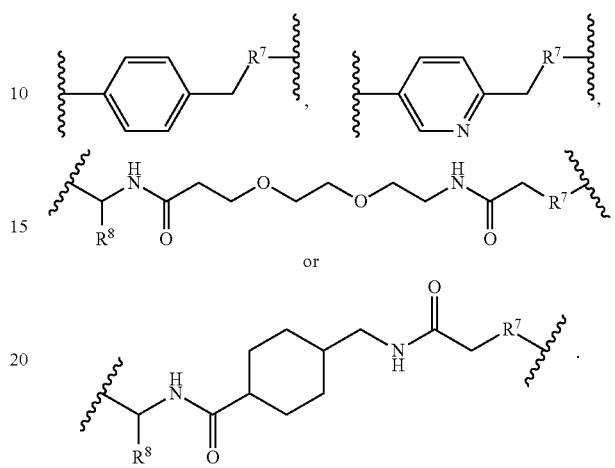

11. The compound of claim 9, wherein R$^8$ is:

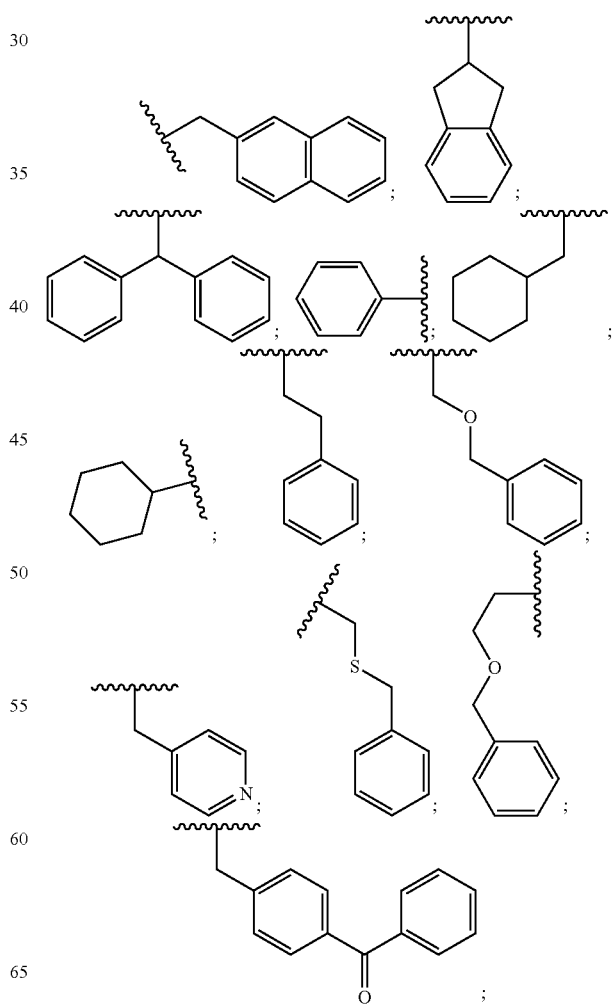

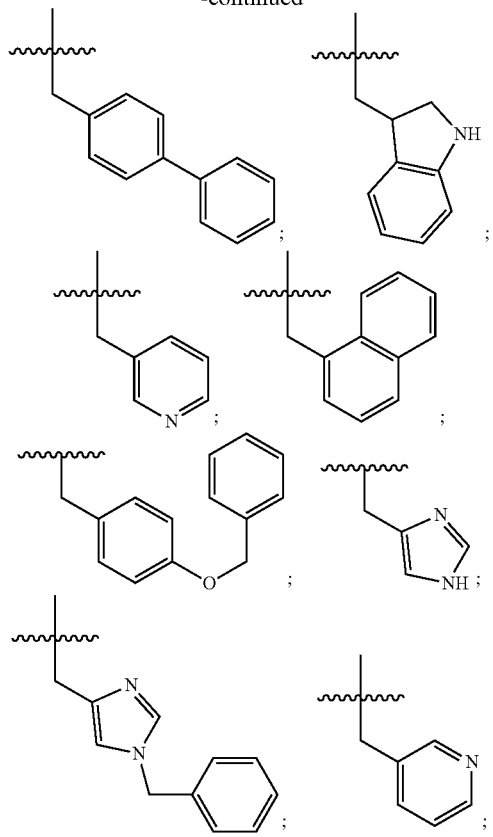
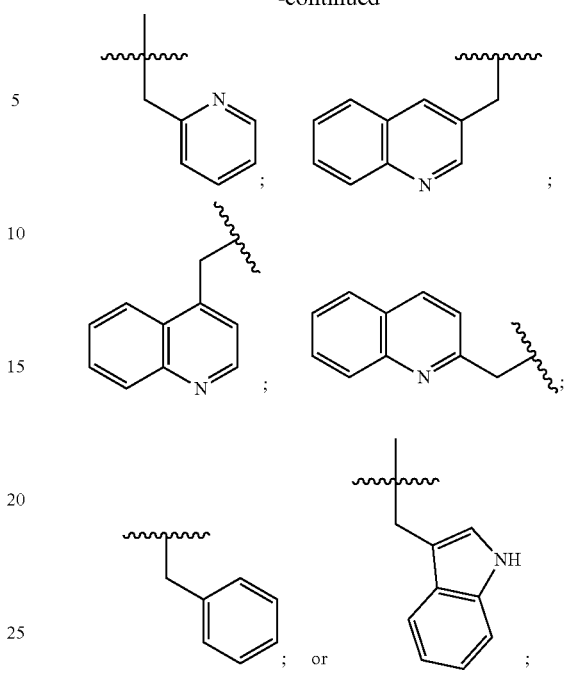
which is unsubstituted or substituted with one or more of halogen, nitro, carboxy, carboxamide, hydroxyl, $C_1$-$C_4$ alkyl, $C_1$-$C_4$ alkoxy, thiol, thioether or cyano groups at any or multiple positions on the ring.
12. A compound, which:
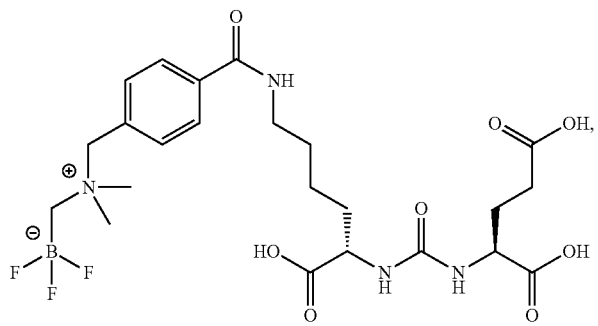
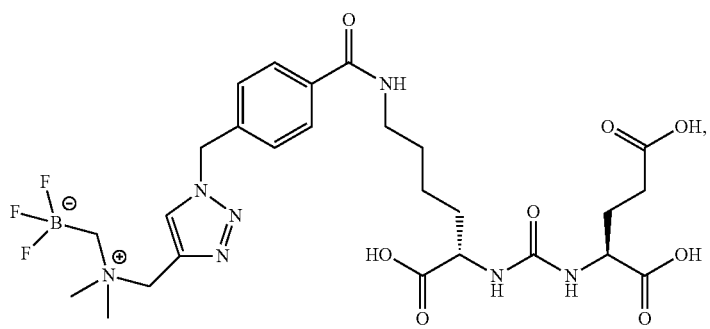

-continued
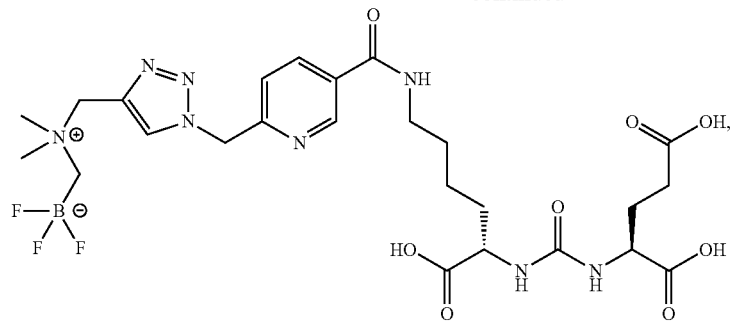
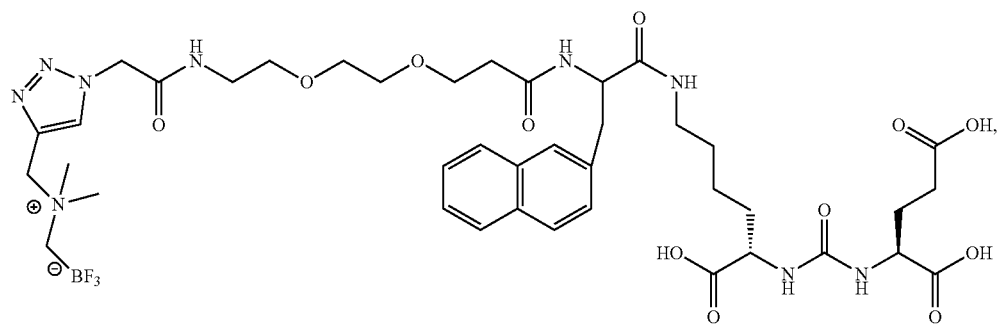
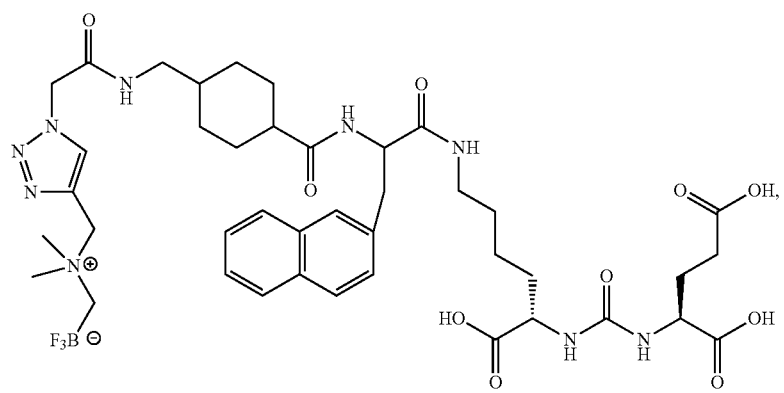
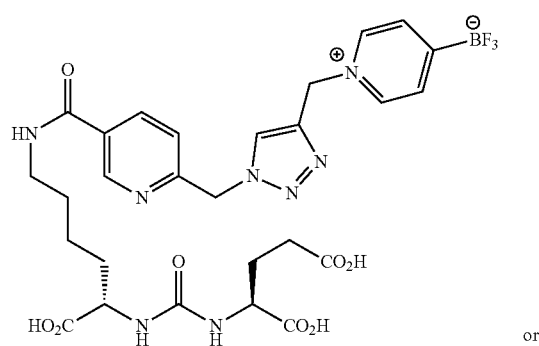
or

-continued

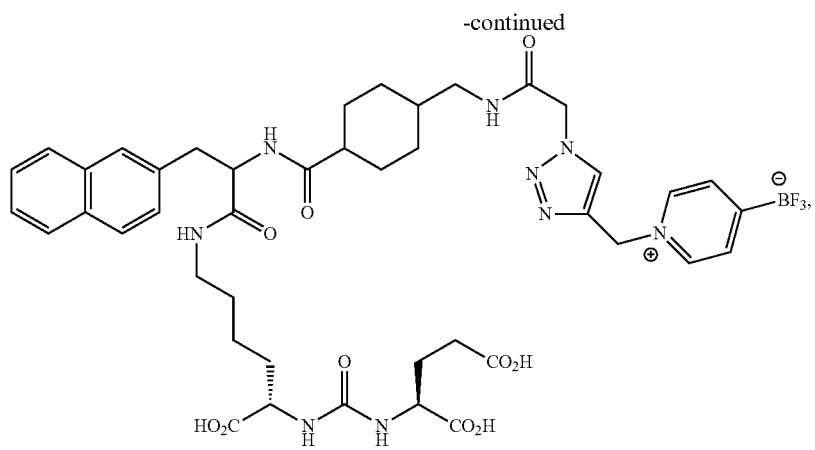

or a salt or solvate thereof.

13. The compound of claim 1, in which at least one fluorine in the —BF$_3$ moiety is $^{18}$F.

14. A method of imaging prostate specific membrane antigen (PSMA)-expressing cancer in a subject, the method comprising:
   administering to the subject a composition comprising the compound of claim 13 and a pharmaceutically acceptable excipient; and
   imaging tissue of the subject using positron emission tomography (PET).

15. A method of treating prostate specific membrane antigen (PSMA)-expressing cancer in a subject, the method comprising: administering to the subject a composition comprising the compound of claim 1 and a pharmaceutically acceptable excipient.

16. The method of claim 14, wherein the cancer is prostate cancer, renal cancer, breast cancer, thyroid cancer, gastric cancer, colorectal cancer, bladder cancer, pancreatic cancer, lung cancer, liver cancer, brain tumor, melanoma, neuroendocrine tumor, ovarian cancer or sarcoma.

17. The compound of claim 1, having Formula II or a salt or solvate thereof

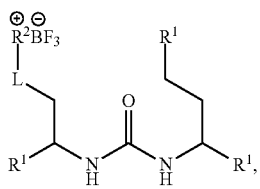

(I)

wherein:
each R$^1$ is independently CO$_2$H;
R$^2$BF$_3$:
is -N(CH$_3$)$_2$CH$_2$BF$_3$; or
forms a pyridinium group that is C-substituted with —B$^-$F$_3$ or N-substituted with —CH$_2$B$^-$F$_3$, and which is optionally substituted with one or more halogens, methyl groups, aryl groups, branched or linear alkyl groups, hydroxyls, thiols, amines, carboxaldehyde, carboxylates, carboxamides, nitriles, monohalomethyl groups, dihalomethyl groups and trihalomethyl groups; or forms:

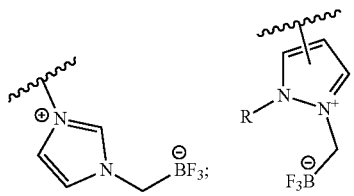

in which R is alkyl or aryl;

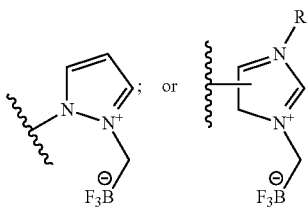

in which R is alkyl or aryl; wherein the azole ring is optionally further substituted with one or more halogens, alkyls, carboxaldehyde, carboxylates, carboxamides, nitriles, monohalomethyl groups, dihalomethyl groups and trihalomethyl groups; and L is ether, thioether, disulfide, amide, carbamate, ureido, polyethylene glycol (PEG), peptide, polypeptide, or R$^4$R$^5$R$^6$ in which:

R$^4$ is absent, -CH$_2$-, -CH$_2$CH$_2$- or -CH$_2$CH$_2$CH$_2$-.
R$^5$ is -S-, -NHC(O)-, -C(O)-, -C(O)O- or -OC(O)-;
R$^6$ is (phenyl)CH$_2$R$^7$, (pyridyl)CH$_2$R$^7$, or

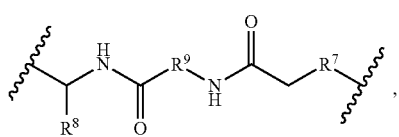

wherein R⁷ is absent or

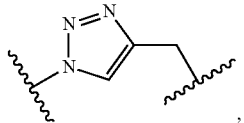

wherein R⁸ is a an aliphatic or aromatic hydrophobic side chain of a natural or artificial amino acid, and wherein R⁹ is a $C_1$-$C_{30}$ alkyl or $X_1$-$X_{30}$ heteroalkyl that is one or more of: branched or linear; acyclic, cyclic or multicyclic; saturated or unsaturated; and optionally substituted with one or more of halide, amide, oxo, hydroxyl, thiol, -$OPO_3H_2$ and —$OSO_3H$; and wherein each X is independently C or a heteroatom selected from N, O, P, S or Se.

18. A compound, the compound having Formula II or a salt or solvate thereof

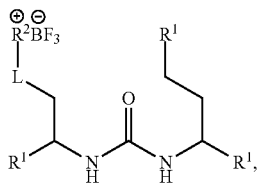

(I)

wherein:
each R¹ is independently $CO_2H$; $R^2BF_3$:
is -$N(CH_3)_2CH_2BF_3$; or forms

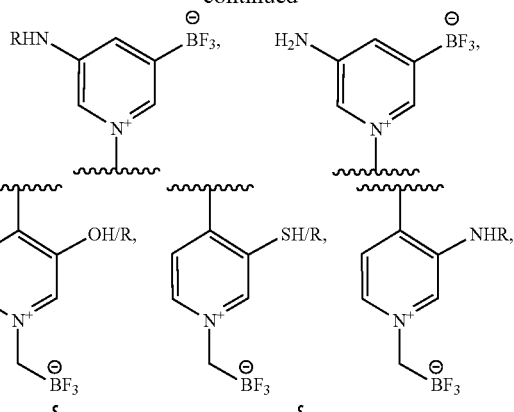

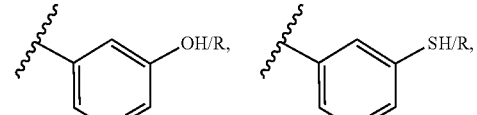
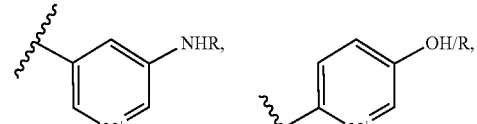
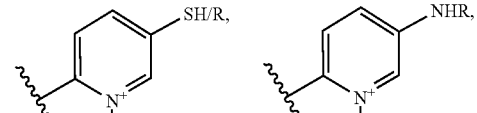
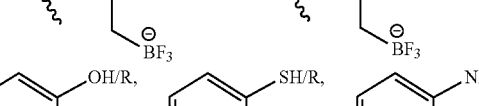
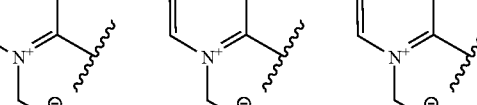
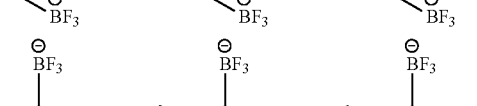
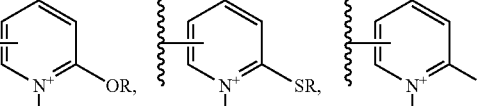
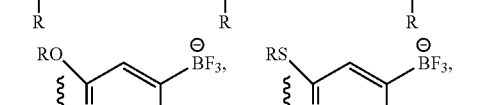
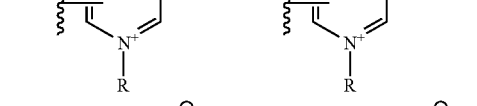
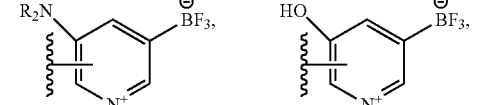

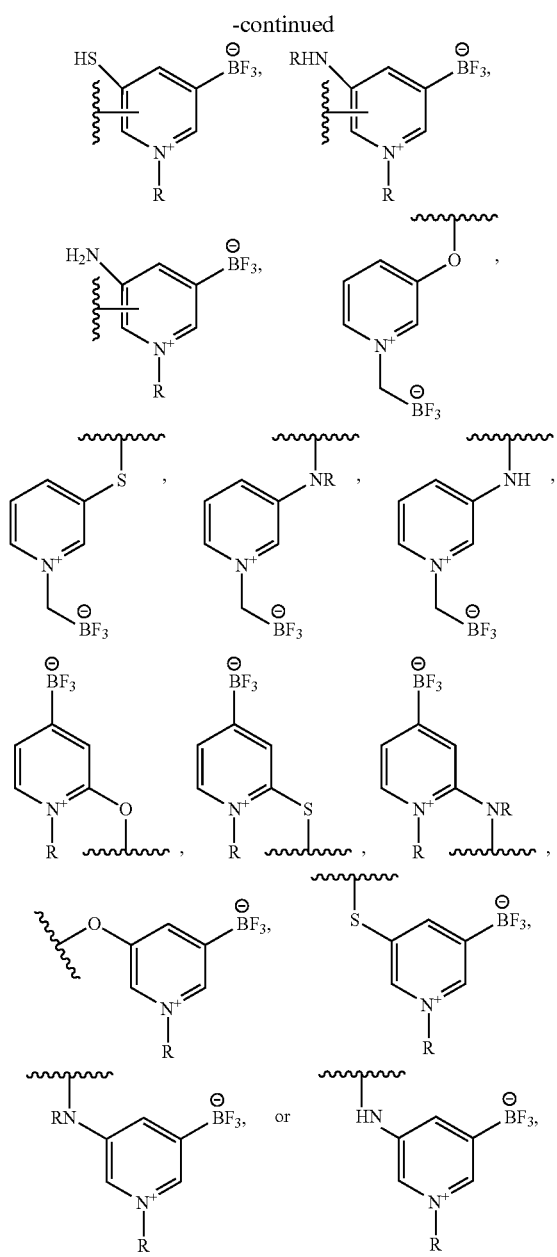

in which R in the pyridine substituted —OR, —SR, —NHR, —NR— or —NR$_2$ is aryl or branched or linear alkyl, and in which the pyridinium ring is optionally further substituted with one or more of halogens, aryls, branched or linear alkyls, carboxaldehydes, carboxylates, carboxamides, nitriles, monohalomethyl groups, dihalomethyl groups and trihalomethyl groups; or

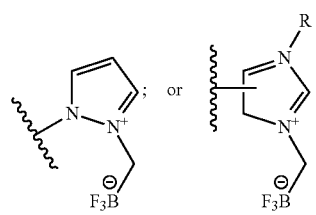

forms: in which R is alkyl or aryl;

in which R is alkyl or aryl; wherein the azole ring is optionally further substituted with one or more halogens, alkyls, carboxaldehyde, carboxylates, carboxamides, nitriles, monohalomethyl groups, dihalomethyl groups and trihalomethyl groups; and L is $R^4R^5R^6$ in which:

$R^4$ is absent, -CH$_2$-, -CH$_2$CH$_2$- or -CH$_2$CH$_2$CH$_2$-.

$R^5$ is -S-, -NHC(O)-, -C(O)-, -C(O)O- or -OC(O)-;

$R^6$ is (phenyl)CH$_2R^7$, (pyridyl)CH$_2R^7$,

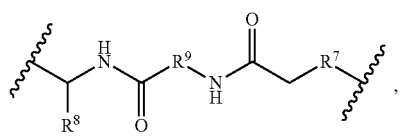

or wherein $R^7$ is absent or

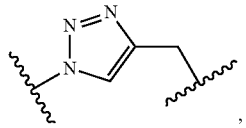

wherein $R^8$ is a an aliphatic or aromatic hydrophobic side chain of a natural or artificial amino acid, and wherein $R^9$ is a $C_1$-$C_{30\ alkyl\ or}$ $X_1$-$X_{30}$ heteroalkyl that is one or more of: branched or linear; acyclic, cyclic or multicyclic; saturated or unsaturated; and optionally substituted with one or more of halide, amide, oxo, hydroxyl, thiol, -OPO$_3$H$_2$ and —OSO$_3$H; and wherein each X is independently C or a heteroatom selected from N, O, P, S or Se.

19. The compound of claim 18, wherein:

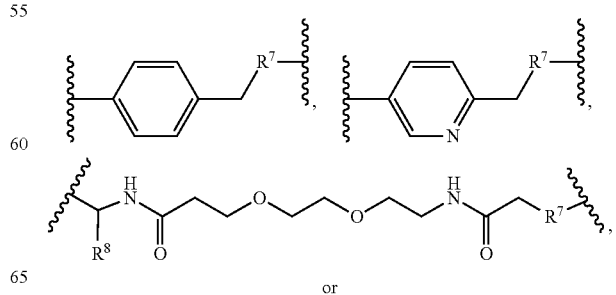

or

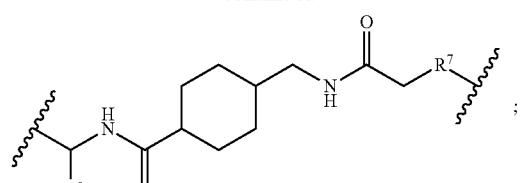
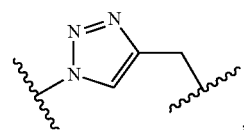 [SMILES: *Cc1cn(*)nn1]
R⁶ is
R⁷ is absent or and
R⁸ is:
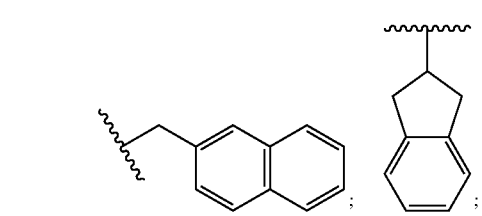
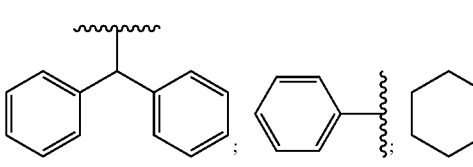
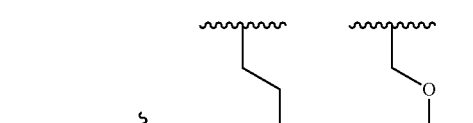
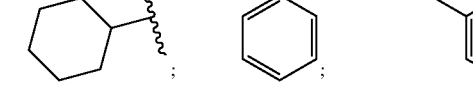
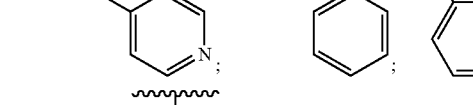
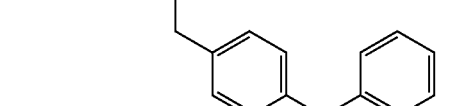
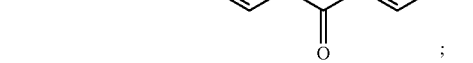
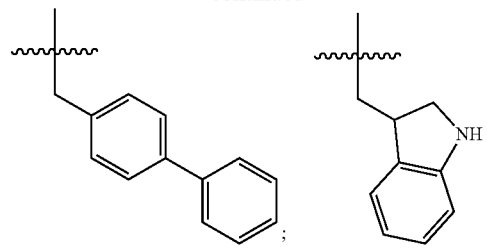
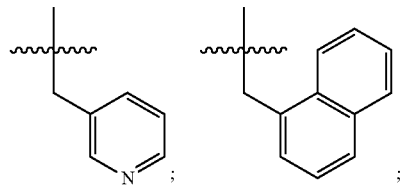
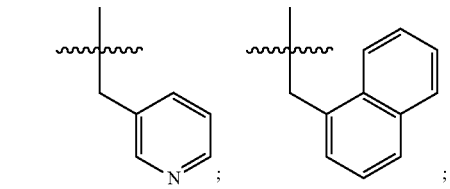
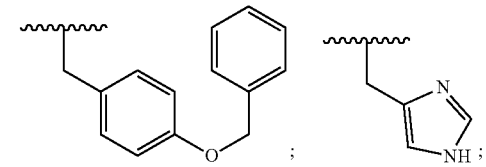
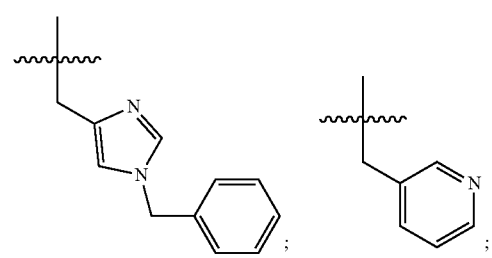
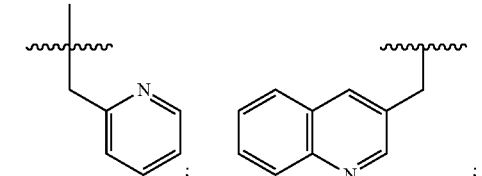
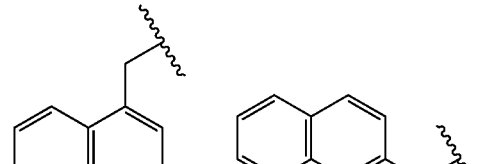
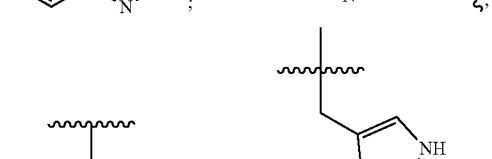
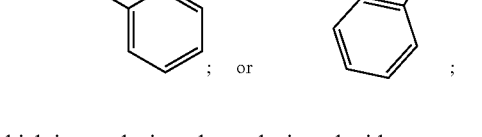
which is unsubstituted or substituted with one or more of halogen, nitro, carboxy, carboxamide, hydroxyl, $C_1$-$C_4$ alkyl, $C_1$-$C_4$ alkoxy, thiol, thioether or cyano groups at any or multiple positions on the ring.

20. The compound of claim 18, wherein:
$R^2BF_3$:
  is $-N(CH_3)_2CH_2BF_3$; or
  forms
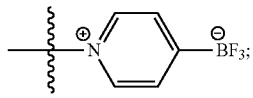
or
forms:
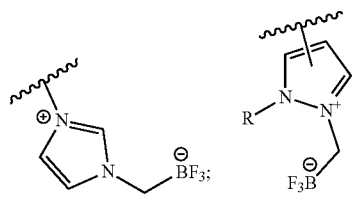
in which R is alkyl or aryl;
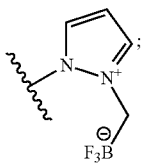
$R^4$ is $-CH_2-$, $-CH_2CH_2-$ or $-CH_2CH_2CH_2-$;
$R^5$ is $-S-$, $-NHC(O)-$, $-C(O)-$, $-C(O)O-$ or $-OC(O)-$; $R^6$ is
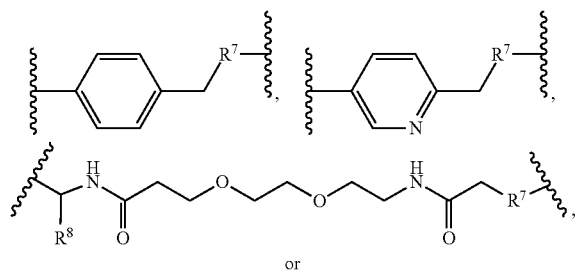
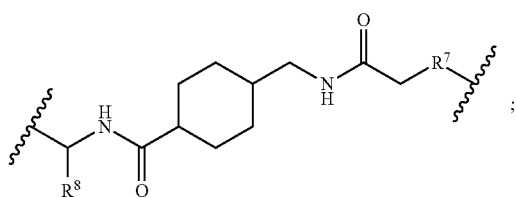
or
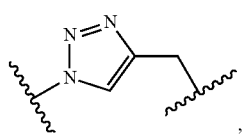 [SMILES: *Cc1cn(*)nn1]
$R^7$ is absent or and
$R^8$ is:
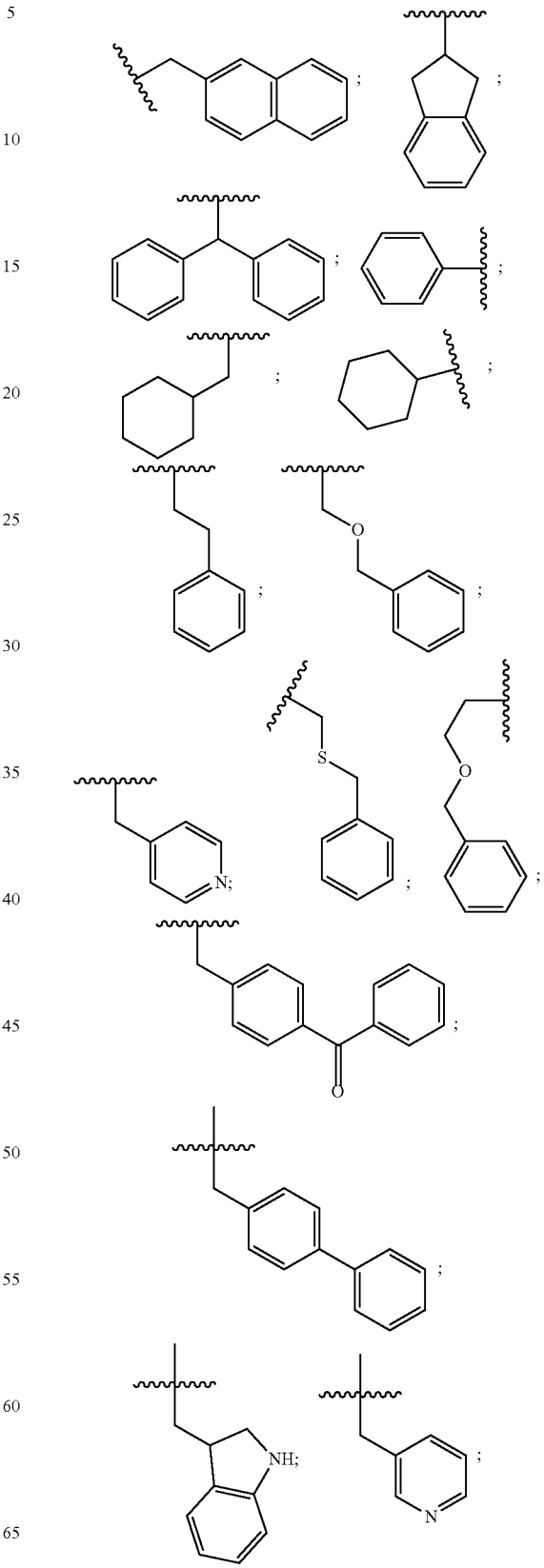

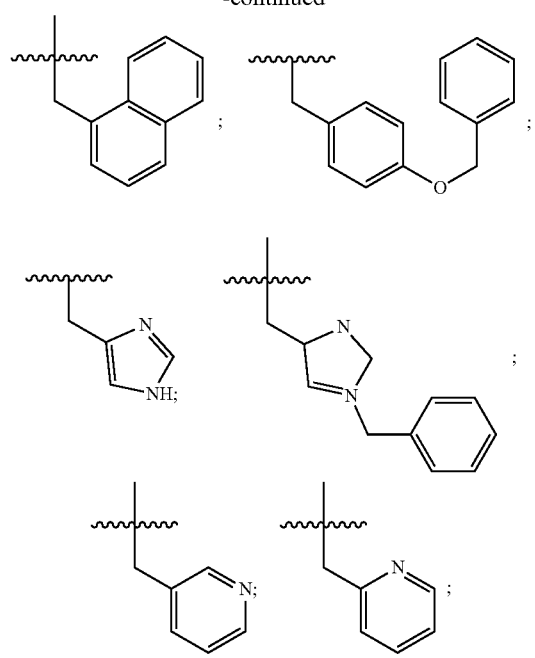
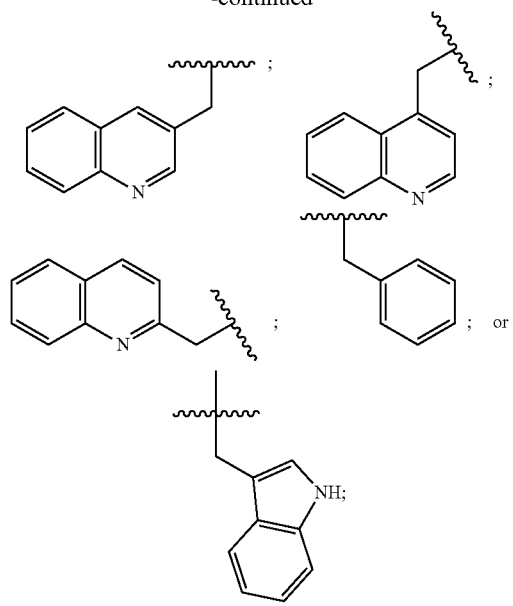
* * * * *